United States Patent
Small et al.

(10) Patent No.: US 10,544,070 B2
(45) Date of Patent: *Jan. 28, 2020

(54) ETHYLENE OLIGOMERIZATION PROCESS

(71) Applicant: Chevron Phillips Chemical Company LP, The Woodlands, TX (US)

(72) Inventors: Brooke L. Small, Kingwood, TX (US); Matthew F. Milner, Kingwood, TX (US)

(73) Assignee: Chevron Phillips Chemical Company, LP, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/420,415

(22) Filed: May 23, 2019

(65) Prior Publication Data
US 2019/0276377 A1 Sep. 12, 2019

Related U.S. Application Data

(63) Continuation of application No. 15/852,623, filed on Dec. 22, 2017, now Pat. No. 10,407,360.

(51) Int. Cl.
C07C 2/32 (2006.01)

(52) U.S. Cl.
CPC .......... *C07C 2/32* (2013.01); *C07C 2527/128* (2013.01); *C07C 2531/02* (2013.01); *C07C 2531/04* (2013.01); *C07C 2531/14* (2013.01); *C07C 2531/22* (2013.01)

(58) Field of Classification Search
None
See application file for complete search history.

(56) References Cited

U.S. PATENT DOCUMENTS

| | | |
|---|---|---|
| 3,676,523 A | 7/1972 | Mason |
| 5,451,645 A | 11/1995 | Raegen et al. |
| 5,955,555 A | 11/1999 | Bennett |
| 6,103,946 A | 9/2000 | Brookhart, III et al. |
| 6,214,761 B1 | 4/2001 | Bennett |
| 6,291,733 B1 | 9/2001 | Small et al. |
| 6,417,305 B2 | 7/2002 | Bennett |
| 6,423,848 B2 | 7/2002 | Bennett |
| 6,432,862 B1 | 8/2002 | Bennett |
| 6,451,939 B1 | 9/2002 | Britovsek et al. |
| 6,455,660 B1 | 9/2002 | Clutton et al. |
| 6,458,739 B1 | 10/2002 | Kimberley et al. |
| 6,458,905 B1 | 10/2002 | Schmidt et al. |
| 6,461,994 B1 | 10/2002 | Gibson et al. |
| 6,472,341 B1 | 10/2002 | Kimberly et al. |
| 6,489,497 B1 | 12/2002 | Brookhart, III et al. |
| 6,534,691 B2 | 3/2003 | Culver et al. |
| 6,545,108 B1 | 4/2003 | Moody et al. |
| 6,555,723 B2 | 4/2003 | Schiffino |
| 6,559,091 B1 | 5/2003 | Moody et al. |
| 6,657,026 B1 | 12/2003 | Kimberley et al. |
| 6,683,187 B2 | 1/2004 | De Boer et al. |
| 6,710,006 B2 | 3/2004 | De Boer et al. |
| 6,740,715 B2 | 5/2004 | Brookhart, III et al. |
| 6,911,505 B2 | 6/2005 | Small et al. |
| 6,911,506 B2 | 6/2005 | Small et al. |
| 7,001,964 B2 | 2/2006 | Small |
| 7,037,988 B2 | 5/2006 | De Boer et al. |
| 7,045,632 B2 | 5/2006 | Small |
| 7,049,442 B2 | 5/2006 | De Boer et al. |
| 7,053,020 B2 | 5/2006 | De Boer et al. |
| 7,053,259 B2 | 5/2006 | Culver et al. |
| 7,056,997 B2 | 6/2006 | Small et al. |
| 7,129,304 B1 | 10/2006 | Small et al. |
| 7,223,893 B2 | 5/2007 | Small et al. |
| 7,268,096 B2 | 9/2007 | Small et al. |
| 7,271,121 B2 | 9/2007 | Small et al. |
| 7,297,806 B2 | 11/2007 | Brookhart, III et al. |

(Continued)

FOREIGN PATENT DOCUMENTS

| | | |
|---|---|---|
| CA | 2020509 A1 | 2/1991 |
| CN | 104418690 A | 3/2015 |

(Continued)

OTHER PUBLICATIONS

Agapie, T., "Selective ethylene oligomerization: Recent advances in chromium catalysis and mechanistic investigations," Coordination Chemistry Reviews, 2011, vol. 255, pp. 861-880, Elsevier B.V.
Bennett, A. et al., "Novel, highly active iron and cobalt catalysts for olefin polymerization," CHEMTECH, Jul. 1999, pp. 24-28, vol. 29, American Chemical Society.
Britovsek, G. et al., "Iron and Cobalt Ethylene Polymerization Catalysts bearing 2,6-Bis(imino)Pyridyl Ligands: Synthesis, Structures and Polymerization Studies," Journal of the American Chemical Society, 1999, pp. 8728-8740, vol. 121, American Chemical Society.
Britovsek, G. et al., "Novel olefin polymerization catalysts based on iron and cobalt," Chemical Communication, 1998, pp. 849-850, vol. 7.
Britovsek, G. et al., "Oligomerization of Ethylene by Bis(imino)pyridyliron and -cobalt Complexes," Chemistry—A European Journal, 2000, pp. 2221-2231, vol. 6, No. 12, Wiley-VCH.

(Continued)

*Primary Examiner* — Philip Y Louie
(74) *Attorney, Agent, or Firm* — Conley Rose, P.C.

(57) ABSTRACT

Disclosed herein is a process for forming an oligomer product comprising (a) introducing into a reaction zone (i) ethylene; (ii) a heteroatomic ligand metal salt complex comprising a heteroatomic ligand complexed to a first metal salt; (iii) a second metal salt wherein an equivalent molar ratio of the second metal salt to the heteroatomic ligand of the heteroatomic ligand metal salt complex is at least 0.5:1 and where the second metal salt is an iron salt, a cobalt salt, or any combination thereof; (iv) an organoaluminum compound; and (b) forming an oligomer product. Also disclosed herein is a process comprising (a) introducing into a reaction zone (i) ethylene; (ii) a heteroatomic ligand; (iii) a metal salt where an equivalent molar ratio of the metal salt to the heteroatomic ligand is at least 1.5:1; (iv) an organoaluminum compound; and (b) forming an oligomer product.

16 Claims, No Drawings

(56) References Cited

U.S. PATENT DOCUMENTS

| | | |
|---|---|---|
| 7,304,159 B2 | 12/2007 | De Boer et al. |
| 7,442,819 B2 | 10/2008 | Ionkin et al. |
| 7,456,284 B2 | 11/2008 | Small |
| 7,683,149 B2 | 3/2010 | Ionkin et al. |
| 7,902,415 B2 | 3/2011 | Small |
| 7,994,376 B2 | 8/2011 | Small et al. |
| 2002/0016425 A1 | 2/2002 | De Boer et al. |
| 2005/0014983 A1 | 1/2005 | De Boer et al. |
| 2005/0187418 A1 | 8/2005 | Small et al. |
| 2007/0112150 A1 | 5/2007 | Small et al. |
| 2007/0185289 A1* | 8/2007 | Lin ................ C08F 10/00 526/171 |
| 2007/0221608 A1 | 9/2007 | Axe et al. |
| 2010/0274065 A1 | 10/2010 | Sydora |
| 2013/0018214 A1* | 1/2013 | Zheng ............... B01J 31/143 585/513 |
| 2013/0172651 A1 | 7/2013 | Small |
| 2013/0211168 A1 | 8/2013 | Breuil et al. |
| 2016/0229766 A1 | 8/2016 | Sydora et al. |
| 2018/0186708 A1 | 7/2018 | Bischof et al. |
| 2018/0186709 A1 | 7/2018 | Bischof et al. |
| 2019/0077888 A1 | 3/2019 | Aida et al. |

FOREIGN PATENT DOCUMENTS

| | | |
|---|---|---|
| CN | 105884565 A | 8/2016 |
| EP | 1229020 A1 | 8/2002 |
| WO | 2004026795 A2 | 4/2004 |
| WO | 2005005354 A1 | 1/2005 |
| WO | 2010051415 A1 | 5/2010 |
| WO | 2011126787 A1 | 10/2011 |
| WO | 2013101387 A1 | 7/2013 |
| WO | 2018125824 A1 | 7/2018 |
| WO | 2018125826 A1 | 7/2018 |
| WO | 2018128861 A1 | 7/2018 |

OTHER PUBLICATIONS

Chen, Y., et al., "Fluoro-Substituted 2,6-Bis(imino)pyridyl Iron and Cobalt Complexes: High-Activity Ethylene Oligomerization Catalysts," Organometallics, 2003, pp. 1231-1236, vol. 32, American Chemical Society.

Chen, Y., et al., Halogen-Substituted 2,6-Bis(imino)pyridyl Iron and cobalt Complexes: Highly Active Catalysts for Polymerization and Oligomerization of Ethylene, Organometallics, 2003, pp. 4312-4321, vol. 22, American Chemical Society.

Dixon, J., et al., "Advances in selective ethylene trimerisation—a critical overview," Journal of Organometallic Chemistry, 2004, vol. 689, pp. 3641-3668, Elsevier B. V.

Ionkin, A., et al., "High-Temperature Catalysts for the Production of α-Olefins Based on Iron(II) and Cobalt(II) Tridentate Bis(imino)pyridine Complexes with a Double Pattern of Substitution: o-Methyl plus o-Fluorine in the Same Imino Arm," Organometallics, 2008, pp. 1147-1156, vol. 27, American Chemical Society.

Ionkin, A., et al., "High-Temperature Catalysts for the Production of α-Olefins Based on Iron(II) and Iron(III) Tridentate Bis(imino)pyridine Complexes Modified by Nitrilo Group," J. Poly. Sci.: Part A Poly. Chem., 2008, pp. 585-611, vol. 46.

Ionkin, A., et al., "High-Temperature Catalysts for the Production of α-Olefins Based on Iron(II) and Iron(III) Tridentate Bis(imino)pyridine Complexes with Double Pattern of Substitution: ortho-Methyl plus meta-Aryl," Organometallics, 2006, pp. 2987-2992, vol. 25, American Chemical Society.

Ionkin, A., et al., "Modification of Iron(II) Tridentate Bis(imino)pyridine Complexes by a Boryl Group for the Production of α-Olefins at High Temperature," Organometallics, 2008, pp. 1902-1911, vol. 27, American Chemical Society.

Manyik, R., et al., "A Soluble Chromium-based Catalyst for Ethylene Trimerization and Polymerization," Journal of Catalysis, 1977, vol. 47, pp. 197-209, Academic Press, Inc.

McNaught, Alan D., et al., "Compendium of Chemical Terminology," IUPAC Recommendations, Second edition, 1997, 5 pages, Wiley-Blackwell.

Schmiege, B., et al., "Alternatives to pyridinediimine ligands: syntheses and structures of metal complexes supported by donor-modified α-diimine ligands," Dalton Transactions, 2007, vol. 24, pp. 2547-2562, Royal Society of Chemistry.

Small, B. et al., "Highly Active Iron and Cobalt Catalysts for the Polymerization of Ethylene," Journal of the American Chemical Society, 1998, pp. 4049-4050, vol. 120, American Chemical Society.

Small, B. et al., "Iron-Based Catalysts with Exceptionally High Activities and Selectivities for Oligomerization of Ethylene to Linear α-Olefins," Journal of the American Chemical Society, 1998, pp. 7143-7144, vol. 120, American Chemical Society.

Small, B. et al., "Polymerization of Propylene by a New Generation of Iron Catalysts: Mechanisms of Chain Initiation, Propagation, and Termination," Macromolecules, Oct. 29, 1999, pp. 2120-2130, vol. 32, American Chemical Society.

Small, B., et al., "Oligomerization of Ethylene using New Iron Catalysts Bearing Pendant Donor Modified α-Diimine Ligands," Organometallics, 2007, vol. 26, pp. 1744-1749, American Chemical Society.

Small, B., et al., "Oligomerization of Ethylene Using New Tridentate Iron Catalysts Bearing α-Diimine Ligands with Pendant S and P Donors," Organometallics, 2010, vol. 29, pp. 6723-6731, American Chemical Society.

Zhang, Z., et al., "Ethylene oligomerization catalyzed by a novel iron complex containing fluoro and methyl substituents," Journal of Molecular catalysis A: Chemical, 2004, pp. 249-254, vol. 219, Elsevier B.V.

"Group notation revised in periodic table," Feb. 4, 1985, C&EN, p. 27.

Boudier, Adrien, et al., "Novel Catalytic System for Ethylene Oligomerization: An Iron(III) Complex with an Anionic N,N,N Ligand," Organometallics, 2011, vol. 30, pp. 2640-2642, American Chemical Society.

Sun, Wen-Hua, et al., "Iron Complexes Bearing 2-Imino-1,10-phenanthrolinyl Ligands as Highly Active Catalysts for Ethylene Oligomerization," Organometallics, 2006, vol. 25, pp. 666-677, American Chemical Society.

Filing Receipt and Specification of U.S. Appl. No. 15/852,623, filed Dec. 22, 2017, by Steven Bischof, et al. and entitled "Ethylene Oligomerization Processes" 103 pages.

Foreign communication from a counterpart application—International Search Report and Written Opinion, PCT/US2017/068281, dated Apr. 9, 2018, 13 pages.

Foreign communication from a counterpart application—Invitation to Pay Additional Fees and Partial Search Report, PCT/US2017/068278, dated Apr. 9, 2018, 14 pages.

Foreign communication from a related application—International Search Report and Written Opinion, PCT/US2017/068274, dated Jun. 7, 2018, 23 pages.

Foreign communication from a related application—International Search Report and Written Opinion, PCT/US2017/068278, dated May 30, 2018, 18 pages.

Office Action dated Feb. 8, 2018 (51 pages), U.S. Appl. No. 15/394,317, filed Dec. 29, 2016.

Office Action dated Feb. 8, 2018 (44 pages), U.S. Appl. No. 15/394,411, filed Dec. 29, 2016.

Office Action dated Feb. 8, 2018 (58 pages), U.S. Appl. No. 15/852,623, filed Dec. 22, 2017.

Final Office Action dated Aug. 30, 2018 (39 pages), U.S. Appl. No. 15/394,317, filed Dec. 29, 2016.

Final Office Action dated Aug. 30, 2018 (49 pages), U.S. Appl. No. 15/394,411, filed Dec. 29, 2016.

Final Office Action dated Aug. 30, 2018 (43 pages), U.S. Appl. No. 15/852,623, filed Dec. 22, 2017.

Advisory Action dated Oct. 30, 2018 (4 pages), U.S. Appl. No. 15/394,411, filed Dec. 29, 2016.

Office Action dated Jan. 11, 2019 (22 pages), U.S. Appl. No. 15/394,317, filed Dec. 29, 2016.

(56) References Cited

OTHER PUBLICATIONS

Office Action dated Jan. 24, 2019 (25 pages), U.S. Appl. No. 15/852,623, filed Dec. 22, 2017.
Notice of Allowance dated Apr. 30, 2019 (12 pages), U.S. Appl. No. 15/852,623, filed Dec. 22, 2017.
Walsh, R., et al., "Tetramerisation Process Technology Review," The IP.com Prior Art Database, Jul. 13, 2004, Sasol Technology (Pty) Ltd.

* cited by examiner

US 10,544,070 B2

ETHYLENE OLIGOMERIZATION PROCESS

CROSS-REFERENCE TO RELATED APPLICATIONS

This application is a continuation of and claims priority to U.S. patent application Ser. No. 15/852,623 filed Dec. 22, 2017 and entitled "Ethylene Oligomerization Processes," which is incorporated by reference herein in its entirety.

FIELD

The present disclosure relates to processes for producing alpha olefins. More particularly, the present disclosure relates to improved processes for oligomerizing ethylene.

BACKGROUND

Alpha olefins are important items of commerce. Their many applications include employment as intermediates in the manufacture of detergents, as precursors to more environmentally friendly refined oils, as monomers, and as precursors for many other types of products. One method of making alpha olefins is via oligomerization of ethylene in a catalytic reaction involving various types of catalysts and/or catalyst systems. Examples of catalysts and catalyst systems used commercially in the oligomerization of ethylene include alkylaluminum compounds, certain nickel-phosphine complexes, a titanium halide with a Lewis acid (e.g., diethylaluminum chloride), a selective 1-hexene catalyst system containing a chromium containing compound (e.g., a chromium carboxylate), a nitrogen containing ligand (e.g., a pyrrole) and a metal alkyl (e.g., alkylaluminum compounds), and a selective trimerization and/or tetramerization catalyst system using a metal complex of a compound having a diphosphinylaminyl group.

Several oligomerization catalyst systems to produce alpha olefins are based upon metal complexes of pyridine bis-imines and metal complexes of α-diimine compounds having a metal complexing group, among others. These catalyst systems typically use an organoaluminum compound (e.g., aluminoxane) as a component of the catalyst system for olefin oligomerization.

Applications and demand for olefins (e.g., alpha olefins) continue to multiply and competition to supply them correspondingly intensifies. Thus, additional novel and improved catalyst systems and processes for olefin oligomerization are desirable.

SUMMARY

Disclosed herein is a process for forming an oligomer product comprising (a) introducing into a reaction zone (i) ethylene; (ii) a heteroatomic ligand metal salt complex comprising a heteroatomic ligand complexed to a first metal salt where the first metal salt is an iron salt, a cobalt salt, or a combination thereof; (iii) a second metal salt wherein an equivalent molar ratio of the second metal salt to the heteroatomic ligand of the heteroatomic ligand metal salt complex is at least 0.5:1 and where the second metal salt is an iron salt, a cobalt salt, or any combination thereof; (iv) an organoaluminum compound; (v) optionally hydrogen; and (vi) optionally an organic reaction medium; and (b) forming an oligomer product in the reaction zone.

Also disclosed herein is a process for forming an oligomer product comprising (a) introducing into a reaction zone (i) ethylene; (ii) a heteroatomic ligand; (iii) a metal salt where (1) the metal salt is an iron salt, a cobalt salt, or any combination thereof, and (2) an equivalent molar ratio of the metal salt to the heteroatomic ligand is at least 1.5:1; (iv) an organoaluminum compound; (v) optionally hydrogen; and (vi) optionally an organic reaction medium; and (b) forming an oligomer product in the reaction zone.

BRIEF DESCRIPTION OF DRAWINGS

Not applicable.

DETAILED DESCRIPTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme found in the version of the periodic table of elements published in Chemical and Engineering News, 63(5), 27, 1985. In some instances, a group of elements can be indicated using a common name assigned to the group; for example alkali metals for Group 1 elements, alkaline earth metals for Group 2 elements, transition metals for Group 3-12 elements, and halogens for Group 17 elements, among others.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms "comprising," "consisting essentially of," and "consisting of" apply only to the feature class which is utilized and it is possible to have different transitional terms or phrases utilized with different features within a claim. For example, a method can comprise several recited steps (and other non-recited steps) but utilize a catalyst system preparation consisting of specific or alternatively, consist of specific steps and/or utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of" or "consist of" the various components or steps.

In the specification and claims, the terms "a," "an," and "the" are intended, unless specifically indicated otherwise, to include plural alternatives, e.g., at least one, or one or more. For instance, the disclosure of "a trialkylaluminum compound" is meant to encompass one trialkylaluminum compound, or mixtures or combinations of more than one trialkylaluminum compound unless otherwise specified.

In this disclosure, the terms first, second, and third, among others, can be utilized to differentiate multiple occurrences of a similar element. For example, a method can utilize two or more solvents in different steps of a method, or alternatively, two different solvents in a mixture. The differentiating term can be applied to any element described herein when necessary to provide a differentiation. It should be understood that the numerical or alphabetical precedence of the differentiating terms do not imply a particular order or preference of the element in a method or compound described herein unless specified otherwise.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to a $C_6$ hydrocarbon refers to all hydrocarbon having 6 carbon atoms, a general reference to pentane includes n-pentane, 2-methylbutane, and 2,2-dimethylpropane, and a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth.

For the purposes of this application, the term or variations of the term "organyl group consisting essentially of inert functional groups" refers to an organyl group (having a free valence on a carbon atom) wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting essentially of inert functional groups" further defines the particular organyl groups that can be present within the organyl group consisting essentially of inert functional groups. Additionally, the term "organyl group consisting essentially of inert functional groups" can refer to the presence of one or more inert functional groups within the organyl group. The term or variation of the term "organyl group consisting essentially of inert functional groups" includes the hydrocarbyl group as a member (among other groups). Similarly, an "organylene group consisting essentially of inert functional groups" refers to an organic group formed by removing two hydrogen atoms from one or two carbon atoms of an organic compound consisting of inert functional groups and an "organic group consisting essentially of inert functional groups" refers to a generalized organic group consisting essentially of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in an $N^2$-phosphinyl amidine can be an inert functional group because a single metal compound cannot complex with both the para ether group and the $N^2$-phosphinyl amidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri, etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

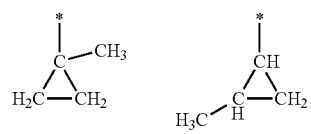

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclopropyl group) and is a member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to hydrocarbon compounds that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. carbon-carbon double bonds can be identified by use of the term "mono," "di," "tri," etc. within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. such multiple bonds can be identified by use of the term "mono," "di," "tri," etc. within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated. The term "linear alpha olefin" as used herein refers to a non-branched alpha olefin having a carbon-carbon double bond between the first and second carbon atom.

The term "normal alpha olefin" whenever used in this specification and claims refers to a linear aliphatic monoolefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon of the methylene group in diphenylmethane; oxygen of diphenyl ether; nitrogen of triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. It should be noted that according the definitions provided herein, general arene groups (including an aryl group and an arylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g., a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "primary carbon atom group," a "secondary carbon atom group," a "tertiary carbon atom group," and a "quaternary carbon atom group" describe the type of carbon atom which would be created when the group is attached to a base structure. A "primary carbon atom group" is a group wherein the carbon atom bonded to the base structure is also bonded to three monovalent atoms (e.g., hydrogen or halides) in addition to the base structure. A methyl group, a trifluormethyl group (among other group) attached to a base structure represent potential "primary carbon atom groups." A "secondary carbon atom group" is a group wherein the carbon atom bonded to the base structure is bonded to one other non-monovalent atom (e.g., carbon, nitrogen, or oxygen, among others) and two monovalent atoms. An ethyl group, a 1-chloroeth-1-yl group, and a methoxymethyl group (among others) attached to a base structure represent potential "secondary carbon atom groups." A "tertiary carbon group" is a group wherein the carbon atom bonded to the base structure is bonded to two other non-monovalent atoms and one monovalent atom. An isopropyl group, a 2-chloroprop-1-yl group, a phenyl group, and a 1-methoxyethy-1-yl group (among others) attached to a base structure represent potential "tertiary carbon groups." A "quaternary carbon group" is a group wherein the carbon atom bonded to the base structure is also bonded to three other non-monovalent atoms. A tert-butyl group and a 2-methoxyprop-2-yl group (among others) attached to a base structure represent potential "quaternary carbon groups."

A "halide" has its usual meaning; therefore, examples of halides include fluoride, chloride, bromide, and iodide.

The terms "room temperature" or "ambient temperature" are used herein to describe any temperature from 15° C. to 35° C. wherein no external heat or cooling source is directly applied. Accordingly, the terms "room temperature" and "ambient temperature" encompass the individual temperatures and any and all ranges, subranges, and combinations of subranges of temperatures from 15° C. to 35° C. wherein no external heating or cooling source is directly applied. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa). References to gaseous, liquid, and/or solid materials refer to the physical state of the material at 25° C. and atmospheric pressure.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4-position and hydrogens located at the 2, 3, 5, and 6 positions. By way of another example, reference to a 3-substituted naphth-2-yl indicates that there is a non-hydrogen substituent located at the 3-position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4-position refers to a group having a non-hydrogen atom at the 4-position and hydrogen or any other non-hydrogen group at the 2-, 3-, 5-, and 6-positions.

The term "reaction zone effluent," and it derivatives (e.g., oligomerization reaction zone effluent) generally refers to all the material which exits the reaction zone. The term "reaction zone effluent," and its derivatives, can also be prefaced with other descriptors that limit the portion of the reaction zone effluent being referenced. For example, the term "reaction zone effluent" refers to all material exiting the reaction zone (e.g., product and solvent or diluent, among others), while the term "olefin reaction zone effluent" refers to only the olefins within the reaction zone effluent and the term "oligomer product reaction zone effluent" refers to oligomer product within the reaction zone effluent.

The term "oligomerization," and its derivatives, refers to processes which produce a mixture of products containing at least 70 weight percent products containing from 2 to 30 ethylene units. Similarly, as used herein an "oligomer" is a product that contains from 2 to 30 ethylene units while an "oligomerization product" or "oligomer product" includes all products made by the process including the "oligomers" and products which are not "oligomers" (e.g., products which contain more than 30 ethylene units). Further the terms "oligomer product" and "oligomerization product" can be used interchangeably.

K value (sometimes referred to as Schulz-Flory chain growth factor, K, or Schulz-Flory K value) can be defined the equation: $K=X_{q+1}/X_q$ wherein $X_{q+1}$ is the number of moles of oligomer product produced having q+1 monomer (e.g., ethylene) units and $X_q$ is the number of moles of oligomer product produced having q monomer (e.g., ethylene) units. Generally, the Schulz-Flory K value can be determined using any two oligomers of the oligomer product which differs in the number of monomer units by 1. However, one would appreciate that product isolation and analysis can lead to inaccuracies in a determined oligomer product distribution using particular oligomers (e.g., incomplete recovery of gaseous product and/or solid product during product isolation). One having ordinary skill in the art would recognize such issues and can choose the appropriate oligomers upon which to base the determination of the Schulz-Flory K value.

Catalyst system productivity is defined as grams of a product produced per gram (or mole) of heteroatomic ligand metal salt complex or heteroatomic ligand in the catalyst system utilized in the oligomerization. Catalyst system activity is defined as grams of a product produced per gram (or mole) of heteroatomic ligand metal salt complex or heteroatomic ligand utilized per unit of time (e.g., hour) of an oligomerization. Catalyst system productivity and/or activity can be stated in terms of various products of an oligomerization and/or components of catalyst system. For example, in an ethylene oligomerization process utilizing a catalyst system comprising an iron salt complex and an organoaluminum compound, the catalyst system productivity which can be utilized include (g oligomer product)/(g Fe), among other productivities.

Unless otherwise specified, the terms "contacted," "combined," and "in the presence of" refer to any addition sequence, order, or concentration for contacting or combining the recited two or more components. The combining or contacting of the components, according to the various methods described herein can occur in one or more contact zones under suitable contact conditions such as temperature, pressure, contact time, flow rates, etc. . . . The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact, unless otherwise specified. The processes can be carried out in a batch or continuous process as is suitable for a given aspect, unless otherwise specified.

Use of the term "optionally" with respect to any element of a claim is intended to mean that the subject element is required, or alternatively, is not required. Both alternatives are intended to be within the scope of the claim.

In this disclosure, a process can have multiple steps or can include features having a number of different elements (e.g., components in a catalyst system or components in an olefin oligomerization process, among other features). These steps and/or elements can be designated utilizing the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

The terms "simultaneously," "simultaneously contact," "contact simultaneously," and their derivatives when referring to a contact method refers to a contact method wherein the two or more recited compounds, mixtures, streams, and/or compositions are contacted by flowing into a common junction, pot, vessel, or reactor, among others, at the same time. The terms "substantially simultaneously," "substantially simultaneously contact," "contact substantially simultaneously," and their derivatives when referring to a contact method refers to a contact method wherein, during the contact of two or more recited compounds, mixtures, streams, and/or compositions, the two or more recited compounds, mixtures, streams, and/or compositions are contacted such that for some period during the contact process the two or more recited compounds, mixtures, streams, and/or compositions flow into a common junction, pot, vessel, or reactor at the same time. It should be noted that the terms "substantially simultaneously," "substantially simultaneously contact," "contact substantially simultaneously," and their derivatives do not mean that the two or more recited compounds, mixtures, streams, and/or compositions are contacted simultaneously over the entire addition of each of the two or more recited compounds, mixtures, streams, and/or compositions. The terms "substantially simultaneously," "substantially simultaneously contact," "contact substantially simultaneously," and it derivatives include scenarios where the flow of one of the (or less than all of the) recited compounds, mixtures, streams, and/or compositions can be initiated into the common junction, pot, vessel, or reactor before the others and/or the flow of one of the (or less than all of the) recited compounds, mixtures, streams, and/or compositions into the common junction, pot, vessel, or reactor can be completed, stopped, or discontinued before the other recited compounds, mixtures, streams, and/or compositions. In any aspect and/or embodiment described herein, the terms "simultaneously," "simultaneously contact," "contact simultaneously," and their derivatives, can be modified by the inclusion of a term providing a quantity of the each of the recited compounds, mixtures, streams, and/or compositions which can be contacted simultaneously indicate scenarios of various degrees of "substantially simultaneously," "substantially simultaneously contact," "contact substantially simultaneously," and their derivatives. For example, at least 20%, 30%, 40%, 50%, 60%, 70%, 75%, 80%, 85%, 90%, 95% of each of the recited compounds, mixtures, streams, and/or compositions can be "simultaneously contacted" or "contacted simultaneously." Generally, the percentages of the recited compounds, mixtures, streams, and/or compositions that can be "simultaneously contacted" or "contacted simultaneously" can be by weight (wt. %), by volume (volume %), or by mole (mole %). Unless otherwise specified, recited compounds, mixtures, streams, and/or compositions that are "substantially simultaneously," "substantially simultaneously contact," "contact substantially simultaneously," and their derivatives shall mean that at least 50% of each of the recited compounds, mixtures, streams, and/or compositions can be "simultaneously contacted" or "contacted simultaneously."

It should be further noted, that in reference to contact method or process, "simultaneously," "simultaneously contact," "contact simultaneously," "substantially simultaneously contact," "contact substantially simultaneously," and their derivatives is different than a process or method wherein one or more a first materials (e.g., compound, mixture, stream, and/or composition) already resides in a pot, vessel, or reactor and one or more other compounds, mixtures, streams, and/or compositions are added to the pot, vessel, or reactor. In this instance the first material in the pot, vessel, or reactor does not flow into the pot, vessel, or reactor concurrently with the other compounds, mixtures, streams, and/or compositions and the material in the pot. Thus, the first material and the other compounds, mixtures, streams, and/or compositions cannot be said to be "simultaneously contacted," "contacted simultaneously," "substantially simultaneously contacted," or "contacted substantially simultaneously." with the other component(s).

Disclosed herein are processes comprising a) introducing into a reaction zone (i) ethylene, (ii) a heteroatomic ligand first metal salt complex, (iii) a second metal salt, and (iv) an organoaluminum compound; and b) forming an oligomer product. In an aspect, the heteroatomic ligand first metal salt complex comprises a heteroatomic ligand complexed to a first metal salt. Also disclosed herein, are processes comprising a) introducing into a reaction zone (i) ethylene, (ii) a heteroatomic ligand, (iii) a metal salt, and (iv) an organoaluminum compound; and b) forming an oligomer product. In some embodiments, these processes can be processes for forming an oligomer product. Further disclosed herein is the use of a metal salt (or second metal salt depending on the particular process) for improving the productivity of any process (e.g., processes for forming an oligomer product) disclosed herein. The processes further can comprise an optional introduction of hydrogen into the reaction zone. The processes further can comprise an optional introduction of an organic reaction medium. In a still further aspect, the organo groups of the organoaluminum compound can be substantially devoid of $\beta,\gamma$-branched organo groups and/or $\beta,\delta$-branched organo groups. Optionally, the ethylene, the heteroatomic ligand first metal salt complex, the heteroatomic ligand, the first metal salt, the metal salt, and hydrogen can be contacted with or in one or more organic reaction medium(s). In an aspect, the oligomer product can be formed at, the reaction zone can have, or the reaction zone can operate at, conditions capable of forming an oligomer product. Generally, the heteroatomic ligand first metal salt complex, the heteroatomic ligand of the heteroatomic ligand first metal salt complex, the first metal salt of the heteroatomic ligand first metal salt complex, the second metal salt, the heteroatomic ligand, the metal salt, the organoaluminum compound, the optional hydrogen, the optional organic reaction medium(s), the reaction zone, the oligomer product, the conditions at which the oligomer product can be formed, the conditions at which the reaction zone can have, and/or the conditions at which the reaction can operate, where applicable, are independent elements of the processes described herein and are independently described herein. These independently described process elements can be utilized in any combination, and without limitation, to further describe the processes provided herein.

Generally, the heteroatomic ligand and metal salt or the heteroatomic ligand first metal salt complex can be any heteroatomic ligand and metal salt or any heteroatomic ligand first metal salt complex that when contacted with ethylene as disclosed herein can form an oligomer product. In an aspect, the processes described herein utilize a heteroatomic ligand first metal salt complex; or alternatively, a heteroatomic ligand and a metal salt. In an aspect, the heteroatomic ligand or the heteroatomic ligand of the heteroatomic ligand first metal salt complex can comprise a bidentate metal salt complexing moiety or a tridentate metal salt complexing moiety; alternatively, a bidentate metal salt complexing moiety; or alternatively, a tridentate metal salt complexing moiety. In an embodiment, the heteroatomic ligand or the heteroatomic ligand of the heteroatomic ligand first metal salt complex can comprise at least one metal salt complexing moiety; alternatively, one or two metal salt complexing moieties; alternatively, one metal salt complexing moiety; or alternatively, two metal salt complexing moieties.

In an aspect, each metal salt complexing moiety of the heteroatomic ligand or the heteroatomic ligand of the heteroatomic ligand first metal salt complex, can comprise at least two metal salt complexing groups selected from the group consisting of an imine group and an aromatic nitrogen atom containing group. In some embodiments, each metal salt complexing moiety of the heteroatomic ligand or the heteroatomic ligand of the heteroatomic ligand first metal salt complex, can comprise at least two imine metal salt complexing group, at least two imine complexing groups and an aromatic nitrogen atom containing group, or an imine group and an aromatic nitrogen atom containing group; alternatively, at least two imine metal salt complexing group; alternatively, at least two imine complexing groups and an aromatic nitrogen atom containing group; or alternatively, an imine group and an aromatic nitrogen atom containing group. Generally, the aromatic nitrogen atom containing group of any metal salt complexing moiety of the heteroatomic ligand or the heteroatomic ligand of the heteroatomic ligand first metal salt complex can be a pyrrole group, a pyridine group, a bipyridine (2,2'-bipyridine) group, or a phenanthroline group; alternatively, a pyridine group, a bipyridine (2,2'-bipyridine) group, or a phenanthroline group; alternatively, a pyridine group or a phenanthroline group; alternatively, a pyridine group; alternatively, a bipyridine (2,2'-bipyridine) group; or alternatively, a phenanthroline group. In an embodiment, the pyrrole group, pyridine group, bipyridine (2,2'-bipyridine) group, or phenanthroline group can be unsubstituted or substituted; alternatively, unsubstituted; or alternatively, substituted. Each substituent of a substituted pyrrole group, a substituted pyridine group, a substituted bipyridine (2,2'-bipyridine) group, or a substituted phenanthroline group independently can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe a substituted pyrrole group, a substituted pyridine group, a substituted bipyridine (2,2'-bipyridine) group, or a substituted phenanthroline group.

In an aspect, the heteroatomic ligand or the heteroatomic ligand of the heteroatomic ligand first metal salt complex can be an α-diimine, a pyridine bisimine, a phenanthroline imine, or any combination thereof; alternatively, an α-diimine or a pyridine bisimine; alternatively, an α-diimine; alternatively, a pyridine bisimine; or alternatively, a phenanthroline imine. In some embodiments, the heteroatomic ligand first metal salt complex can be an α-diimine first metal salt complex, a pyridine bisimine first metal salt complex, a phenanthroline imine first metal salt complex, or any combination thereof; alternatively, an α-diimine first metal salt complex; alternatively, a pyridine bisimine first metal salt complex; or alternatively, a phenanthroline imine first metal salt complex. Generally, the α-diimine, the pyridine bisimine, the phenanthroline imine, the α-diimine first metal salt complex, the pyridine bisimine first metal salt complex, and the phenanthroline imine first metal salt complex are independent elements of any respective processes described herein in which they are utilized and are independently described herein. These independently described elements can be utilized in any combination, and without limitation, to further describe the processes which utilize these independent elements.

In various aspects and embodiments, an α-diimine and a metal salt, or an α-diimine first metal salt complex, can be utilized in the processes described herein. Generally, the α-diimine, or the α-diimine of the α-diimine first metal salt complex disclosed herein, can be any α-diimine, or any α-diimine of the α-diimine first metal salt complex disclosed herein, that when contacted with the other materials of the processes described herein (e.g., metal salt, ethylene, organoaluminum compound and/or any other appropriate reagent(s)), under the appropriate conditions, can form an oligomer product. Generally, the α-diimine and the metal salt (or the α-diimine and the first metal salt of the α-diimine first metal salt complex) are independent elements of the processes described herein and are independently disclosed herein. The independent descriptions of the α-diimine and the metal salt (or the α-diimine and the first metal salt of the α-diimine first metal salt complex) can be used without limitation, and in any combination, to further describe the processes that can be utilized in the aspects and/or embodiments of the processes described herein. In an aspect, the α-diimine (or the α-diimine of the α-diimine first metal salt complex) can comprise only one α-diimine group; alternatively, at least two α-diimine groups; or alternatively, the α-diimine can comprise only two α-diimine groups.

Generally, the α-diimine or the α-diimine of the α-diimine first metal salt complex can be described as comprising i) an α-diimine group, ii) a first imine nitrogen group attached to a first imine nitrogen atom of the α-diimine group, and iii) a second imine nitrogen group attached to a second imine nitrogen atom of the α-diimine group. The α-diimine group, first imine nitrogen group, and second imine nitrogen group are independent elements of the α-diimine or the α-diimine of the α-diimine first metal salt complex and each of these elements are independently described herein. The independent elements of the α-diimine or the α-diimine of the α-diimine first metal salt complex can used without limitation, and in any combination, to further describe the α-diimine or the α-diimine of the α-diimine first metal salt complex.

In an aspect, the α-diimine (or the α-diimine of the α-diimine first metal salt complex) can be a bidentate α-diimine or a tridentate α-diimine; alternatively, a bidentate α-diimine; or alternatively, a tridentate α-diimine. It should be noted that the tridentate α-diimine description does not necessarily imply that all of the ligating elements of the tridentate α-diimine complex to the metal salt.

In an aspect, the α-diimine group of the α-diimine (or the α-diimine of the α-diimine first metal salt complex) can be derived from an α-diacyl compound; or alternatively, an α-dione. Consequently, in some aspects, the α-diimine (or the α-diimine of the α-diimine first metal salt complex) can be described as comprising i) an α-diimine group derived from an α-diacyl compound, ii) a first imine nitrogen group attached to a first imine nitrogen atom of the α-diimine group, and iii) a second imine nitrogen group attached to a second imine nitrogen atom of the α-diimine group; or alternatively, the α-diimine (or the α-diimine of the α-diimine first metal salt complex) can be described as comprising i) an α-diimine group derived from an α-dione, ii) a first imine nitrogen group attached to a first imine nitrogen atom of the α-diimine group, and iii) a second imine nitrogen group attached to a second imine nitrogen atom of the α-diimine group. In an aspect, the α-diacyl compound (or α-dione) can be an aliphatic α-diacyl compound (or aliphatic α-dione) or an aromatic α-diacyl compound (or aromatic α-dione); alternatively, an aliphatic α-diacyl compound (or aliphatic α-dione); or alternatively, an aromatic α-diacyl compound (or aromatic α-dione). In other aspects, the α-diacyl compound (or α-dione), whether it is aliphatic or aromatic, can be a cyclic α-diacyl compound (or cyclic α-dione) or an acyclic α-diacyl compound (or acyclic α-dione); alternatively, a cyclic α-diacyl compound (or cyclic α-dione); or alternatively, an acyclic α-diacyl compound (or acyclic α-dione). In any aspect or embodiment disclosed herein, the α-diacyl compound (or α-dione), whether it is aliphatic or aromatic and/or cyclic or acyclic, can be a $C_4$ to $C_{60}$ α-diacyl compound (or $C_4$ to $C_{60}$ α-dione), a $C_4$ to $C_{45}$ α-diacyl compound (or $C_4$ to $C_{45}$ α-dione), a $C_4$ to $C_{30}$ α-diacyl compound (or $C_4$ to $C_{30}$ α-dione), or $C_4$ to $C_{20}$ α-diacyl compound (or $C_4$ to $C_{20}$ α-dione).

Generally, the α-dione can have the structure $R^{k1}$—C(=O)—C(=O)—$R^{k2}$. In an aspect, $R^{k1}$ and $R^{k2}$ independently can be an organyl group; alternatively, an organyl group consisting essentially of inert functional groups; or alternatively, a hydrocarbyl group. In any aspect or embodiment disclosed herein, the organyl groups which can be utilized as $R^{k1}$ and/or $R^{k2}$ can be a $C_1$ to $C_{30}$, a $C_1$ to $C_{20}$, a $C_1$ to $C_{15}$, a $C_1$ to $C_{10}$, or a $C_1$ to $C_5$ organyl group. In any aspect or embodiment disclosed herein, the organyl groups consisting essentially of inert functional groups which can be utilized as $R^{k1}$ and/or $R^{k2}$ independently can be a $C_1$ to $C_{30}$, a $C_1$ to $C_{20}$, a $C_1$ to $C_{15}$, a $C_1$ to $C_{10}$, or a $C_1$ to $C_5$ organyl group consisting essentially of inert functional groups. In any aspect or embodiment disclosed herein, the hydrocarbyl groups which can be utilized as $R^{k1}$ and/or $R^{k2}$ independently can be a $C_1$ to $C_{30}$, a $C_1$ to $C_{20}$, a $C_1$ to $C_{15}$, a $C_1$ to $C_{10}$, or a $C_1$ to $C_5$ hydrocarbyl group.

In an aspect, the α-dione from which the α-diimine group (or the α-diimine of the α-diimine first metal salt complex) can be derived can be an acyclic α-dione, a semicyclic α-dione, or a cyclic α-dione; alternatively, an acyclic α-dione; alternatively, a semicyclic α-dione; or alternatively, a cyclic α-dione. When the α-dione is an acyclic α-dione, both $R^{k1}$ and $R^{k2}$ are acyclic. When the α-dione is a semicyclic α-dione, $R^{k1}$ and/or $R^{k2}$ are or can comprise a cyclic structure wherein $R^{k1}$ and $R^{k2}$ are not connected to form a ring or ring system containing both ketone carbon atoms of the α-dione group. When the α-dione is a cyclic α-dione, $R^{k1}$ and $R^{k2}$ are connected to form a ring or ring system containing both ketone carbon atoms of the α-dione group. In some semi-cyclic and/or cyclic α-dione aspects, the ring or ring system(s) can be saturated. In other semi-cyclic and/or cyclic α-dione aspects, the ring or ring system(s) can contain carbon-carbon double (and/or triple) bonds. In further semi-cyclic and/or cyclic α-dione aspects, the ring or ring system(s) can be a bicyclic ring system. In yet other semi-cyclic and/or cyclic α-dione aspects, the ring or ring system(s) can comprise an aromatic ring or an aromatic ring system.

In an acyclic α-dione aspect, the α-dione can be 2,3-butanedione, a substituted 2,3-butanedione, 2,3-pentanedione, a substituted 2,3-pentanedione, 2,3-hexanedione, a substituted 2,3-hexanedione, 3,4-hexanedione, or a substituted 3,4-hexanedione. In some aspects, the α-dione can be 2,3-butanedione, 2,3-pentanedione, 2,3-hexanedione, or 3,4-hexanedione. In further aspects, the α-dione can be 2,3-butanedione; alternatively, 2,3-pentanedione; alternatively, 2,3-hexanedione; or alternatively, 3,4-hexanedione.

In an aromatic semi-cyclic α-dione aspect, the α-dione can be benzil or a substituted benzil. In other aspects, the α-dione can be benzil.

In a saturated cyclic α-dione aspect, the α-dione can be 1,2-cyclobutanedione, a substituted 1,2-cyclobutanedione, 1,2-cyclopentanedione, a substituted 1,2-cyclopentanedione, 1,2-cyclohexanedione, a substituted 1,2-cyclohexanedione, 1,2-cycloheptanedione, or a substituted 1,2-cycloheptanedione. In some saturated cyclic α-dione aspects, the α-dione can be 1,2-cyclopentanedione, a substituted 1,2-cyclopentanedione, 1,2-cyclohexanedione, or a substituted 1,2-cyclohexanedione. In some saturated cyclic α-dione aspects, the α-dione can be 1,2-cyclopentanedione, or 1,2-cyclohexanedione. In yet other aspects, the α-dione can be 1,2-cyclopentanedione; or alternatively, 1,2-cyclohexanedione.

In saturated ring system α-dione aspects, the α-dione can be bicyclo[2.2.1]hepta-1,2-dione, a substituted bicyclo[2.2.1]hepta-1,2-dione, bicyclo[2.2.2]octa-1,2-dione, a substituted bicyclo[2.2.2]octa-1,2-dione, or camphorquinone. In some saturated ring system aspects, the α-dione can be bicyclo[2.2.1]hepta-1,2-dione, bicyclo[2.2.2]octa-1,2-dione, or camphorquinone. In yet other saturated ring system α-dione aspects, the α-dione can be camphorquinone.

In unsaturated cyclic α-dione aspects, the α-dione can be 1,2-benzoquinone, a substituted 1,2-benzoquinone, cyclohex-3-ene-1,2-dione, a substituted cyclohex-3-ene-1,2-dione, cyclopent-3-ene-1,2-dione, a substituted cyclopent-3-ene-1,2-dione, cyclohex-4-ene-1,2-dione, a substituted cyclohex-4-ene-1,2-dione, 3,4-dihydro-1,2-naphthoquinone, a substituted 3,4-dihydro-1,2-naphtha-quinone, 1,4-dihydronaphthoquinone, or a substituted 1,4-dihydronaphthoquinone. In some unsaturated cyclic α-dione aspects, the α-dione can be 1,2-benzoquinone, cyclohex-3-ene-1,2-dione, cyclopent-3-ene-1,2-dione, cyclohex-4-ene-1,2-dione, 3,4-dihydronaphthoquinone, or 1,4-dihydronaphthoquinone. In other unsaturated cyclic α-dione aspects, the α-dione can be 1,2-benzoquinone; alternatively, 3,4-dihydronaphthoquinone; or alternatively, 1,4-dihydronaphthanoquinone.

In aromatic ring system α-dione aspects, the α-dione can be a 1,2-naphthoquinone, a substituted 1,2-naphthoquinone, 2,3-naphthoquinone, a substituted 2,3-naphthoquinone, acenaphthenequinone, a substituted acenaphthenequinone, phenanthrenequinone, a substituted phenanthrenequinone, pyrenequinone, or a substituted pyrenequinone. In some aromatic ring system α-dione aspects, the α-dione can be 1,2-naphthoquinone, 2,3-naphthoquinone, acenaphthenequinone, phenanthrenequinone, or pyrenequinone. In other aromatic ring system α-dione aspects, the α-dione can be acenaphthenequinone, phenanthrenequinone, or pyrenequinone. In yet other aromatic ring system α-dione aspects, the α-dione can be 1,2-naphthoquinone; alternatively, 2,3-naphthoquinone; alternatively, acenaphthenequinone; alternatively, phenanthrenequinone; or alternatively, pyrenequinone.

Within any substituted α-dione aspects, each substituent independently can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe the substituent of any substituted α-dione described herein.

In an aspect, the first imine group attached to the first imine nitrogen atom (first imine group for short) and/or second imine group attached to the second imine nitrogen atom (second imine group for short) of the α-diimine independently can be an organyl group; alternatively, an organyl group consisting essentially of inert functional groups; or alternatively, a hydrocarbyl group.

Generally, a bidentate α-diimine will have a first imine group and a second imine group which can be independently selected from an organyl group consisting essentially of inert functional groups (or a hydrocarbyl group). Thus, when the α-diimine is a bidentate α-diimine, the bidentate α-diimine can comprise i) an α-diimine group, ii) a first imine nitrogen group consisting of an organyl group consisting essentially of inert functional groups (or a hydrocarbyl group) attached to a first imine nitrogen atom of the α-diimine group and iii) a second imine nitrogen group consisting of an organyl group consisting essentially of inert functional groups (or a hydrocarbyl group) attached to a second imine nitrogen atom of the α-diimine group.

Generally, a tridentate α-diimine will have a first imine group selected from an organyl group consisting essentially of inert functional groups (or a hydrocarbyl group) while the second imine group is an organyl group. When the α-diimine is a tridentate α-diimine, the organyl group which is the second imine group can be described as a second imine group comprising (1) a metal salt complexing group (or a first metal salt complexing group for the α-diimine first metal salt complex) and (2) a linking group linking the metal salt complexing group (or the first metal salt complexing group for the α-diimine first metal salt complex) to a second imine nitrogen atom of the α-diimine group. Thus, in some aspects, the tridentate α-diimine can comprise i) an α-diimine group, ii) a first imine nitrogen group consisting of an organyl group consisting essentially of inert functional groups (or a hydrocarbyl group) attached to a first imine nitrogen atom of the α-diimine group, and iii) a second imine nitrogen group comprising (1) a metal salt complexing group (or the first metal salt complexing group for the α-diimine first metal salt complex) and (2) a linking group linking the metal salt complexing group (or the first metal salt complexing group for the α-diimine first metal salt complex) to a second imine nitrogen atom of the α-diimine group. The metal salt complexing group and the linking group (or the first metal salt complexing group and the linking group for the α-diimine first metal salt complex) of the second imine group comprising (1) a metal salt complexing group (or the first metal salt complexing group for the α-diimine first metal salt complex) and (2) a linking group linking the metal salt complexing group or the first metal salt complexing group for the α-diimine first metal salt complex) to a second imine nitrogen atom of the α-diimine group are independent elements of the second imine group and are independently described herein. The independent description of the metal salt complexing group (or the first metal salt complexing group for the α-diimine first metal salt complex) and the linking group can be used without limitation and in any combination to further describe the second imine group comprising (1) a metal salt complexing group (or the first metal salt complexing group for the α-diimine first metal salt complex) and (2) a linking group linking the metal salt complexing group or the first metal salt complexing group for the α-diimine first metal salt complex) to a second imine nitrogen atom of the α-diimine group of an α-diimine.

In any aspect and/or embodiment disclosed herein, the organyl groups which can be utilized as the first and/or second imine organyl groups independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the organyl groups consisting essentially of inert functional groups which can be utilized as the first and/or second imine organyl groups consisting essentially of inert functional groups independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the hydrocarbyl groups which can be utilized as the first and/or second imine hydrocarbyl groups independently can be a $C_1$ to $C_{20}$, a $C_1$ to $C_{15}$, a $C_1$ to $C_{10}$, or a $C_1$ to $C_5$ hydrocarbyl group. Generally, the first imine group and the second imine group independently can be saturated or unsaturated, linear or branched, acyclic or cyclic, and/or aromatic or heteroaromatic. In other aspects, the first imine group and/or second imine group, can be a primary, a secondary, a tertiary, or a quaternary group; alternatively, a primary group; alternatively, a secondary group; alternatively, a tertiary group; or alternatively, a quaternary group. One skilled in the art will readily recognize which imine nitrogen groups belong to the primary, secondary, tertiary, or quaternary imine nitrogen group classes.

In an aspect, the first imine group and/or second imine group independently can be an alkyl group, a substituted alkyl group, a cycloalkyl group, a substituted cycloalkyl group, an aryl group, or a substituted aryl group. In some aspects, the first imine group and/or second imine group independently can be an alkyl group or a substituted alkyl group; alternatively, a cycloalkyl group or a substituted cycloalkyl group; alternatively, an aryl group or a substituted aryl group; or alternatively, an alkyl group, a cycloalkyl group, or an aryl group. In other aspects, the first imine group and/or second imine group independently can be an alkyl group; alternatively, a substituted alkyl group, alternatively, a cycloalkyl group; alternatively, a substituted cycloalkyl group; alternatively, an aryl group; or alternatively, a substituted aryl group. In any aspect and/or embodiment disclosed herein, the alkyl group which can be utilized as the first imine group and/or second imine group can be a $C_1$ to $C_{20}$, a $C_1$ to $C_{10}$, or a $C_1$ to $C_5$ alkyl group. In any aspect and/or embodiment disclosed herein, the substituted alkyl group which can be utilized as the first imine group and/or second imine group can be a $C_1$ to $C_{20}$, a $C_1$ to $C_{10}$, or a $C_1$ to $C_5$ substituted alkyl group. In any aspect and/or embodiment disclosed herein, the cycloalkyl group which can be utilized as the first imine group and/or second imine group can be a $C_4$ to $C_{20}$, a $C_4$ to $C_{15}$, or a $C_4$ to $C_{10}$ cycloalkyl group. In any aspect and/or embodiment disclosed herein, the substituted cycloalkyl group which can be utilized as the first imine group and/or second imine group can be a $C_4$ to $C_{20}$, a $C_4$ to $C_{15}$, or a $C_4$ to $C_{10}$ substituted cycloalkyl group. In any aspect and/or embodiment disclosed herein, the aryl group which can be utilized as the first imine group and/or second imine group can be a $C_6$ to $C_{20}$, a $C_6$ to $C_{15}$, or a $C_6$ to $C_{10}$ aryl group. In any aspect and/or embodiment disclosed herein, the substituted aryl group which can be utilized as the first imine group and/or second imine group can be a $C_6$ to $C_{20}$, a $C_6$ to $C_{15}$, or a $C_6$ to $C_{10}$ substituted aryl group. Each substituent of a substituted alkyl group (general or specific), a substituted cycloalkyl group (general or specific), a substituted aryl group (general or specific), and/or substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe the first imine group and/or second imine group.

In an aspect, the first imine nitrogen group and/or the second imine nitrogen group independently can be a methyl group, an ethyl group, a propyl group, a butyl group, or a pentyl group. In some aspects, the first imine nitrogen group and/or the second imine nitrogen group independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group. In some aspects, the alkyl groups which can be utilized as the first imine nitrogen group and/or the second imine nitrogen group can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as the first imine nitrogen group and/or the second imine nitrogen group.

In an aspect, the first imine nitrogen group and/or the second imine nitrogen group can be a cyclopentyl group, a substituted cyclopentyl group, a cyclohexyl group, a substituted cyclohexyl group, an adamantyl group, or a substituted adamantyl group; alternatively, a cyclopentyl group or a substituted cyclopentyl group; alternatively, a cyclohexyl group or a substituted cyclohexyl group; alternatively, an adamantyl group or a substituted adamantyl group; alternatively, a cyclopentyl group; alternatively, a substituted cyclopentyl group; alternatively, a cyclohexyl group; alternatively, a substituted cyclohexyl group; alternatively, an adamantyl group; or alternatively, a substituted adamantyl group. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as the first imine nitrogen group and/or the second imine nitrogen group.

In an aspect, the first imine nitrogen group and/or the second imine nitrogen group can be a phenyl group, a substituted phenyl group, a naphthyl group, or a substituted naphthyl group; alternatively, a phenyl group or a substituted phenyl group; alternatively, a naphthyl group, or a substituted naphthyl group; alternatively, a phenyl group; alternatively, a substituted phenyl group; alternatively, a naphthyl group; or alternatively, a substituted naphthyl group. In an aspect, each substituted phenyl group which can be the first imine nitrogen group and/or the second imine nitrogen group can comprise a substituent at the 2-position, a substituent at the 3-position, a substituent at the 4-position, substituents at the 2- and 3-positions, substituents at the 2- and 4-positions, substituents at the 2- and 5-positions, substituents at the 3- and 5-positions, substituents at the 2- and 6-positions, or substituents at the 2-, 4-, and 6-positions; alternatively, a substituent at the 2-position, a substituent at the 4-position, substituents at the 2- and 4-positions, substituents at the 2- and 6-positions, or substituents at the 2-, 4-, and 6-positions; alternatively, substituents at the 2- and 6-positions or substituents at the 2-, 4-, and 6-positions; alternatively, a substituent at the 2-position; alternatively, a substituent at the 3-position; alternatively, a substituent at the 4-position; alternatively, substituents at the 2- and 3-positions; alternatively, substituents at the 2- and 4-positions; alternatively, substituents at the 2- and 5-positions; alternatively, substituents at the 3- and 5-positions; alternatively, substituents at the 2- and 6-positions; or alternatively, substituents at the 2-, 4-, and 6-positions. In some aspects, the substituted phenyl group, which can be utilized as the first imine nitrogen group and/or the second imine nitrogen group, can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubstituted phenyl group. In an aspect, one or more substituents of a multi-substituted phenyl group utilized as the first imine nitrogen group and/or the second imine nitrogen group can be the same or different; alternatively, all the substituents of a multi-substituted phenyl group can be the same; or alternatively, all the substituents of a multi-substituted phenyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as the first imine nitrogen group and/or the second imine nitrogen group.

In a non-limiting aspect, the substituted phenyl group, which can be utilized as the first imine nitrogen group and/or the second imine nitrogen group can be a 2-alkylphenyl group, a 3-alkylphenyl group, a 4-alkylphenyl group, a 2,3-dialkylphenyl group, a 2,4-dialkylphenyl group, a 2,5-dialkylphenyl group, a 3,5-dialkylphenyl group, a 2,6-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2,6-dialkylphenyl group, or a 2,4,6-trialkylphenyl group; alternatively, a 2-alkylphenyl group; alternatively, a 4-alkylphenyl group; alternatively, a 2,3-dialkylphenyl group; alternatively, a 2,4-dialkylphenyl group; alternatively, a 2,5-dialkylphenyl group; alternatively, a 3,5-dialkylphenyl group; alternatively, a 2,6-dialkylphenyl group; or alternatively, a 2,4,6-trialkylphenyl group. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. Alkyl substituent groups (general and specific) are independently described herein and these alkyl substituent groups can be utilized, without limitation, to further describe any alkyl substituted phenyl group which can be utilized as the first imine nitrogen group and/or the second imine nitrogen group. In some non-limiting aspects, the substituted phenyl groups which can be the first imine nitrogen group and/or the second imine nitrogen group can be a 2,6-dimethylphenyl group, a 2,6-diethylphenyl group, a 2,6-diisopropylphenyl group, or a 2,5-di-tert-butylphenyl group, a 2-isopropyl-6-methylphenyl group, a 2,4,6-trimethylphenyl group, a 2,6-dimethyl-4-(tert-butyl)phenyl group, 2,6-dimethyl-4-(2,2-dimethylbenzyl)phenyl group, a 2,6-dimethyl-4-(1,1-diphenylethyl)phenyl group, or a 2,6-dimethyl-4-(1,1,3,3-tetramethylbutyl)phenyl group; alternatively, a 2,6-dimethylphenyl group, a 2,6-diethylphenyl group, or a 2,6-diisopropylphenyl group; alternatively, a 2,6-dimethylphenyl group or a 2,4,6-trimethylphenyl group; alternatively, a 2,6-dimethylphenyl group; alternatively, a 2,6-diethylphenyl group; alternatively, a 2,6-diisopropylphenyl group; alternatively, a 2,5-di-tert-butylphenyl group; alternatively, a 2-isopropyl-6-methylphenyl group; alternatively, a 2,4,6-trimethylphenyl group; or alternatively, a 2,6-dimethyl-4-(1,1,3,3-tetramethylbutyl)phenyl group.

In tridentate α-diimine aspects, the second imine nitrogen group can comprise (1) a metal salt complexing group (or the first metal salt complexing group for the α-diimine first metal salt complex) and (2) a linking group linking the metal salt complexing group (or the first metal salt complexing group for the α-diimine first metal salt complex) to a second imine nitrogen atom of the α-diimine group. Generally, the metal salt complexing group (or the first metal salt complexing group for the α-diimine first metal salt complex) and the linking group linking the metal salt complexing group (or the first metal salt complexing group for the α-diimine first metal salt complex) to the second imine nitrogen atom of the α-diimine group are independent elements of the second imine group and are independently described herein. The independent descriptions of the metal salt complexing group (or the first metal salt complexing group for the α-diimine first metal salt complex) and the linking group can be used without limitation, and in any combination, to further describe the second imine group comprising (1) a metal salt complexing group (or the first metal salt complexing group for the α-diimine first metal salt complex) and (2) a linking group linking the metal salt complexing group (e.g. the first metal salt complexing group for the α-diimine first metal salt complex) to a second imine nitrogen atom of the α-diimine group of an α-diimine.

Generally, the metal salt complexing group (or the first metal salt complexing group for the α-diimine first metal salt complex) can be any group comprising a heteroatom capable of complexing with the metal salt (or the first metal salt for the α-diimine first metal salt complex) and the linking group can be any group capable of linking the metal salt complexing group (or the first metal salt complexing group for the α-diimine first metal salt complex) to the second imine nitrogen atom of the α-diimine group. The linking group includes all atoms between the second imine nitrogen atom and the metal salt complexing group (or the first metal salt complexing group for the α-diimine first metal salt complex). If the metal salt complexing group (or the first metal salt complexing group for the α-diimine first metal salt complex) is acyclic, the linking group includes all atoms between the second imine nitrogen atom and the heteroatom of the metal salt complexing (or the first metal salt complexing group for the α-diimine first metal salt complex) functional group. For example, in an N,N'-dimethylethylene group, the linking group is —CH$_2$CH$_2$— and the metal salt complexing group (or the first metal salt complexing group for the α-diimine first metal salt complex) is the N,N'-dimethylaminyl group, while in a 2-phenoxyethyl group the linking group is —CH$_2$CH$_2$— and the metal salt complexing group (or the first metal salt complexing group for the α-diimine first metal salt complex) is the phenoxy group. However, if the heteroatom of the metal salt complexing group (or the first metal salt complexing group for the α-diimine first metal salt complex) is contained within a ring, the linking group includes all the atoms between the second imine nitrogen atom and the first atom within the ring containing the metal salt (or the first metal salt for the α-diimine first metal salt complex) complexing heteroatom of the metal salt complexing group (or the first metal salt complexing group for the α-diimine first metal salt complex). For example, in a 2-ethylpyridinyl group the linking group is —CH$_2$CH$_2$— and the metal salt complexing group (or the first metal salt complexing group for the α-diimine first metal salt complex) is the 2-pyridinyl group, while in 1-ethylpiperidinyl group the linking group is —CH$_2$CH$_2$— and the metal salt complexing group (or the first metal salt complexing group for the α-diimine first metal salt complex) is the 1-piperidinyl group.

The metal salt complexing group (or the first metal salt complexing group for the α-diimine first metal salt complex) can be any group comprising a heteroatom capable of complexing with the metal salt (or the first metal salt for the α-diimine first metal salt complex). In an aspect, the metal salt complexing group (or the first metal salt complexing group for the α-diimine first metal salt complex) can be a $C_2$ to $C_{30}$ group comprising a heteroatom, a $C_2$ to $C_{20}$ group comprising a heteroatom, a $C_2$ to $C_{10}$ group comprising a heteroatom, or a $C_2$ to $C_5$ group comprising a heteroatom wherein the heteroatom is capable of complexing with the metal salt (or the first metal salt for the α-diimine first metal salt complex). In some aspects, the metal salt complexing heteroatom (or the first metal salt complexing heteroatom for the α-diimine first metal salt complex) of the metal salt complexing group (or the first metal salt complexing group for the α-diimine first metal salt complex) can be an oxygen, sulfur, nitrogen, or phosphorus; alternatively, oxygen or sulfur; or alternatively, nitrogen or phosphorus. In other aspects, the metal salt complexing heteroatom (or the first metal salt complexing heteroatom for the α-diimine first metal salt complex) of the metal salt complexing group (or the first metal salt complexing group for the α-diimine first metal salt complex) can be oxygen; alternatively, sulfur; alternatively, nitrogen; or alternatively, phosphorus. Optionally, the metal salt complexing group (or the first metal salt complexing group for the α-diimine first metal salt complex) can contain additional heteroatoms which do not complex the metal salt (or the first metal salt for the α-diimine first metal salt complex) in the α-diimine metal salt complex (or the α-diimine first metal salt complex) such as inert heteroatoms (e.g. halides and silicon) and/or additional metal salt complexing heteroatom(s) (or the first metal salt complexing heteroatom(s) for the α-diimine first metal salt complex) which do not complex with the metal salt (or the first metal salt for the α-diimine first metal salt complex).

In an aspect, the metal salt complexing group (or the first metal salt complexing group for the α-diimine first metal salt complex) can be a dihydrocarbyl aminyl group, a di(substituted hydrocarbyl) aminyl group, a dihydrocarbyl phosphinyl group, a di(substituted hydrocarbyl) phosphinyl group, a hydrocarbyl etheryl group, a substituted hydrocarbyl etheryl group, a hydrocarbyl sulfidyl group, a substituted hydrocarbyl sulfidyl group, a furanyl group, a substituted furanyl group, a tetrahydrofuranyl group, a substituted tetrahydrofuranyl group, a pyridinyl group, a substituted pyridinyl group, a morphilinyl group, a substituted morphilinyl group, a pyrrolyl group, a substituted pyrrolyl group, a pyrrolidinyl group, a substituted pyrrolidinyl group, a piperidinyl group, or a substituted piperidinyl group. In some aspects, the metal salt complexing group (or the first metal salt for the α-diimine first metal salt complex) can be a dihydrocarbyl aminyl group or a di(substituted hydrocarbyl) aminyl group; alternatively, a dihydrocarbyl phosphinyl group or a di(substituted hydrocarbyl) phosphinyl group; alternatively, a hydrocarbyl etheryl group or a substituted hydrocarbyl etheryl group; or alternatively, a hydrocarbyl sulfidyl group or a hydrocarbyl sulfidyl group. In other aspects, the metal salt complexing group (or the first metal salt complexing group for the α-diimine first metal salt complex) can be a dihydrocarbyl aminyl group; alternatively, a di(substituted hydrocarbyl) aminyl group; alternatively, a dihydrocarbyl phosphinyl group; or alternatively, a di(substituted hydrocarbyl) phosphinyl group. Each substituent of a substituted metal salt complexing group (or a first metal salt complexing group for the α-diimine first metal salt complex) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted metal salt complexing group (or a substituted first metal salt complexing group for the α-diimine first metal salt complex).

Each hydrocarbyl group of any metal salt complexing group (or any first metal salt complexing group for the α-diimine first metal salt complex) having a hydrocarbyl group disclosed herein independently can be a $C_1$ to $C_{20}$, a $C_1$ to $C_{15}$, a $C_1$ to $C_{10}$, or a $C_1$ to $C_5$ hydrocarbyl group while each substituted hydrocarbyl group of a metal salt complexing group (or a first metal salt complexing group for the α-diimine first metal salt complex) having a substituted hydrocarbyl group disclosed herein independently can be a $C_1$ to $C_{20}$, a $C_1$ to $C_{15}$, a $C_1$ to $C_{10}$, or a $C_1$ to $C_5$ substituted hydrocarbyl group. In an aspect, each hydrocarbyl/substituted hydrocarbyl group of a metal salt complexing group (or the first metal salt complexing group for the α-diimine first metal salt complex) having a hydrocarbyl/substituted hydrocarbyl group described herein independently can be an alkyl group, a substituted alkyl group, a cycloalkyl group, a substituted cycloalkyl group, an aryl group, or a substituted aryl group; alternatively, an alkyl group or a substituted alkyl group; alternatively, a cycloalkyl group or a substituted cycloalkyl group; alternatively, an aryl group or a substituted aryl group; alternatively, an alkyl group, a cycloalkyl group, or an aryl group; alternatively, an alkyl group; alternatively, a substituted alkyl group; alternatively, a cycloalkyl group; alternatively, a substituted cycloalkyl group; alternatively, an aryl group; or alternatively, a substituted aryl group. Each substituent of a substituted alkyl group (general or specific), a substituted cycloalkyl group (general or specific), a substituted aryl group (general or specific), and/or a substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted metal salt complexing group (or the substituted first metal salt complexing group for the α-diimine first metal salt complex).

In any aspect and/or embodiment disclosed herein, the alkyl group of any metal salt complexing group (or the first metal salt complexing group for the α-diimine first metal salt complex) having an alkyl group disclosed herein independently can be a $C_1$ to $C_{20}$, a $C_1$ to $C_{10}$, or a $C_1$ to $C_5$ alkyl group while the substituted alkyl group of any metal salt complexing group (or any first metal salt complexing group for the α-diimine first metal salt complex) having a substituted alkyl group disclosed herein independently can be a $C_1$ to $C_{20}$, a $C_1$ to $C_{10}$, or a $C_1$ to $C_5$ substituted alkyl group. In an aspect, the alkyl group of any metal salt complexing group (or the first metal salt complexing group for the α-diimine first metal salt complex) having an alkyl group disclosed herein independently can be a methyl group, an ethyl group, a propyl group, a butyl group, or a pentyl group. In some aspects, the alkyl group of any metal salt complexing group (or the first metal salt complexing group for the α-diimine first metal salt complex) having an alkyl group disclosed herein independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group. In some aspects, the alkyl groups which can be utilized as the alkyl group of any metal salt complexing group (or any first metal salt complexing group for the α-diimine first metal salt complex) having an alkyl group disclosed herein can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as the substituted alkyl group of a metal salt complexing group (or a first metal salt complexing group for the α-diimine first metal salt complex).

In any aspect or embodiment disclosed herein, the cycloalkyl group of any metal salt complexing group (or any first metal salt complexing group for the α-diimine first metal salt complex) having a cycloalkyl group disclosed herein independently can be a $C_4$ to $C_{20}$, a $C_4$ to $C_{15}$, or a $C_4$ to $C_{10}$ cycloalkyl group while the substituted cycloalkyl group of any metal salt complexing group (or any first metal salt complexing group for the α-diimine first metal salt complex) having a substituted cycloalkyl group disclosed herein independently can be a $C_4$ to $C_{20}$, a $C_4$ to $C_{15}$, or a $C_4$ to $C_{10}$ substituted cycloalkyl group. In an aspect, each cycloalkyl/substituted cycloalkyl group of a metal salt complexing group (or a first metal salt complexing group for the α-diimine first metal salt complex) having a cycloalkyl/substituted cycloalkyl group described herein independently can be cyclopentyl group, a substituted cyclopentyl group, a cyclohexyl group, or a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group which can be utilized as the substituted cycloalkyl group of a metal salt complexing group (or a first metal salt complexing group for the α-diimine first metal salt complex).

In any aspect and/or embodiment disclosed herein, the aryl group of any metal salt complexing group (or any first metal salt complexing group for the α-diimine first metal salt complex) having an aryl group disclosed herein independently can be a $C_6$ to $C_{20}$, a $C_6$ to $C_{15}$, or a $C_6$ to $C_{10}$ aryl group while the substituted aryl group of any metal salt complexing group (or any first metal salt complexing group for the α-diimine first metal salt complex) having a substituted aryl group disclosed herein independently a $C_6$ to $C_{20}$, a $C_6$ to $C_{15}$, or a $C_6$ to $C_{10}$ substituted aryl group. In an aspect, the aryl/substituted aryl group of any metal salt complexing group (or any first metal salt complexing group for the α-diimine first metal salt complex) having an aryl/substituted aryl group disclosed herein independently can be a phenyl group or a substituted phenyl group; alternatively, a phenyl group; or alternatively, a substituted phenyl group. In some aspects, the substituted phenyl group of any metal salt complexing group (or any first metal salt complexing group for the α-diimine first metal salt complex) having a substituted phenyl group independently can be a $C_6$ to $C_{20}$, a $C_6$ to $C_{15}$, or a $C_6$ to $C_{10}$ substituted phenyl group. In some aspects, the substituted phenyl group of any metal salt complexing group (or any first metal salt complexing group for the α-diimine first metal salt complex) having a substituted phenyl group independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as a substituted phenyl group for any metal salt complexing group (or any first metal salt complexing group for the α-diimine first metal salt complex) having a substituted aryl group or substituted phenyl group described herein can be the same or different; alternatively, all the substituents of a multi-substituted cycloalkyl group can be the same; or alternatively, all the substituents of a multi-substituted cycloalkyl group can be different. Each substituent of a substituted aryl group (general or specific) or substituted phenyl group (general or specific) which can be utilized as a substituted aryl group or a substituted phenyl group for any metal salt complexing group (or any first metal salt complexing group for the α-diimine first metal salt complex) having a substituted aryl group or substituted phenyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted aryl group (general or specific) or a substituted phenyl group (general or specific) which can be utilized as utilized as a substituted aryl group or a substituted phenyl group for any metal salt complexing group (or any first metal salt complexing group for the α-diimine first metal salt complex) having a substituted aryl group or substituted phenyl group.

In an aspect, the substituted phenyl group of any metal salt complexing group (or any first metal salt complexing group for the α-diimine first metal salt complex) having a substituted phenyl group disclosed herein independently can be a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. In an embodiment, one or more alkyl group substituents of a multi-alkyl group substituted phenyl group utilized as a substituted phenyl group for any metal salt complexing group (or any first metal salt complexing group for the α-diimine first metal salt complex) having an alkyl substituted phenyl group described herein can be the same or different; alternatively, all the substituents of a multi-alkyl group substituted cycloalkyl group can be the same; or alternatively, all the substituents of a multi-alkyl group substituted cycloalkyl group can be different. Alkyl substituent groups (general and specific) are independently described herein and these alkyl substituent groups can be utilized, without limitation, to further describe any alkyl substituted phenyl group which can be utilized as a substituted phenyl group for any metal salt complexing group (or any first metal salt complexing group for the α-diimine first metal salt complex) having a substituted aryl group or substituted phenyl group described herein. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, the substituted phenyl group of any metal salt complexing group (or any first metal salt complexing group for the α-diimine first metal salt complex) having a substituted phenyl group disclosed herein independently can be a 3,5-dimethylphenyl group.

The linking group linking the metal salt complexing group (or the first metal salt complexing group for the α-diimine first metal salt complex) to the second imine nitrogen atom of the α-diimine group can be a bond or an organyl group; alternatively, a bond or an organyl group consisting essentially of inert functional groups; alternatively, a bond or a hydrocarbyl group; alternatively, an organyl group; alternatively, an organyl group consisting essentially of inert functional groups; alternatively, a hydrocarbyl group; or alternatively, a bond. In any aspect and/or embodiment disclosed herein, the organyl linking group linking the metal salt complexing group (or the first metal salt complexing group for the α-diimine first metal salt complex) to the second imine nitrogen atom of the α-diimine group can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the organyl group consisting essentially of inert functional groups linking group linking the metal salt complexing group (or the first metal salt complexing group for the α-diimine first metal salt complex) to the second imine nitrogen atom of the α-diimine group can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the hydrocarbyl group linking group linking the metal salt complexing group (or the first metal salt complexing group for the α-diimine first metal salt complex) to the second imine nitrogen atom of the α-diimine group can be a $C_1$ to $C_{20}$, a $C_1$ to $C_{15}$, a $C_1$ to $C_{10}$, or a $C_1$ to $C_5$ hydrocarbyl group. In any aspect and/or embodiment disclosed herein, the hydrocarbyl group linking group linking the metal salt complexing group (or the first metal salt complexing group for the α-diimine first metal salt complex) to the second imine nitrogen atom of the α-diimine group can be a $C_1$ to $C_{20}$, a $C_1$ to $C_{15}$, a $C_1$ to $C_{10}$, or a $C_1$ to $C_5$ alkyl group. Generally, the linking group linking the metal salt complexing group (or the first metal salt complexing group for the α-diimine first metal salt complex) to the second imine nitrogen atom of the α-diimine group can be saturated or unsaturated, linear or branched, acyclic or cyclic, and/or aliphatic or aromatic.

In an aspect, the linking group linking the metal salt complexing group (or the first metal salt complexing group for the α-diimine first metal salt complex) to the second imine nitrogen atom of the α-diimine group can be —(C($R^{L1}$)$_2$)$_m$—, a phenyl-1,2-ene group, or a substituted phenyl-1,2-ene group; alternatively, a phenyl-1,2-ene group or a substituted phenyl-1,2-ene group; alternatively, —(C($R^{L1}$)$_2$)$_m$—; alternatively, a phenyl-1,2-ene group; alternatively, a substituted phenyl-1,2-ene group. $R^{L1}$ and m are independent elements of the linking group having the structure —(C($R^{L1}$)$_2$)$_m$— and are independently described herein. The independent descriptions of $R^{L1}$ and m can be utilized without limitation, and in any combination, to further describe the linking group linking the metal salt complexing group (or the first metal salt complexing group for the α-diimine first metal salt complex) to the second imine nitrogen atom of the α-diimine group having the structure —(C($R^{L1}$)$_2$)$_m$—. Within the structure —(C($R^{L1}$)$_2$)$_m$—, each $R^{L1}$ independently can be hydrogen, a methyl group, an ethyl group, a propyl group, an isopropyl group, or a butyl group; alternatively, hydrogen, a methyl group, or a propyl group. Within the structure —(C($R^{L1}$)$_2$)$_m$—, m can be an integer from 1 to 5; alternatively, 2 or 3; alternatively, 2; or alternatively, 3. Each substituent of a substituted phenyl-1,2-ene group which can be utilized as the linking group linking the metal salt complexing group (or the first metal salt complexing group for the α-diimine first metal salt complex) to the second imine nitrogen atom of the α-diimine group can be a halide, an alkyl group, or an alkoxy group; alternatively, a halide or an alkyl group; alternatively, a halide and an alkoxy group; alternatively, an alkyl group or an alkoxy group; alternatively, a halide; alternatively, an alkyl group; or alternatively, an alkoxy group. Halides, alkyl groups (general and specific), and alkoxy groups (general and specific) that can be utilized as substituents are independently disclosed herein and can be utilized without limitation, and in any combination, to further describe the substituted phenyl-1,2-ene group which can be utilized as the linking group linking the metal salt complexing group (or the first metal salt complexing group for the α-diimine first metal salt complex) to the second imine nitrogen atom of the α-diimine group. In some aspects, the linking group linking the metal salt complexing group (or the first metal salt complexing group for the α-diimine first metal salt complex) to the second imine nitrogen atom of the α-diimine group can be a methylene group, an eth-1,2-ylene group, a prop-1,3-ylene group, a dimethylmethylene group, a butyl-1,4-ene group or a phen-1,2-ylene group. In some non-limiting aspects, the linking group linking the metal salt complexing group (or the first metal salt complexing group for the α-diimine first metal salt complex) to the second imine nitrogen atom of the α-diimine group can be an eth-1,2-ylene group, a prop-1,3-ylene group, or a phen-1,2-ylene group; alternatively, an eth-1,2-ylene group, or a prop-1,3-ylene group; alternatively, an eth-1,2-ylene group; alternatively, a prop-1,3-ylene group; or alternatively, a phen-1,2-ylene group.

In a non-limiting aspect, the second imine group comprising (1) a metal salt complexing group (or the first metal salt complexing group for the α-diimine first metal salt complex) and (2) a linking group linking the metal salt complexing group (or the first metal salt complexing group for the α-diimine first metal salt complex) to a second imine nitrogen atom of the α-diimine group can be a 2-(N,N'-diisopropylaminyl)ethyl group, a 2-(N,N'-diphenylaminyl)ethyl group, a 2-(N,N'-di-(3,5-dimethylphenyl)aminyl)ethyl group, a 2-(diisopropylphosphinyl)ethyl group, a 2-(diphenylphosphinyl)ethyl group, a 2-(di-(3,5-dimethylphenyl)phosphinyl)ethyl group, a 3-(diisopropylphosphinyl)propyl group, a 3-(diphenylphosphinyl)propyl group, a 3-(di-(3,5-dimethylphenyl)phosphinyl)propyl group, a 2-isopropoxyethyl group, a 2-phenoxyethyl group, or a 2-(3,5-dimethylphenoxy)ethyl group. In some non-limiting aspects, the second imine group comprising (1) a metal salt complexing group (or the first metal salt complexing group for the α-diimine first metal salt complex) and (2) a linking group linking the metal salt complexing group (or the first metal salt complexing group for the α-diimine first metal salt complex) to a second imine nitrogen atom of the α-diimine group can be a 2-(N,N'-diisopropylaminyl)ethyl group, a 2-(N,N'-diphenylaminyl)ethyl group, a 2-(N,N'-di-(3,5-dimethylphenyl)aminyl)ethyl group; alternatively, a 2-(diisopropylphosphinyl)ethyl group, a 2-(diphenylphosphinyl)ethyl group, a 2-(di-(3,5-dimethylphenyl)phosphinyl)ethyl group, a 3-(diisopropylphosphinyl)propyl group, a 3-(diphenylphosphinyl)propyl group, a 3-(di-(3,5-dimethylphenyl)phosphinyl)propyl group; or alternatively, a 2-isopropoxyethyl group, a 2-phenoxyethyl group, or a 2-(3,5- dimethylphenoxy)ethyl group. In other non-limiting aspects, the second imine group comprising (1) a metal salt complexing group (e.g. the first metal salt complexing group for the α-diimine first metal salt complex) and (2) a linking group linking the metal salt complexing group (e.g. the first metal salt complexing group for the α-diimine first metal salt complex) to a second imine nitrogen atom of the α-diimine group can be a 2-(diisopropylphosphinyl)ethyl group, a 2-(diphenylphosphinyl)ethyl group, a 2-(di-(3,5-dimethylphenyl)phosphinyl)ethyl group; alternatively, a 3-(diisopropyl-phosphinyl)propyl group, a 3-(diphenylphosphinyl)propyl group, a 3-(di-(3,5-dimethylphenyl)-phosphinyl)propyl group; alternatively, a 2-(diisopropylphosphinyl)ethyl group; alternatively, a 2-(diphenylphosphinyl)ethyl group; or alternatively, a 2-(di-(3,5-dimethylphenyl)phosphinyl)ethyl group.

In various aspects and/or embodiments, a pyridine bisimine and a metal salt, or a pyridine bisimine first metal salt complex, can be utilized in the processes described herein. Generally, the pyridine bisimine or the pyridine bisimine of the pyridine bisimine first metal salt complex disclosed herein, can be any pyridine bisimine, or any pyridine bisimine of the pyridine bisimine first metal salt complex disclosed herein, that when contacted with the other materials of the process described herein (e.g., metal salt, ethylene, organoaluminum compound and/or any other appropriate reagent(s)), under the appropriate conditions, can form an oligomer product. Generally, the pyridine bisimine and the metal salt, or pyridine bisimine first metal salt complexes (or the pyridine bisimine and the first metal salt of the pyridine bisimine first metal salt complex) are independent elements of the processes described herein and are independently disclosed herein. The independent descriptions of the pyridine bisimine and the metal salt, or pyridine bisimine first metal salt complexes (or the pyridine bisimine and the first metal salt of the pyridine bisimine first metal salt complex) can be used without limitation, and in any combination, to further describe the processes that can be utilized in the aspects and/or embodiments of the processes described herein. In an aspect, the pyridine bisimine (or the pyridine bisimine of the pyridine bisimine first metal salt complex) can comprise only one pyridine bisimine group; alternatively, at least two pyridine bisimine groups; or alternatively, the pyridine bisimine can comprise only two pyridine bisimine groups.

In an aspect, the pyridine bisimine or the pyridine bisimine of the pyridine bisimine first metal salt complex can have Structure PBI I or Structure PBI II; alternatively, Structure PBI I; or alternatively, Structure PBI II. In an aspect, any pyridine bisimine first metal salt complex can have Structure PBIMC I or Structure PBIMC II; alternatively, Structure PBIMC I; or alternatively, Structure PBIMC II.

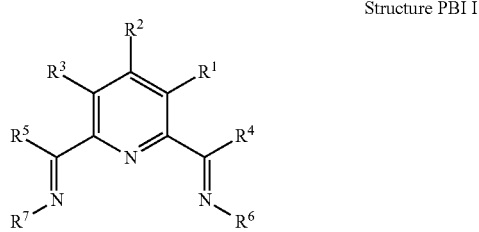

Structure PBI I

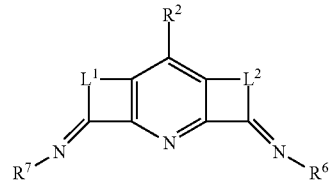

Structure PBI II

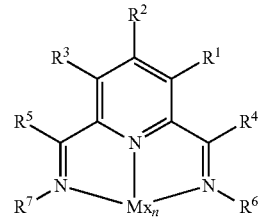

Structure PBIMC I

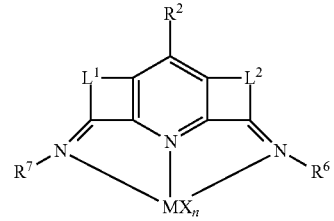

Structure PBIMC II $R^1$, $R^2$, $R^3$, $R^4$, $R^5$, $R^6$, and $R^7$ of the pyridine bisimine having Structure PBI I or the pyridine bisimine first metal salt complex having Structure PBIMC I are independent elements of the pyridine bisimine having Structure PBI I and the pyridine bisimine first metal salt complex having Structure PBIMC I and are independently described herein. The independent descriptions of $R^1$, $R^2$, $R^3$, $R^4$, $R^5$, $R^6$, and $R^7$ can utilized without limitation, and in any combination, to further describe the pyridine bisimine having Structure PBI I and/or the pyridine bisimine first metal salt complex having Structure PBIMC I. Similarly, $R^2$, $R^6$, $R^7$, $L^1$, and $L^2$ of the pyridine bisimine having Structure PBI II or the pyridine bisimine first metal salt complex having Structure PBIMC II are independent elements of the pyridine bisimine having Structure PBI II and the pyridine bisimine first metal salt complex having Structure PBIMC II and are independently described herein. The independent descriptions of $R^2$, $R^6$, $R^7$, $L^1$, and $L^2$ can utilized without limitation, and in any combination, to further describe the pyridine bisimine having Structure PBI II and/or the pyridine bisimine first metal salt complex having Structure PBIMC II. Additionally, the first metal salt, $MX_n$, is independently described herein and can be combined, without limitation, with the independently described $R^1$, $R^2$, $R^3$, $R^4$, $R^5$, $R^6$, $R^7$, $L^1$, and $L^2$ to further describe the appropriate pyridine bisimine first metal salt complex structure described herein which have an $R^1$, $R^2$, $R^3$, $R^4$, $R^5$, $R^6$, $R^7$, $L^1$, and/or $L^2$.

Generally, $R^1$, $R^2$, and/or $R^3$ of the respective pyridine bisimines and pyridine bisimine first metal salt complexes, which have an $R^1$, $R^2$, and/or $R^3$, independently can be hydrogen, an inert functional group, or an organyl group; alternatively, hydrogen or an organyl group; alternatively, an inert functional group or an organyl group; alternatively, hydrogen, an inert functional group, or an organyl group consisting essentially of inert functional groups; alternatively, hydrogen or an organyl group consisting essentially of inert functional groups; alternatively, an inert functional group or an organyl group consisting essentially of inert functional groups; alternatively, hydrogen, an inert functional group, or a hydrocarbyl group; alternatively, hydrogen or a hydrocarbyl group; alternatively, an inert functional group or a hydrocarbyl group; alternatively, hydrogen or an inert functional group; alternatively, hydrogen; alternatively, an inert functional group; alternatively, an organyl group; alternatively, organyl group consisting essentially of inert functional groups; or alternatively, a hydrocarbyl group. In any aspect and/or embodiment disclosed herein, the $R^1$, $R^2$, and/or $R^3$ organyl groups of the pyridine bisimines and/or pyridine bisimine first metal salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the $R^1$, $R^2$, and/or $R^3$ organyl groups consisting essentially of inert functional groups, of the pyridine bisimines and/or pyridine bisimine first metal salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^1$, $R^2$, and/or $R^3$ hydrocarbyl groups of the pyridine bisimines and/or pyridine bisimine first metal salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ hydrocarbyl group.

In any aspect and/or embodiment disclosed herein, the hydrocarbyl group which can be utilized as $R^1$, $R^2$, and/or $R^3$ of the pyridine bisimines and pyridine bisimine first metal salt complexes which have an $R^1$, $R^2$, and/or $R^3$ hydrocarbyl group, independently can be a $C_1$ to $C_{20}$, a $C_1$ to $C_{10}$, or a $C_1$ to $C_5$ alkyl group. In an aspect, the $R^1$, $R^2$, and/or $R^3$ alkyl groups of the pyridine bisimines and pyridine bisimine first metal salt complexes which have an $R^1$, $R^2$, and/or $R^3$ alkyl group, independently can be a methyl group, an ethyl group, a propyl group, a butyl group, a pentyl group, a hexyl group, a heptyl group, or an octyl group. In some aspects, the $R^1$, $R^2$, and/or $R^3$ alkyl groups of the pyridine bisimines and pyridine bisimine first metal salt complexes which have an $R^1$, $R^2$, and/or $R^3$ alkyl group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In a particular aspect, $R^1$, $R^2$, and/or $R^3$ of the pyridine bisimines which have an $R^1$, $R^2$, and/or $R^3$ group, each can be hydrogen. In these aspects, the pyridine bisimine can have Structure PBI III or Structure PBI IV; alternatively, Structure PBI III; or alternatively, Structure PBI IV. Similarly, in a particular aspect, $R^1$, $R^2$, and $R^3$ of the pyridine bisimine first metal salt complexes which have an $R^1$, $R^2$, and/or $R^3$ group, each can be hydrogen. In these aspects, the pyridine bisimine first metal salt complexes can have Structure PBIMC III or Structure PBIMC IV; alternatively, Structure PBIMC III; or alternatively, Structure PBIMC IV.

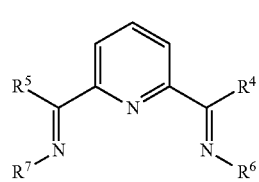

Structure PBI III

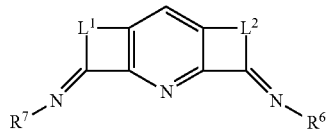

Structure PBI IV

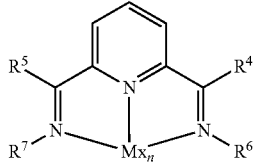

Structure PBIMC III

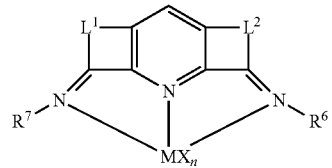

Structure PBIMC IV $R^4$, $R^5$, $R^6$, and $R^7$ of the pyridine bisimine having Structure PBI III or the pyridine bisimine first metal salt complex having Structure PBIMC III are independent elements of the pyridine bisimine having Structure PBI III and the pyridine bisimine first metal salt complex having Structure PBIMC III and are independently described herein. The independent descriptions of $R^4$, $R^5$, $R^6$, and $R^7$ can be utilized without limitation, and in any combination, to further describe the pyridine bisimine having Structure PBI III and/or the pyridine bisimine first metal salt complex having Structure PBIMC III. Similarly, $R^6$, $R^7$, $L^1$, and $L^2$ of the pyridine bisimine having Structure PBI IV or the pyridine bisimine first metal salt complex having Structure PBIMC IV are independent elements of the pyridine bisimine having Structure PBI IV and the pyridine bisimine first metal salt complex having Structure PBIMC IV and are independently described herein. The independent descriptions of $R^6$, $R^7$, $L^1$, and $L^2$ can be utilized without limitation, and in any combination, to further describe the pyridine bisimine having Structure PBI IV and/or the pyridine bisimine first metal salt complex having Structure PBIMC IV. Additionally, the first metal salt, $MX_n$, is independently described herein and can be combined, without limitation, with the independently described $R^4$, $R^5$, $R^6$, $R^7$, $L^1$, and $L^2$ to further describe the appropriate pyridine bisimine first metal salt complex structure described herein which have an $R^4$, $R^5$, $R^6$, $R^7$, $L^1$, and/or $L^2$.

Generally, $R^4$ and/or $R^5$ of the pyridine bisimines and pyridine bisimine first metal salt complexes, which have an $R^4$ and/or $R^5$, independently can be hydrogen or an organyl group; alternatively, hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In any aspect and/or embodiment disclosed herein, the $R^4$ and/or $R^5$ organyl groups of the pyridine bisimines and pyridine bisimine first metal salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the $R^4$ and/or $R^5$ organyl groups consisting essentially of inert functional groups, of the pyridine bisimines and pyridine bisimine first metal salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^4$ and/or $R^5$ hydrocarbyl groups of the pyridine bisimines and pyridine bisimine first metal salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ hydrocarbyl group.

In any aspect and/or embodiment disclosed herein, the $R^4$ and/or $R^5$ hydrocarbyl groups of the pyridine bisimines and pyridine bisimine first metal salt complexes which have an $R^4$ and/or $R^5$ group, independently can be a $C_1$ to $C_{20}$, a $C_1$ to $C_{10}$, or a $C_1$ to $C_5$ alkyl group. In an aspect, the $R^4$ and/or $R^5$ alkyl groups of the pyridine bisimines and pyridine bisimine first metal salt complexes which have an $R^4$ and/or $R^5$ group, independently can be a methyl group, an ethyl group, a propyl group, a butyl group, a pentyl group, a hexyl group, a heptyl group, or an octyl group. In some aspects, the $R^4$ and/or $R^5$ alkyl groups of the pyridine bisimines and pyridine bisimine first metal salt complexes which have an $R^4$ and/or $R^5$ group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In an aspect, $R^1$ and $R^4$ and/or $R^3$ and $R^5$ can be joined to form a ring or a ring system containing two carbon atoms of the pyridine group and the carbon atom of the imine group. In such aspects, $L^1$ represents the joined $R^3$ and $R^5$ while $L^2$ represents the joined $R^1$ and $R^4$. Generally, $L^1$ and/or $L^2$ of a pyridine bisimine or pyridine bisimine metal salt complex having an $L^1$ and/or $L^2$ independently can be an organylene group; alternatively, an organylene group consisting essentially of inert functional groups; or alternatively, a hydrocarbylene group. In any aspect or embodiment disclosed herein, the $L^1$ and/or $L^2$ organylene groups of a pyridine bisimine or pyridine bisimine first metal salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ organylene group. In any aspect or embodiment disclosed herein, the $L^1$ and/or $L^2$ organylene groups consisting essentially of inert functional groups of a pyridine bisimine or pyridine bisimine first metal salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ organylene group consisting essentially of inert functional groups. In any aspect or embodiment disclosed herein, the $L^1$ and/or $L^2$ hydrocarbylene groups of a pyridine bisimine or pyridine bisimine first metal salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ hydrocarbylene group. In any aspect or embodiments disclosed herein, the $L^1$ and/or $L^2$ hydrocarbylene groups of the pyridine bisimines and pyridine bisimine first metal salt complexes which have an $L^1$ and/or $L^2$, independently can be a $C_2$ to $C_{20}$, a $C_2$ to $C_{10}$, or a $C_2$ to $C_5$ alkylene group. In any aspect or embodiment where the pyridine bisimine or the pyridine bisimine first metal salt complex has an $L^1$ and an $L^2$ group, $L^1$ and $L^2$ can be different; or alternatively, $L^1$ and $L^2$ can be the same.

In an embodiment, $L^1$ and/or $L^2$ independently can have the structure $-(C(R^{11})_2)_p-$. Generally, $R^{11}$ and p are independent features of $L^1$ and/or $L^2$ having the structure $-(C(R^{11})_2)_p-$ and are independently described herein. The independent descriptions of $R^{11}$ and p can be utilized without limitation, and in any combination, to describe $L^1$ and/or $L^2$ having the structure $-(C(R^{11})_2)_p-$ and can be further utilized to describe the pyridine bisimines and/or the pyridine bisimine first metal salt complexes which have an $L^1$ and/or $L^2$. In an embodiment, each $R^{11}$ independently can be hydrogen, an inert functional group, or a hydrocarbyl group; alternatively, hydrogen or a hydrocarbyl group; alternatively, hydrogen; alternatively, an inert functional group; or alternatively, a hydrocarbyl group. General and specific inert functional groups and hydrocarbyl groups are independently described herein (e.g., as potential substituent groups) and these descriptions can be utilized without limitation to further describe $L^1$ and $L^2$. In an aspect, each p independently can be an integer from 1 to 5; alternatively, 2 or 3; alternatively, 2; or alternatively, 3. In a non-limiting aspect, $L^1$ and $L^2$ independently can be $-CH_2CH_2-$, $-CH_2CH_2CH_2-$, $-C(CH_3)_2-$, or $-CH_2CH_2CH_2CH_2-$; alternatively, $-CH_2CH_2-$ or $-CH_2CH_2CH_2-$; alternatively, $-CH_2CH_2-$; or alternatively, $-CHCH_2CH_2-$. In an aspect, $L^1$ and $L^2$ can be different. In other aspects, $L^1$ and $L^2$ can be the same.

Generally, $R^6$ and/or $R^7$ of the pyridine bisimines and the pyridine bisimine first metal salt complexes independently can be an aryl group, a substituted aryl group, a phenyl group, or a substituted phenyl group; alternatively, an aryl group or a substituted aryl group; alternatively, a phenyl group or a substituted phenyl group; alternatively, an aryl group; alternatively, a substituted aryl group; alternatively, a phenyl group; or alternatively, a substituted phenyl group. In any aspect and/or embodiment disclosed herein, the $R^6$ and/or $R^7$ aryl groups of the pyridine bisimines and/or pyridine bisimine first metal salt complexes independently can be a $C_6$ to $C_{20}$, a $C_6$ to $C_{15}$, or a $C_6$ to $C_{10}$ aryl group. In any aspect and/or embodiment disclosed herein, the $R^6$ and/or $R^7$ substituted aryl groups of the pyridine bisimines and/or pyridine bisimine first metal salt complexes independently can be a $C_6$ to $C_{20}$, a $C_6$ to $C_{15}$, or a $C_6$ to $C_{10}$ substituted aryl group. In any aspect and/or embodiment disclosed herein, the $R^6$ and/or $R^7$ substituted phenyl groups of the pyridine bisimines and/or pyridine bisimine first metal salt complexes independently can be a $C_6$ to $C_{20}$, a $C_6$ to $C_{15}$, or a $C_6$ to $C_{15}$ substituted phenyl group. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine first metal salt complexes.

In an embodiment, each substituted phenyl group which can be utilized as $R^6$ and/or $R^7$ of the pyridine bisimines and the pyridine bisimine first metal salt complexes independently can be a substituted phenyl group comprising a substituent at the 2-position, a substituted phenyl group comprising a substituent at the 3-position, a substituted phenyl group comprising a substituent at the 4-position, a substituted phenyl group comprising substituents at the 2- and 3-positions, a substituted phenyl group comprising substituents at the 2- and 4-positions, a substituted phenyl group comprising substituents at the 2- and 5-positions, a substituted phenyl group comprising substituents at the 3- and 5-positions, a substituted phenyl group comprising substituents at the 2- and 6-positions, or a substituted phenyl group comprising substituents at the 2-, 4-, and 6-positions; alternatively, a substituted phenyl group comprising a substituent at the 2-position, a substituted phenyl group comprising a substituent at the 4-position, a substituted phenyl group comprising substituents at the 2- and 4-positions, a substituted phenyl group comprising substituents at the 2- and 6-positions, or a substituted phenyl group comprising substituents at the 2-, 4-, and 6-positions; alternatively, a substituted phenyl group comprising substituents at the 2- and 6-positions or a substituted phenyl group comprising substituents at the 2-, 4-, and 6-positions; alternatively, a substituted phenyl group comprising a substituent at the 2-position; alternatively, a substituted phenyl group comprising a substituent at the 3-position; alternatively, a substituted phenyl group comprising a substituent at the 4-position; alternatively, a substituted phenyl group comprising substituents at the 2- and 3-positions; alternatively, a substituted phenyl group comprising substituents at the 2- and 4-positions; alternatively, a substituted phenyl group comprising substituents at the 2- and 5-positions; alternatively, a substituted phenyl group comprising substituents at the 3- and 5-positions; alternatively, a substituted phenyl group comprising substituents at the 2- and 6-positions; or alternatively, a substituted phenyl group comprising substituents at the 2-, 4-, and 6-positions. In some embodiments, each substituted phenyl group which can be utilized as $R^6$ and/or $R^7$ of the pyridine bisimines and the pyridine bisimine first metal salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of the 2- and 6-positions of the $R^6$ and $R^7$ substituted phenyl groups can be fluorine. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine first metal salt complexes. Further, one having ordinary skill in the art can recognize the independently described substituted phenyl group(s) which meet the criteria for a substituted phenyl group (e.g., primary, secondary, tertiary, and quaternary carbon atom groups, among other criteria) and choose the appropriate substituted phenyl group(s) to meet any particular criteria for a substituted phenyl group(s) for a pyridine bisimine and/or a pyridine bisimine first metal salt described herein.

In an embodiment, each substituted phenyl group which can be utilized as $R^6$ and/or $R^7$ of the pyridine bisimines and the pyridine bisimine first metal salt complexes independently can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubstituted phenyl group. In some embodiments, each substituted phenyl group which can be utilized as $R^6$ and/or $R^7$ of the pyridine bisimines and the pyridine bisimine first metal salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of 2- and 6-positions of the $R^6$ and $R^7$ substituted phenyl groups can be fluorine. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine first metal salt complexes. Further, one having ordinary skill in the art can recognize the independently described substituted phenyl group(s) which meet the criteria for a substituted phenyl group (e.g., primary, secondary, tertiary, and quaternary carbon atom groups, among other criteria) and choose the appropriate substituted phenyl group(s) to meet any particular criteria for a substituted phenyl group(s) for a pyridine bisimine and/or a pyridine bisimine first metal salt described herein.

In an embodiment, $R^6$ and/or $R^7$ of the pyridine bisimines and the pyridine bisimine first metal salt complexes independently can be a phenyl group, a 2-methylphenyl group, a 2-ethylphenyl group, a 2-isopropylphenyl group, a 2-tert-butylphenyl group, a 2-(phenyl)phenyl group, a 2-trifluoromethylphenyl group, a 2-fluorophenyl group, a 2-methoxyphenyl group, a 4-methylphenyl group, a 4-ethylphenyl group, a 4-isopropylphenyl group, a 4-tert-butylphenyl group, a 4-fluorophenyl group, a 4-trifluoromethylphenyl group, a 4-methoxyphenyl group, a 2,3-dimethyl phenyl group, a 2-fluoro-3-methylphenyl group, a 2,4-dimethylphenyl group, a 2,4-diethylphenyl group, a 2,4-diisopropylphenyl group, a 2,4-di-tert-butylphenyl group, a 2-fluoro-4-methylphenyl group, a 2,5-dimethylphenyl group, a 2,6-dimethylphenyl group, a 2,6-diethylphenyl group, a 2,6-diisopropylphenylgroup, a 2,6-diphenylphenyl group, a 2-fluoro-6-methylphenyl group, a 2,6-bis(trifluoromethyl)phenyl group, a 2,6-difluorophenyl group, a 3,5-dimethylphenyl group, a 3,5-diethylphenyl group, a 3,5-diisopropylphenyl group, a 3,5-di-tert-butylphenyl group, a 3,5-di(trifluoromethyl)phenyl group, or a 2,4,6-trimethylphenyl group. In some embodiments, $R^6$ and/or $R^7$ of the pyridine bisimines and the pyridine bisimine first metal salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of the 2- and 6-positions of the $R^6$ and $R^7$ substituted phenyl groups can be fluorine. One having ordinary skill in the art can recognize the independently described substituted phenyl group(s) which meet the criteria for a substituted phenyl group (e.g., primary, secondary, and tertiary carbon atom groups, among other criteria) and choose the appropriate substituted phenyl group(s) to meet any particular criteria for a substituted phenyl group(s) for a pyridine bisimine and/or a pyridine bisimine first metal salt described herein.

In an embodiment, the pyridine bisimine or the pyridine bisimine of the pyridine bisimine first metal salt complex can comprise, consist essentially of, or can be, a 2,6-bis[(aryl-imine)hydrocarbyl]pyridine, a bis[(substituted arylimine)hydrocarbyl]pyridine, or an [(arylimine)-hydrocarbyl], [(substituted arylimine)hydrocarbyl]pyridine; alternatively, a 2,6-bis[(arylimine)hydrocarbyl]pyridine; alternatively, a bis[(substituted arylimine)hydrocarbyl]pyridine; or alternatively, an [(arylimine)hydrocarbyl], or a [(substituted arylimine)hydrocarbyl]pyridine. In an aspect, the pyridine bisimine first metal salt complex can comprise, can consist essentially of, or can be, a 2,6-bis[(arylimine)hydrocarbyl]pyridine first metal salt complex, a bis[(substituted arylimine)hydrocarbyl]pyridine first metal salt complex, or an [(arylimine)hydrocarbyl],[(substituted arylimine)-hydrocarbyl]pyridine first metal salt complex; alternatively, a 2,6-bis[(arylimine)hydrocarbyl]pyridine first metal salt complex; alternatively, a bis[(substituted arylimine)hydrocarbyl]pyridine first metal salt complex; or alternatively, an [(arylimine)hydrocarbyl],[(substituted arylimine)hydrocarbyl]pyridine first metal salt complex. In some aspects, the aryl groups of the 2,6-bis[(arylimine)hydrocarbyl]pyridine or the 2,6-bis[(arylimine)hydrocarbyl]pyridine first metal salt complex can be the same or can be different; alternatively, the same; or alternatively, different. In some aspects, the substituted aryl groups of the 2,6-bis[(substituted arylimine)hydrocarbyl]pyridine or the 2,6-bis[(substituted arylimine)hydrocarbyl]pyridine first metal salt complex can be the same or can be different; alternatively, the same; or alternatively, different. In an aspect, the pyridine bisimine or the pyridine bisimine of the pyridine bisimine first metal salt complex can comprise, consist essentially of, or can be, a 2,6-bis[(arylimine)hydrocarbyl]pyridine, a bis[(substituted arylimine)hydrocarbyl]pyridine, and/or an [(arylimine)hydrocarbyl],[(substituted arylimine)hydrocarbyl]pyridine wherein 1) one, two, or three of the aryl groups and/or substituted aryl groups positioned ortho to the carbon atom attached to the imine nitrogen independently can be a halogen, a primary carbon atom group, or a secondary carbon atom group and the remainder of the aryl groups and/or substituted aryl groups positioned ortho to the carbon atom attached to the imine nitrogen can be hydrogen, 2) one of the aryl groups and/or substituted aryl groups positioned ortho to the carbon atom attached to the imine nitrogen can be a tertiary carbon atom group, none, one, or two of the aryl groups and/or substituted aryl groups positioned ortho to the carbon atom attached to the imine nitrogen independently can be a halogen, a primary carbon atom group or a secondary carbon atom group, and the remainder of the aryl groups and/or substituted aryl groups positioned ortho to the carbon atom attached to the imine nitrogen can be hydrogen, 3) two of the aryl groups and/or substituted aryl groups positioned ortho to the carbon atom attached to the imine nitrogen independently can be a tertiary carbon atom group, none, or one of the aryl groups and/or substituted aryl groups positioned ortho to the carbon atom attached to the imine nitrogen independently can be a halogen, a primary carbon atom group, or a secondary carbon atom group, and the remainder of the aryl groups and/or substituted aryl groups positioned ortho to the carbon atom attached to the imine nitrogen can be hydrogen, 4) one or two of the aryl groups and/or substituted aryl groups positioned ortho to the carbon atom attached to the imine nitrogen independently can be a tertiary carbon atom group(s) and the remainder of the aryl groups and/or substituted aryl groups positioned ortho to the carbon atom attached to the imine nitrogen can be hydrogen, 5) one or two of the aryl groups and/or substituted aryl groups positioned ortho to the carbon atom attached to the imine nitrogen can be a quaternary carbon atom group and the remainder of the aryl groups and/or substituted aryl groups positioned ortho to the carbon atom attached to the imine nitrogen can be hydrogen, or 6) all four of the substituted aryl groups positioned ortho to the carbon atom attached to the imine nitrogen can be fluorine. Hydrocarbyl groups (general and specific), aryl groups (general and specific), and substituted aryl groups (general and specific) are independently described herein. The independent descriptions of the hydrocarbyl group, aryl groups, and substituted aryl groups can be utilized without limitation, and in any combination, to further describe the 2,6-bis [(arylimine)hydrocarbyl]pyridine, the bis[(substituted arylimine)hydrocarbyl]pyridine, or the [(arylimine)hydrocarbyl],[(substituted arylimine)hydrocarbyl]pyridine which can be utilized as the pyridine bisimine or the pyridine bisimine first metal salt complex that can be utilized in the processes described herein. One having ordinary skill in the art can recognize the independently described aryl group(s) and/or substituted aryl group(s) which meet the criteria for aryl group and/or substituted aryl groups (e.g., primary, secondary, and tertiary carbon atom groups, among other criteria) and choose the appropriate aryl group(s) and/or substituted aryl group(s) to meet any particular criteria for the aryl group(s) and/or substituted phenyl group(s) for a pyridine bisimine and/or a pyridine bisimine first metal salt complex described herein.

In an embodiment, the pyridine bisimine and/or the pyridine bisimine of the pyridine bisimine first metal salt complex can be 2,6-bis[(phenylimine)methyl]pyridine, 2,6-bis[(2-methylphenyl-imine)methyl]pyridine, 2,6-bis[(2-ethylphenylimine)methyl]pyridine, 2,6-bis[(2-isopropylphenylimine)-methyl]pyridine, 2,6-bis[(2,4-dimethylphenylimine)methyl]pyridine, 2,6-bis[(2,6-diethylphenylimine)-methyl]pyridine, 2-[(2,4,6-trimethylphenylimine)methyl]-6-[(4-methylphenylimine)methyl]pyridine, 2-[(2,4,6-trimethylphenylimine)methyl]-6-[(3,5-dimethylphenylimine)methyl]pyridine, or 2-[(2,4,6-trimethylphenylimine)methyl]-6-[(4-t-butylphenylimine)methyl]pyridine.

Additional descriptions of pyridine bisimines and pyridine bisimine first metal salt complexes suitable for use in the present disclosure can be found in U.S. Pat. Nos. 5,955,555, 6,103,946, 6,291,733, 6,489,497, 6,451,939, 6,455,660, 6,458,739, 6,472,341, 6,545,108, 6,559,091, 6,657,026, 6,683,187, 6,710,006, 6,911,505, 6,911,506, 7,001,964, 7,045,632, 7,056,997, 7,223,893, 7,456,284, 7,683,149, 7,902,415, 7,994,376 and EP 1229020A1.

In various aspects and embodiments, a phenanthroline imine (which also can be referred to as a 1,10-phenanthroline-2-imine or a 2-iminyl-1,10-phenanthroline) and a metal salt, or a phenanthroline imine first metal salt complex (which also can be referred to as a 1,10-phenanthroline-2-imine first metal salt complex or a 2-iminyl-1,10-phenanthroline first metal salt complex) can be utilized in the processes described herein. Generally, the phenanthroline imine, or the phenanthroline imine of the phenanthroline imine first metal salt complex, can be any phenanthroline imine, or any phenanthroline imine of the phenanthroline imine first metal salt complex, that when contacted with the other materials of the process described herein (e.g., metal salt, ethylene, organoaluminum compound and/or any other appropriate reagent(s)), under the appropriate conditions, can form an oligomer product. Generally, the phenanthroline imine and the metal salt, or the phenanthroline imine first metal salt complex (or the phenanthroline imine and the first metal salt of the phenanthroline imine first metal salt complex) are independent elements of the processes described herein and are independently disclosed herein. The independent descriptions of the phenanthroline imine and the metal salt, or the phenanthroline imine first metal salt complex (or the phenanthroline imine and the first metal salt of the phenanthroline imine first metal salt complex) can be used without limitation, and in any combination, to further describe the processes that can be utilized in the aspects and/or embodiments of the processes described herein.

In an aspect, the phenanthroline imine can have Structure PTI I. In an aspect, the phenanthroline imine first metal salt complex can have Structure PTIMC I.

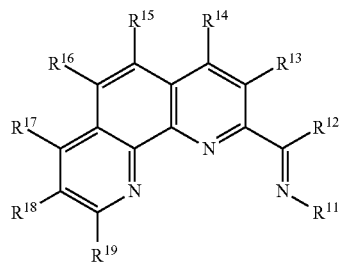

Structure PTI I

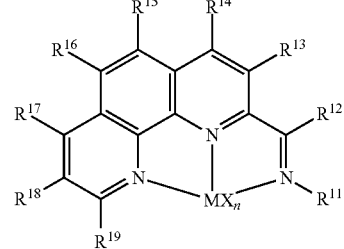

Structure PTIMC I $R^{11}$, $R^{12}$, $R^{13}$, $R^{14}$, $R^{15}$, $R^{16}$, $R^{17}$, $R^{18}$, and $R^{19}$ of the phenanthroline imine having Structure PTI I or phenanthroline imine first metal salt complex having Structure PTIMC I are independent elements of the phenanthroline imine having Structure PTI I and the phenanthroline imine first metal salt complex having Structure PBIMC I and are independently described herein. The independent descriptions of $R^{11}$, $R^{12}$, $R^{13}$, $R^{14}$, $R^{15}$, $R^{16}$, $R^{17}$, $R^{18}$, and $R^{19}$ can be utilized without limitation, and in any combination, to further describe the phenanthroline imine having Structure PTI I and/or the phenanthroline imine first metal salt complex having Structure PBIMC I. Additionally, the first metal salt, $MX_n$, is independently described herein and can be combined, without limitation, with the independently described $R^{11}$, $R^{12}$, $R^{13}$, $R^{14}$, $R^{15}$, $R^{16}$, $R^{17}$, $R^{18}$, and $R^{19}$ to further describe the phenanthroline imine first metal salt complex structures described herein.

Generally, $R^{13}$, $R^{14}$, $R^{15}$, $R^{16}$, $R^{17}$, $R^{18}$, and $R^{19}$ of the phenanthroline imines and phenanthroline imine first metal salt complexes, independently can be hydrogen, an inert functional group, or an organyl group; alternatively, hydrogen or an organyl group; alternatively, an inert functional group or an organyl group; alternatively, hydrogen, an inert functional group, or an organyl group consisting essentially of inert functional groups; alternatively, hydrogen or an organyl group consisting essentially of inert functional groups; alternatively, an inert functional group or an organyl group consisting essentially of inert functional groups; alternatively, hydrogen, an inert functional group, or a hydrocarbyl group; alternatively, hydrogen or a hydrocarbyl group; alternatively, an inert functional group or a hydrocarbyl group; alternatively, hydrogen or an inert functional group; alternatively, hydrogen; alternatively, an inert functional group; alternatively, an organyl group; alternatively, organyl group consisting essentially of inert functional groups; or alternatively, a hydrocarbyl group. In any aspect and/or embodiment disclosed herein, the organyl groups which can be utilized as $R^{13}$, $R^{14}$, $R^{15}$, $R^{16}$, $R^{17}$, $R^{18}$, and/or $R^{19}$, independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the organyl groups consisting essentially of inert functional groups which can be utilized as $R^{13}$, $R^{14}$, $R^{15}$, $R^{16}$, $R^{17}$, $R^{18}$, and/or $R^{19}$ independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the hydrocarbyl groups which can be utilized as $R^{13}$, $R^{14}$, $R^{15}$, $R^{16}$, $R^{17}$, $R^{18}$, and $R^{19}$ independently can be a $C_1$ to $C_{20}$, a $C_1$ to $C_{15}$, a $C_1$ to $C_{10}$, or a $C_1$ to $C_5$ hydrocarbyl group. In some embodiments, the inert functional groups which can be utilized as $R^{13}$, $R^{14}$, $R^{15}$, $R^{16}$, $R^{17}$, $R^{18}$, and $R^{19}$ independently can be a halide or an alkoxy group; alternatively, a halide; or alternatively, an alkoxy group.

In any aspect and/or embodiment disclosed herein, the hydrocarbyl group which can be utilized as $R^{13}$, $R^{14}$, $R^{15}$, $R^{16}$, $R^{17}$, $R^{18}$, and/or $R^{19}$ of the phenanthroline imines and phenanthroline imine first metal salt complexes which have an $R^{13}$, $R^{14}$, $R^{15}$, $R^{16}$, $R^{17}$, $R^{18}$, and/or $R^{19}$ group, independently can be a $C_1$ to $C_{20}$, a $C_1$ to $C_{10}$, or a $C_1$ to $C_5$. In an aspect, the alkyl groups which can be utilized as $R^{13}$, $R^{14}$, $R^{15}$, $R^{16}$, $R^{17}$, $R^{18}$, and/or $R^{19}$ of the phenanthroline imines and phenanthroline imine first metal salt complexes which have an $R^{13}$, $R^{14}$, $R^{15}$, $R^{16}$, $R^{17}$, $R^{18}$, and/or $R^{19}$ group, independently can be a methyl group, an ethyl group, a propyl group, a butyl group, a pentyl group, a hexyl group, a heptyl group, or an octyl group. In some aspects, the $R^{13}$, $R^{14}$, $R^{15}$, $R^{16}$, $R^{17}$, $R^{18}$, and/or $R^{19}$ alkyl groups of the phenanthroline imines and phenanthroline imine first metal salt complexes which have an $R^{13}$, $R^{14}$, $R^{15}$, $R^{16}$, $R^{17}$, $R^{18}$, and/or $R^{19}$ alkyl group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In some embodiments, each halide which can be utilized as $R^{13}$, $R^{14}$, $R^{15}$, $R^{16}$, $R^{17}$, $R^{18}$, and/or $R^{19}$ of the phenanthroline imines and phenanthroline imine first metal salt complexes independently can be fluoride, chloride, bromide or iodide; alternatively, fluoride, chloride, or bromide; alternatively, fluoride; alternatively, chloride; or alternatively, bromide. In some embodiments, each alkoxy group which can be utilized as $R^{13}$, $R^{14}$, $R^{15}$, $R^{16}$, $R^{17}$, $R^{18}$, and/or $R^{19}$ of the phenanthroline imines and phenanthroline imine first metal salt complexes independently can be a $C_1$ to $C_{10}$ alkoxy group or a $C_1$ to $C_5$ alkoxy group. In some embodiments, each alkoxy group which can be utilized as $R^{13}$, $R^{14}$, $R^{15}$, $R^{16}$, $R^{17}$, $R^{18}$, and $R^{19}$ independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group.

In a particular aspect, $R^{13}$, $R^{14}$, $R^{15}$, $R^{16}$, $R^{17}$, $R^{18}$, and $R^{19}$ of the phenanthroline imine each can be hydrogen. In these aspects, the phenanthroline imine can have Structure PTI II. Similarly, in a particular aspect, $R^{13}$, $R^{14}$, $R^{15}$, $R^{16}$, $R^{17}$, $R^{18}$, and $R^{19}$ of the phenanthroline imine first metal salt complex each can be hydrogen. In these aspects, the phenanthroline imine first metal salt complex can have Structure PTIMC II.

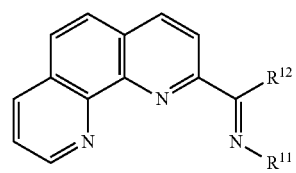

Structure PTI III

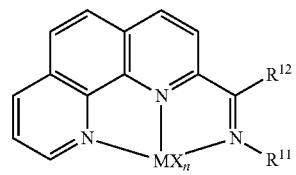

Structure PTIMC II $R^{11}$ and $R^{12}$ of the phenanthroline imine having Structure PTI I or Structure PTI II or the phenanthroline imine first metal salt complex having Structure PTIMC I or Structure PTIMC II are independent elements of the phenanthroline imine having Structure PTI I or Structure PTI II and the phenanthroline imine first metal salt complex having Structure PTIMC I or Structure PTIMC II and are independently described herein. The independent descriptions of $R^{11}$ and $R^{12}$ can be utilized without limitation, and in any combination, to further describe the phenanthroline imine having Structure PTI I or Structure PTI II and/or the phenanthroline imine first metal salt complex having Structure PTIMC I or Structure PTIMC II. Additionally, the metal salt, $MX_n$, is independently described herein can be combined, without limitation, with the independently described $R^{11}$ and $R^{12}$ to further describe the phenanthroline imine first metal salt complex having Structure PTIMC I or Structure PTIMC II.

Generally, $R^{11}$ of the phenanthroline imines and the phenanthroline imine first metal salt complexes can be an aryl group, a substituted aryl group, a phenyl group, or a substituted phenyl group; alternatively, an aryl group or a substituted aryl group; alternatively, a phenyl group or a substituted phenyl group; alternatively, an aryl group; alternatively, a substituted aryl group; alternatively, a phenyl group; or alternatively, a substituted phenyl group. In any aspect and/or embodiment disclosed herein, the $R^{11}$ aryl group of the phenanthroline imines and the phenanthroline imine first metal salt complexes can be a $C_6$ to $C_{20}$, a $C_6$ to $C_{15}$, or a $C_6$ to $C_{10}$ aryl group. In any aspect and/or embodiment disclosed herein, the $R^{11}$ substituted aryl groups of the phenanthroline imines and the phenanthroline imine first metal salt complexes can be a $C_6$ to $C_{20}$, a $C_6$ to $C_{15}$, or a $C_6$ to $C_{10}$ substituted aryl group. In any aspect and/or embodiment disclosed herein, the $R^{11}$ substituted phenyl groups of the phenanthroline imines and the phenanthroline imine first metal salt complexes can be a $C_6$ to $C_{20}$, a $C_6$ to $C_{15}$, or a $C_6$ to $C_{15}$ substituted phenyl group. Each substituent of a substituted aryl group (general or specific) or a substituted phenyl group (general or specific) which can be utilized as $R^{11}$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^{11}$ of the phenanthroline imines and the phenanthroline imine first metal salt complexes.

In an embodiment, each substituted phenyl group which can be utilized as $R^{11}$ substituted phenyl groups of the phenanthroline imines and the phenanthroline imine first metal salt complexes can be a substituted phenyl group comprising a substituent at the 2-position, a substituted phenyl group comprising a substituent at the 3-position, a substituted phenyl group comprising a substituent at the 4-position, a disubstituted phenyl group comprising substituents at the 2- and 3-positions, a disubstituted phenyl group comprising substituents at the 2- and 4-positions, a disubstituted phenyl group comprising substituents at the 2- and 5-positions, a disubstituted phenyl group comprising substituents at the 3- and 5-positions, a disubstituted phenyl group comprising substituents at the 2- and 6-positions, or a trisubstituted phenyl group comprising substituents at the 2-, 4-, and 6-positions; alternatively, a substituted phenyl group comprising a substituent at the 2-position, a substituted phenyl group comprising a substituent at the 4-position, a disubstituted phenyl group comprising substituents at the 2- and 4-positions, a disubstituted phenyl group comprising substituents at the 2- and 6-positions, or a trisubstituted phenyl group comprising substituents at the 2-, 4-, and 6-position; alternatively, a disubstituted phenyl group comprising substituents at the 2- and 6-positions or a trisubstituted phenyl group comprising substituents at the 2-, 4-, and 6-positions; alternatively, a substituted phenyl group comprising a substituent at the 2-position; alternatively, a substituted phenyl group comprising a substituent at the 3-position; alternatively, a substituted phenyl group comprising a substituent at the 4-position; alternatively, a disubstituted phenyl group comprising substituents at the 2- and 3-positions; alternatively, a disubstituted phenyl group comprising substituents at the 2- and 4-positions; alternatively, a disubstituted phenyl group comprising substituents at the 2- and 5-positions; alternatively, a disubstituted phenyl group comprising substituents at the 3- and 5-positions; alternatively, a disubstituted phenyl group comprising substituents at the 2- and 6-position; or alternatively, a trisubstituted phenyl group comprising substituents at the 2-, 4-, and 6-positions. In an aspect, each substituted phenyl group which can be utilized as $R^{11}$ substituted phenyl groups of the phenanthroline imines and the phenanthroline imine first metal salt complexes can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubstituted phenyl group. In an aspect where the substituted phenyl group has more than one substituent, two or more of the substituents can be different, each substituent can be different, or each substituent can be the same; alternatively, two or more of the substituents can be different; alternatively, each substituent can be different; or alternatively, each substituent can be the same. Each substituent of a substituted phenyl group (general or specific) which can be utilized as $R^{11}$ independently can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^{11}$ of the phenanthroline imines and the phenanthroline imine first metal salt complexes.

In an embodiment, each substituted phenyl group which can be utilized as an $R^{11}$ substituted phenyl group of the phenanthroline imines and the phenanthroline imine first metal salt complexes can be a substituted phenyl group comprising an alkyl group at the 2-position, a substituted phenyl group comprising an alkyl group at the 4-position, a disubstituted phenyl group comprising alkyl groups at the 2- and 4-positions, a disubstituted phenyl group comprising alkyl groups at the 2- and 6-positions, a trisubstituted phenyl group comprising alkyl groups at the 2-, 4-, and 6-positions, a substituted phenyl group comprising a halide at the 2-position, a disubstituted phenyl group comprising halides at the 2- and 4-positions, or a trisubstituted phenyl group comprising halides at the 2-, 4-, and 6-positions; alternatively, a substituted phenyl group comprising an alkyl group at the 2-position, a substituted phenyl group comprising an alkyl group at the 4-position, a disubstituted phenyl group comprising alkyl groups at the 2- and 4-positions, a disubstituted phenyl group comprising alkyl groups at the 2- and 6-positions, or a trisubstituted phenyl group comprising alkyl groups at the 2-, 4-, and 6-positions; alternatively, a substituted phenyl group comprising a halide at the 2-position, a disubstituted phenyl group comprising halides at the 2- and 4-positions, or a trisubstituted phenyl group comprising halides at the 2-, 4-, and 6-positions; alternatively, a disubstituted phenyl group comprising alkyl groups at the 2- and 4-positions, or a trisubstituted phenyl group comprising alkyl groups at the 2-, 4-, and 6-positions; alternatively, a disubstituted phenyl group comprising alkyl groups at the 2- and 4-positions; alternatively, a trisubstituted phenyl group comprising alkyl groups at the 2-, 4-, and 6-positions; alternatively, substituted phenyl group comprising a halide at the 2-position; alternatively, a disubstituted phenyl group comprising halides at the 2- and 4-positions; or alternatively, or a trisubstituted phenyl group comprising halides at the 2-, 4-, and 6-positions. In some embodiments, each substituted phenyl group which can be utilized as an $R^{11}$ substituted phenyl group of the phenanthroline imines and the phenanthroline imine first metal salt complexes can be a 2-alkylphenyl group, a 4-alkylphenyl group, a 2,4-dialkylphenyl group, a 2,6-dialkylphenyl group, a 2,4,6-trialkylphenyl group, a 2-halophenyl group, a 2,4-dihalophenyl group, a 2,4,6-trihalophenyl group, a 2,6-dialkyl-4-halophenyl group, or a 2,6-dihalo-4-alkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2,6-dialkylphenyl group or a 2,4,6-trialkylphenyl group; alternatively, a 2-halophenyl group, a 2,4-dihalophenyl group, or a 2,4,6-trihalophenyl group; alternatively, a 2,6-dialkyl-4-halophenyl group or a 2,6-dihalo-4-alkylphenyl group; alternatively, a 2,6-dialkylphenyl group or a 2,4,6-trialkylphenyl group; alternatively, a 2-alkylphenyl group; alternatively, a 4-alkylphenyl group; alternatively, a 2,4-dialkylphenyl group; alternatively, a 2,6-dialkylphenyl group; alternatively, a 2,4,6-trialkylphenyl group; alternatively, a 2-halophenyl group; alternatively, a 2,4-dihalophenyl group; alternatively, a 2,4,6-trihalophenyl group; alternatively, a 2,6-dialkyl-4-halophenyl group; or alternatively, a 2,6-dihalo-4-alkylphenyl group. In an embodiment where the substituted phenyl group has more than one substituent, two or more of the substituents can be different, each substituent can be different, or each substituent can be the same; alternatively, two or more of the substituents can be different; alternatively, each substituent can be different; or alternatively, each substituent can be the same. Halides and alkyl groups (general and specific) that can be utilized as substituents are independently disclosed herein and can be utilized without limitation, and in any combination, to further describe $R^{11}$ of the phenanthroline imines and the phenanthroline imine first metal salt complexes.

In an embodiment, the substituted phenyl $R^{11}$ group of the phenanthroline imines and the phenanthroline imine first metal salt complexes can be a 2-methylphenyl group, a 2-ethylphenyl group, a 2-isopropylphenyl group, a 2-tert-butylphenyl group, a 2-fluorophenyl group, a 2-chlorophenyl group, a 2-bromophenyl group, a 2,6-dimethylphenyl group, a 2,6-diethylphenyl group, a 2,6-diisopropylphenyl group, a 2,6-di-tert-butylphenyl group, a 2,4,6-trimethylphenyl group, a 2,6-difluorophenyl group, a 2,6-dichlorophenyl group, a 2,6-dibromophenyl group, a 2,4,6-trifluorophenyl group, a 2,4,6-trichlorophenyl group, a 2,4,6-tribromophenyl group, a 2,4-dibromo-6-chlorophenyl group, a 2,6-dimethyl-6-bromophenyl group, or a 2,6-dibromo-4-methylphenyl group; alternatively, a 2,6-dimethylphenyl group, a 2,6-diethylphenyl group, a 2,6-diisopropylphenyl group, or a 2,4,6-trimethylphenyl group; alternatively, a 2,6-difluorophenyl group, a 2,6-dichlorophenyl group, a 2,6-dibromophenyl group, a 2,4,6-tribromophenyl group, or a 2,4-dibromo-6-chlorophenyl group; alternatively, a 2,6-dimethyl-6-bromophenyl group or a 2,6-dibromo-6-methylphenyl group; alternatively, a 2,6-dimethyl-6-bromophenyl group or a 2,6-dibromo-4-methylphenyl group; alternatively, a 2,6-dimethylphenyl group; alternatively, a 2,6-diethylphenyl group; alternatively, a 2,6-diisopropylphenyl group; alternatively, a 2,4,6-trimethylphenyl group; alternatively, a 2,6-difluorophenyl group; alternatively, a 2,6-dichlorophenyl group; alternatively, a 2,6-dibromophenyl group; alternatively, a 2,4,6-tribromophenyl group; alternatively, a 2,4-dibromo-6-chlorophenyl group; alternatively, a 2,6-dimethyl-6-bromophenyl group; or alternatively, a 2,6-dibromo-6-methylphenyl group.

Generally, $R^{12}$ of the phenanthroline imines and the phenanthroline imine first metal salt complexes can be hydrogen or an organyl group; alternatively, hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In any aspect and/or embodiment disclosed herein, the $R^{12}$ organyl groups of the phenanthroline imines and the phenanthroline imine first metal salt complexes can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the $R^{12}$ organyl groups consisting essentially of inert functional groups, of the phenanthroline imines and the phenanthroline imine first metal salt complexes can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^{12}$ hydrocarbyl groups of the phenanthroline imines and the phenanthroline imine first metal salt complexes can be a $C_1$ to $C_{20}$, a $C_1$ to $C_{15}$, a $C_1$ to $C_{10}$, or a $C_1$ to $C_5$ hydrocarbyl group.

In any aspect and/or embodiment disclosed herein, the $R^{12}$ hydrocarbyl group of any phenanthroline imine and any phenanthroline imine first metal salt complex described herein can be an alkyl group, a cycloalkyl group, a substituted cycloalkyl group, an aryl group, a substituted aryl group, an aralkyl group, or a substituted aralkyl group. In some embodiments, the $R^{12}$ hydrocarbyl group of any phenanthroline imine and any phenanthroline imine first metal salt complex described herein can be an alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, the $R^{12}$ hydrocarbyl group of any phenanthroline imine and any phenanthroline imine first metal salt complex described herein can be an alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect or embodiment disclosed herein, each alkyl group which can be utilized as $R^{12}$ of the phenanthroline imines and the phenanthroline imine first metal salt complexes can be a $C_1$ to $C_{20}$, a $C_1$ to $C_{10}$, or a $C_1$ to $C_5$ alkyl group. In any aspect or embodiment disclosed herein, each cycloalkyl group which can be utilized as $R^{12}$ of the phenanthroline imines and the phenanthroline imine first metal salt complexes can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^{12}$ can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^{12}$ of the phenanthroline imines and the phenanthroline imine first metal salt complexes can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^{12}$ can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^{12}$ of the phenanthroline imines and the phenanthroline imine first metal salt complexes can be a $C_7$ to $C_{20}$, a $C_7$ to $C_{15}$, or a $C_7$ to $C_{10}$ aralkyl group. In any aspect or embodiment disclosed herein, each substituted aralkyl group which can be utilized as $R^{12}$ of the phenanthroline imines and the phenanthroline imine first metal salt complexes can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or a substituted aralkyl group (general or specific) can be a hydrocarbyl group. Substituent hydrocarbyl groups (general and specific) are independently disclosed herein. These substituent hydrocarbyl groups can be utilized without limitation to further describe the substituted cycloalkyl groups, the substituted aryl groups, or the substituted aralkyl groups which can be utilized as $R^{12}$ of the phenanthroline imines and the phenanthroline imine first metal salt complexes.

In any aspect or embodiment disclosed herein, $R^{12}$ of any phenanthroline imine and any phenanthroline imine first metal salt complex described herein can be hydrogen, a methyl group, an ethyl group, an n-propyl (1-propyl) group, an iso-propyl (2-propyl) group, a tert-butyl (2-methyl-2-propyl) group, a neopentyl (2,2-dimethyl-1-propyl) group, or a phenyl group; alternatively, hydrogen, a methyl group, an ethyl group, an n-propyl (1-propyl) group, an iso-propyl (2-propyl) group, or a phenyl group; alternatively, a methyl group, an ethyl group, an n-propyl (1-propyl) group, or an iso-propyl (2-propyl) group; alternatively, hydrogen; alternatively, a methyl group; alternatively, an ethyl group; alternatively, an n-propyl (1-propyl) group; alternatively, an iso-propyl (2-propyl) group; alternatively, a tert-butyl (2-methyl-2-propyl) group; alternatively, a neopentyl (2,2-dimethyl-1-propyl) group; or alternatively, a phenyl group.

In an embodiment, the phenanthroline imine or the phenanthroline imine of the phenanthroline imine first metal salt complex can comprise, can consist essentially of, or can be, a 2-(hydrocarbylimine)-1,10-phenanthroline, a 2-[(hydrocarbylimine)hydrocarbyl]-1,10-phenanthroline, a 2-(arylimine)-1,10-phenanthroline, a 2-[(arylimine)hydrocarbyl]-1,10-phenanthroline, a 2-(substituted arylimine)-1,10-phenanthroline, or a 2-[(substituted arylimine)hydrocarbyl]-1,10-phenanthroline; alternatively, a 2-(hydrocarbylimine)-1,10-phenanthroline; alternatively, a 2-[(hydrocarbylimine)hydrocarbyl]-1,10-phenanthroline; alternatively, a 2-(arylimine)-1,10-phenanthroline; alternatively, a 2-[(arylimine)hydrocarbyl]-1,10-phenanthroline; alternatively, a 2-(substituted arylimine)-1,10-phenanthroline; or alternatively, a 2-[(substituted arylimine)hydrocarbyl]-1,10-phenanthroline.

In an embodiment, the phenanthroline imine or the phenanthroline imine of the phenanthroline imine first metal salt complex can comprise, can consist essentially of, or can be, a 2-(2,6-disubstituted phenylimine)-1,10-phenanthroline, a 2-[(2,6-disubstituted phenylimine)alkyl]-1,10-phenanthroline, a 2-[(2,6-disubstituted phenylimine)phenyl]-1,10-phenanthroline, a 2-(2,4,6-trisubstituted phenylimine)-1,10-phenanthroline, a 2-[(2,4,6-trisubstituted phenylimine)alkyl]-1,10-phenanthroline, or a 2-[(2,4,6-trisubstituted phenylimine)phenyl]-1,10-phenanthroline; alternatively, a 2-(2,6-disubstituted phenylimine)-1,10-phenanthroline; alternatively, a 2-[(2,6-disubstituted phenylimine)alkyl]-1,10-phenanthroline; alternatively, a 2-[(2,6-disubstituted phenylimine)phenyl]-1,10-phenanthroline; alternatively, a 2-(2,4,6-trisubstituted phenylimine)-1,10-phenanthroline; alternatively, a 2-[(2,4,6-trisubstituted phenylimine)alkyl]-1,10-phenanthroline; or alternatively, a 2-[(2,4,6-trisubstituted phenylimine)phenyl]-1,10-phenanthroline. Each substituent of a 2-(2,6-disubstituted phenylimine)-1,10-phenanthroline, a 2-[(2,6-disubstituted phenylimine)alkyl]-1,10-phenanthroline, a 2-[(2,6-disubstituted phenylimine)phenyl]-1,10-phenanthroline, a 2-(2,4,6-trisubstituted phenylimine)-1,10-phenanthroline, a 2-[(2,4,6-trisubstituted phenylimine)alkyl]-1,10-phenanthroline, or a 2-[(2,4,6-trisubstituted phenylimine)phenyl]-1,10-phenanthroline can be an alkyl group or a halo group; alternatively, an alkyl group; or alternatively, a halo group. Substituent alkyl groups (general and specific) and halo group are independently disclosed herein. These substituent alkyl groups and halo groups can be utilized without limitation to further describe the substituents of the phenanthroline imines or the phenanthroline imines of the phenanthroline imine first metal salt complexes.

In an embodiment, the phenanthroline imine or the phenanthroline imine of the phenanthroline imine first metal salt complex can comprise, can consist essentially of, or can be, a 2-(2,6-dialkylphenylimine)-1,10-phenanthroline, a 2-[(2,6-dialkylphenylimine)alkyl]-1,10-phenanthroline, a 2-[(2,6-dialkylphenylimine)phenyl]-1,10-phenanthroline, a 2-(2,4,6-trialkylphenylimine)-1,10-phenanthroline, a 2-[(2,4,6-trialkylphenylimine)alkyl]-1,10-phenanthroline, a 2-[(2,4,6-trialkylphenyl-imine)phenyl]-1,10-phenanthroline, a 2-(2,6-dihalophenylimine)-1,10-phenanthroline, a 2-[(2,6-dihalo-phenylimine)alkyl]-1,10-phenanthroline, a 2-[(2,6-dihalophenylimine)phenyl]-1,10-phenanthroline, 2-(2,4,6-trihalophenylimine)-1,10-phenanthroline, a 2-(2,6-dialkyl-4-halophenylimine)-1,10-phenanthroline, or a 2-(2,6-dihalo-4-alkyl-phenylimine)-1,10-phenanthroline; alternatively, a 2-(2,6-dialkylphenylimine)-1,10-phenanthroline; alternatively, a 2-[(2,6-dialkylphenylimine)alkyl]-1,10-phenanthroline; alternatively, a 2-[(2,6-dialkylphenylimine)phenyl]-1,10-phenanthroline; alternatively, a 2-(2,4,6-trialkylphenylimine)-1,10-phenanthroline; alternatively, a 2-[(2,4,6-trialkylphenylimine)alkyl]-1,10-phenanthroline; alternatively, a 2-[(2,4,6-trialkylphenylimine)phenyl]-1,10-phenanthroline; alternatively, a 2-(2,6-dihalophenylimine)-1,10-phenanthroline; alternatively, a 2-[(2,6-dihalo-phenylimine)alkyl]-1,10-phenanthroline; alternatively, a 2-[(2,6-dihalophenylimine)phenyl]-1,10-phenanthroline; alternatively, 2-(2,4,6-trihalophenylimine)-1,10-phenanthroline; alternatively, a 2-(2,6-dialkyl-4-halophenylimine)-1,10-phenanthroline; or alternatively, a 2-(2,6-dihalo-4alkyl-phenylimine)-1,10-phenanthroline. Substituent alkyl groups (general and specific) and halo groups are independently disclosed herein. These substituent alkyl groups and halo groups can be utilized without limitation to further describe the substituents of the phenanthroline imines or the phenanthroline imines of the phenanthroline imine first metal salt complexes.

In a non-limiting embodiment, the phenanthroline imine or the phenanthroline imine of the phenanthroline imine first metal salt complex can comprise, can consist essentially of, or can be, 2-(2,6-difluorophenylimine)-1,10-phenanthroline, 2-(2,6-dichlorophenylimine)-1,10-phenanthroline, 2-(2,6-dibromophenylimine)-1,10-phenanthroline, 2-(2,6-dimethylphenylimine)-1,10-phenanthroline, 2-(2,6-diethylphenylimine)-1,10-phenanthroline, 2-(2,6-diisopropylphenylimine)-1,10-phenanthroline, 2-[(2,6-difluorophenylimine)methyl]-1,10-phenanthroline, 2-[(2,6-dichlorophenylimine)methyl]-1,10-phenanthroline, 2-[(2,6-dibromophenylimine)methyl]-1,10-phenanthroline, 2-[(2,6-dimethylphenylimine)-methyl]-1,10-phenanthroline, 2-[(2,6-diethylphenylimine)methyl]-1,10-phenanthroline, 2-[(2,6-diiso-propylphenylimine)methyl]-1,10-phenanthroline, 2-[(2,6-diethylphenylimine)ethyl]-1,10-phenanthroline, 2-[(2,6-diethylphenylimine)-n-propyl]-1,10-phenanthroline, 2-[(2,6-diethylphenylimine)iso-propyl]-1,10-phenanthroline, 2-[(2,4,6-tribromophenylimine)methyl]-1,10-phenanthroline, 2-[(2,4,6-trimethylphenyl-imine)methyl]-1,10-phenanthroline, 2-[(2,6-dimethyl-4-bromophenylimine)methyl]-1,10-phenanthroline, 2-[(2,6-dibromo-4-methylphenylimine)methyl]-1,10-phenanthroline, 2-[(2,6-dibromo-4-chlorophenyl-imine)methyl]-1,10-phenanthroline, 2-[(2,6-dimethylphenylimine)phenyl]-1,10-phenanthroline, 2-[(2,6-diethylphenylimine)phenyl]-1,10-phenanthroline, and 2-[(2,6-diisopropylphenylimine)phenyl]-1,10-phenanthroline.

The processes described herein can utilize a metal salt, a first metal salt (as a part of any heteroatomic ligand metal salt complex comprising a heteroatomic ligand complexed to a first metal salt disclosed herein), and/or a second metal salt. In any aspect and/or embodiments utilizing a metal salt, a first metal salt (as a part of any heteroatomic ligand metal salt complex comprising a heteroatomic ligand complexed to a first metal salt disclosed herein), and/or a second metal salt, the metal salt, first metal salt, and second metal salt are independent of each other and can be the same or different: alternatively, the same; or alternatively different. Generally, the metal salt, the first metal salt (as a part of any heteroatomic ligand metal salt complex comprising a heteroatomic ligand complexed to a first metal salt disclosed herein), and/or the second metal salt, can have the formula $MX_n$. Within the formula of the metal salt having the formula $MX_n$ (whether it is the metal salt, the first metal salt, and/or a second metal salt), M represents the metal atom, X represents a monoanionic species, and n represents the number of monoanionic species (or the metal oxidation state). Generally, the metal, the monoanionic species, X, and the number of anionic species (or the metal oxidation state), n, are independent elements of the metal salt (whether it is the metal salt, the first metal salt, and/or a second metal salt) and are independently described herein. The metal salt having the formula $MX_n$ (whether it is the metal salt, the first metal salt, and/or the second metal salt) can be described utilizing any aspect and/or embodiment of the metal described herein, any aspect or embodiment of the monoanionic specie described herein, and any aspect and/or embodiment of the number of monoanionic species (or metal oxidation state) described herein.

Generally, the metal of the metal salt (whether it is the metal salt, the first metal salt, and/or the second metal salt) independently can be a group 8 or group 9 metal; alternatively, a group 8 metal; or alternatively, a group 9 metal. In some embodiments, metal of the metal salt which can be utilized as the metal salt, the first metal salt (as a part of any heteroatomic ligand metal salt complex comprising a heteroatomic ligand complexed to a first metal salt described herein), and/or the second metal salt independently can be iron (Fe) or cobalt (Co); alternatively, iron (Fe); or alternatively, cobalt (Co). Generally, the oxidation state of the metal of the metal salt and/or number, n, of monoanionic species, X, of the metal salt which can be utilized as the metal salt, the first metal salt (as a part of any heteroatomic ligand metal salt complex comprising a heteroatomic ligand complexed to a first metal salt described), and/or the second metal salt independently can be any positive integer that corresponds to an oxidation state available to the metal atom. In an aspect, the oxidation state of the metal of the metal salt and/or number, n, of monoanionic species, X, of the metal salt which can be utilized as the metal salt, the first metal salt (as a part of any heteroatomic ligand metal salt complex comprising a heteroatomic ligand complexed to a first metal salt described herein), and/or the second metal salt independently can be 1, 2 or 3; alternatively, 2 or 3; alternatively, 1; alternatively, 2; or alternatively, 3.

Generally, the monoanionic specie, X, of the metal salt, the first metal salt (as a part of any heteroatomic ligand metal salt complex comprising a heteroatomic ligand complexed to a first metal salt described herein), and/or the second metal salt independently can be any monoanionic specie. In an aspect, the monoanionic specie, X, can be a halide, a carboxylate, a β-diketonate, a hydrocarboxide, a nitrate, or a chlorate; alternatively, a halide, a carboxylate, a β-diketonate, or a hydrocarboxide; or alternatively, a halide, a carboxylate, or a β-diketonate. In any aspect and/or embodiment, the hydrocarboxide can be an alkoxide, an aryloxide, or an aralkoxide. Generally, hydrocarboxides (and subdivisions of hydrocarboxide) are the anion analogues of the hydrocarboxy group. In other aspects, the monoanionic specie, X, of the metal salt, the first metal salt (as a part of any heteroatomic ligand metal salt complex comprising a heteroatomic ligand complexed to a first metal salt described herein), and/or the second metal salt independently can be a halide, a carboxylate, a β-diketonate, or an alkoxide; alternatively, a carboxylate; alternatively, a β-diketonate; alternatively, a hydrocarboxide; alternatively, an alkoxide; or alternatively, an aryloxide.

Generally, each halide monoanionic specie, X, of the metal salt, the first metal salt (as a part of any heteroatomic ligand metal salt complex comprising a heteroatomic ligand complexed to a first metal salt described herein), and/or the second metal salt independently can be fluorine, chlorine, bromine, or iodine; or alternatively, chlorine, bromine, or iodine. In an aspect, each halide monoanionic specie, X, of the metal salt, the first metal salt (as a part of any heteroatomic ligand metal salt complex comprising a heteroatomic ligand complexed to a first metal salt described herein), and/or the second metal salt independently can be chlorine; alternatively, bromine; or alternatively, iodine.

Generally, each carboxylate monoanionic specie, X, of the metal salt, the first metal salt (as a part of any heteroatomic ligand metal salt complex comprising a heteroatomic ligand complexed to a first metal salt described herein), and/or the second metal salt independently can be a $C_1$ to $C_{20}$ or a $C_1$ to $C_{10}$ carboxylate. In an aspect, each carboxylate of the metal salt, the first metal salt (as a part of any heteroatomic ligand metal salt complex comprising a heteroatomic ligand complexed to a first metal salt described herein), and/or the second metal salt independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, or a decanoate. In some aspects, each carboxylate monoanionic specie, X, of the metal salt, the first metal salt (as a part of any heteroatomic ligand metal salt complex comprising a heteroatomic ligand complexed to a first metal salt described herein), and/or the second metal salt independently can be acetate, propionate, n-butyrate, valerate (n-pentanoate), neopentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, or caprate (n-decanoate; alternatively, n-heptanoate; alternatively, caprylate (n-octanoate); or alternatively, 2-ethylhexanoate. In some aspects, the carboxylate can be triflate (trifluoroacetate).

Generally, each β-diketonate monoanionic specie, X, of the metal salt, the first metal salt (as a part of any heteroatomic ligand metal salt complex comprising a heteroatomic ligand complexed to a first metal salt described herein), and/or the second metal salt independently can be a $C_1$ to $C_{20}$ or a $C_1$ to $C_{10}$ β-diketonate. In an aspect, each β-diketonate monoanionic specie, X, of the metal salt, the first metal salt (as a part of any heteroatomic ligand metal salt complex comprising a heteroatomic ligand complexed to a first metal salt described herein), and/or the second metal salt independently can be acetylacetonate (i.e., 2,4-pentanedionate), hexafluoroacetylacetonate (i.e., 1,1,1,5,5,5-hexafluoro-2,4-pentanedionate), or benzoylacetonate; alternatively, acetylacetonate; alternatively, hexafluoroacetylacetone; or alternatively, benzoylacetonate.

Generally, each hydrocarboxide monoanionic specie, X, of the metal salt, the first metal salt (as a part of any heteroatomic ligand metal salt complex comprising a heteroatomic ligand complexed to a first metal salt described herein), and/or the second metal salt independently can be any $C_1$ to $C_{20}$ or $C_1$ to $C_{10}$ hydrocarboxide. In an aspect, each hydrocarboxide monoanionic specie, X, of the metal salt, the first metal salt (as a part of any heteroatomic ligand metal salt complex comprising a heteroatomic ligand complexed to a first metal salt described herein), and/or the second metal salt independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide monoanionic specie, X, of the metal salt, the first metal salt (as a part of any heteroatomic ligand metal salt complex comprising a heteroatomic ligand complexed to a first metal salt described herein), and/or the second metal salt independently can be methoxide, ethoxide, a propoxide, or a butoxide. In some aspects, each alkoxide monoanionic specie, X, of the metal salt, the first metal salt (as a part of any heteroatomic ligand metal salt complex comprising a heteroatomic ligand complexed to a first metal salt described herein), and/or the second metal salt independently can be methoxide, ethoxide, isopropoxide, or tert-butoxide; alternatively, methoxide; alternatively, an ethoxide; alternatively, an iso-propoxide; or alternatively, a tert-butoxide. In an aspect, each aryloxide monoanionic specie, X, of the metal salt, the first metal salt (as a part of any heteroatomic ligand metal salt complex comprising a heteroatomic ligand complexed to a first metal salt described herein), and/or the second metal salt independently can be phenoxide.

In any aspect or embodiment, the metal salt, the first metal salt (as a part of any heteroatomic ligand metal salt complex comprising a heteroatomic ligand complexed to a first metal salt described herein), and/or the second metal salt independently can comprise, can consist essentially of, or can be an iron salt, a cobalt salt, or a combination thereof; alternatively, an iron salt; or alternatively, a cobalt salt. In an embodiment, the metal salt, the first metal salt (as a part of any heteroatomic ligand metal salt complex comprising a heteroatomic ligand complexed to a first metal salt described herein), and/or the second metal salt independently can comprise, can consist essentially of, or can be an iron halide, a cobalt halide, an iron β-diketonate, a cobalt β-diketonate, an iron carboxylate, a cobalt carboxylate or any combination thereof; alternatively, an iron halide, an iron β-diketonate, an iron carboxylate, or any combination thereof; or alternatively, an cobalt halide, an cobalt β-diketonate, an cobalt carboxylate, or any combination thereof. In any aspect or embodiment, the metal salt, the first metal salt (as a part of any heteroatomic ligand metal salt complex comprising a heteroatomic ligand complexed to a first metal salt described herein), and/or the second metal salt independently can comprise, can consist essentially of, or can be, iron(II) fluoride, cobalt(II) fluoride, iron(III) fluoride, cobalt(III) fluoride, iron(II) bromide, cobalt(II) bromide, iron(III) bromide, cobalt(III) bromide, iron(II) iodide, cobalt(II) iodide, iron(III) iodide, cobalt(III) iodide, iron(II) acetate, cobalt(II) acetate, iron(III) acetate, iron(III) acetate, iron(II) acetylacetonate, cobalt(II) acetylacetonate, iron(III) acetylacetonate, cobalt(III) acetylacetonate, iron(II) 2-ethylhexanoate, cobalt (II) 2-ethylhexanoate, iron(III) 2-ethylhexanoate, cobalt(III) 2-ethylhexanoate, iron(II) triflate, cobalt(II) triflate, iron(III) triflate, cobalt(III) triflate, iron(II) nitrate, cobalt(II) nitrate, iron(III) nitrate, cobalt(III) nitrate, or any combination thereof; alternatively, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, iron(II) nitrate, iron(III) nitrate, or any combination thereof; alternatively, iron(II) chloride, cobalt(II) chloride, iron(III) chloride, cobalt(III) chloride, iron(II) acetate, cobalt(II) acetate, iron(III) acetate, cobalt(III) acetate, iron(II) acetylacetonate, cobalt(II) acetylacetonate, iron(III) acetylacetonate, cobalt(III) acetylacetonate, or any combination thereof; alternatively, iron(II) chloride, iron(III) chloride, iron(II) acetate, iron(III) acetate, iron(II) acetylacetonate, iron(III) acetylacetonate, or any combination thereof; alternatively, iron(II) chloride, cobalt(II) chloride, iron(III) chloride, cobalt(III) chloride, iron(II) acetylacetonate, cobalt(II) acetylacetonate, iron(III) acetylacetonate, cobalt(III) acetylacetonate, or any combination thereof; alternatively, iron (II) chloride, iron(III) chloride, iron(II) acetylacetonate, iron(III) acetylacetonate, or any combination thereof; alternatively, iron(II) chloride; alternatively, iron(III) chloride; alternatively, iron(II) acetylacetonate; or alternatively, iron (III) acetylacetonate.

In some aspects, the heteroatomic ligand metal salt complex comprising a heteroatomic ligand complexed to a first metal salt can have a structure selected from the group consisting of ADIFe I
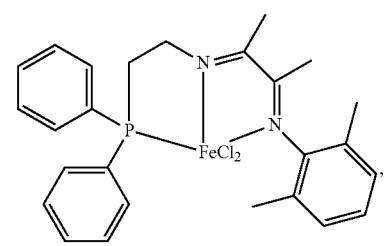
ADIFe II
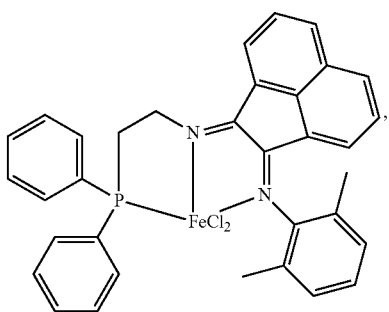
ADIFe III
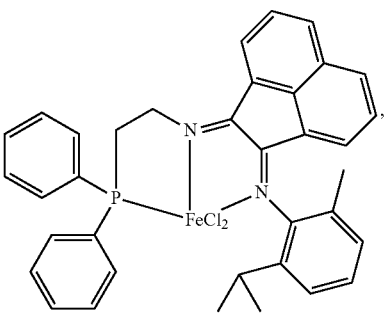
ADIFe IV
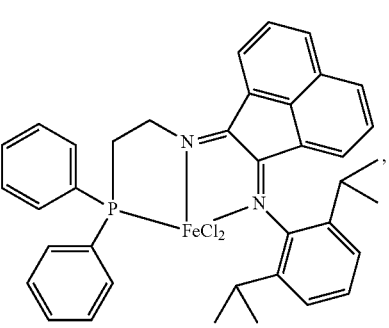
ADIFe V
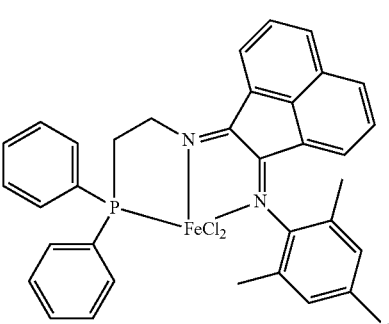
-continued
ADIFe VI
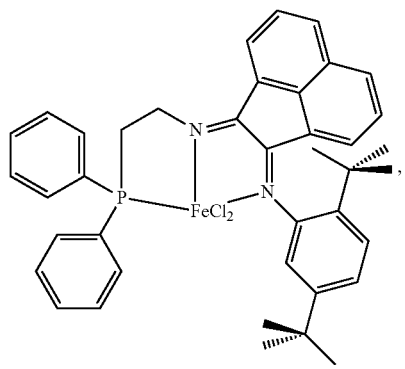
ADIFe VII
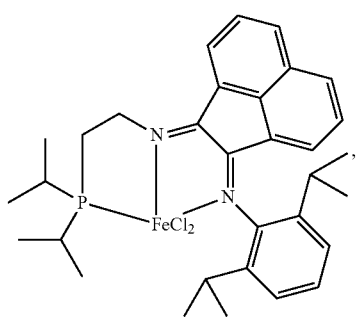
ADIFe VIII
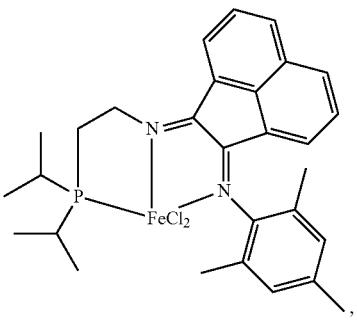
ADIFe IX
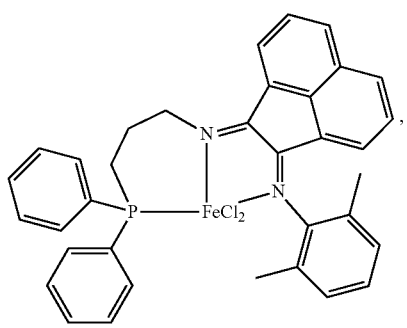

ADIFe X

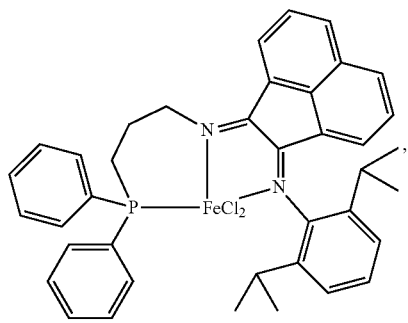

ADIFe XII

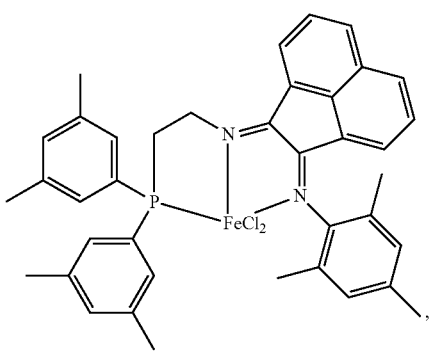

ADIFe XIII

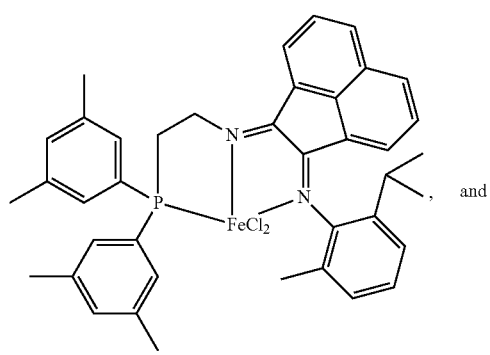

ADIFe XIV

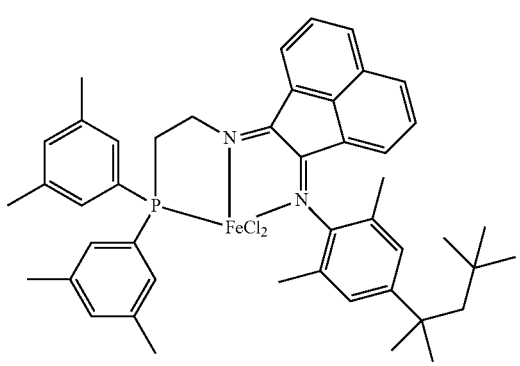

In other embodiments, the heteroatomic ligand metal salt complex comprising a heteroatomic ligand complexed to a first metal salt can be selected from the group consisting of 2,6-bis[(phenylimine) methyl]pyridine iron dichloride, 2,6-bis[(2-methylphenylimine)methyl]pyridine iron dichloride, 2,6-bis[(2-ethylphenylimine)methyl]pyridine iron dichloride, 2,6-bis[(2-isopropylphenylimine)methyl]-pyridine iron dichloride, 2,6-bis[(2,4-dimethylphenylimine)methyl]pyridine iron dichloride, 2,6-bis[(2,6-diethylphenylimine) methyl]pyridine iron dichloride, 2-[(2,4,6-trimethylphenylimine)methyl]-6-[(4-methylphenylimine)methyl] pyridine iron dichloride, 2-[(2,4,6-trimethylphenylimine) methyl]-6-[(3,5-dimethylphenylimine)methyl]pyridine iron dichloride, and 2-[(2,4,6-trimethylphenylimine)methyl]-6-[(4-t-butylphenylimine)methyl]pyridine iron dichloride. In other embodiments, the heteroatomic ligand metal salt complex comprising a heteroatomic ligand complexed to a first metal salt can be selected from the group consisting of 2-[(2,6-difluorophenylimine)-1,10-phenanthroline iron dichloride, 2-[(2,6-dichlorophenylimine)-1,10-phenanthroline iron dichloride, 2-[(2,6-dibromophenylimine)-1,10-phenanthroline iron dichloride, 2-[(2,6-dimethylphenylimine)-1,10-phenanthroline iron dichloride, 2-[(2,6-diethylphenylimine)-1,10-phenanthroline iron dichloride, 2-[(2,6-diisopropylphenylimine)-1,10-phenanthroline iron dichloride, 2-[(2,6-difluorophenylimine)methyl]-1,10-phenanthroline iron dichloride, 2-[(2,6-dichlorophenylimine)methyl]-1,10-phenanthroline iron dichloride, 2-[(2,6-dibromophenyl-imine)methyl]-1,10-phenanthroline iron dichloride, 2-[(2,6-dimethylphenylimine)methyl]-1,10-phenanthroline iron dichloride, 2-[(2,6-diethylphenylimine) methyl]-1,10-phenanthroline iron dichloride, 2-[(2,6-diisopropylphenylimine)methyl]-1,10-phenanthroline iron dichloride, 2-[(2,6-diethylphenyl-imine)ethyl]-1,10-phenanthroline iron dichloride, 2-[(2,6-diethylphenylimine)-n-propyl]-1,10-phenanthroline iron dichloride, 2-[(2,6-diethylphenylimine)iso-propyl]-1,10-phenanthroline iron dichloride, 2-[(2,4,6-tribromophenylimine)methyl]-1,10-phenanthroline iron dichloride, 2-[(2,4,6-trimethylphenylimine)methyl]-1,10-phenanthroline iron dichloride, 2-[(2,6-dimethyl-4-bromophenyl-imine)methyl]-1,10-phenanthroline iron dichloride, 2-[(2,6-dibromo-4-methylphenylimine)methyl]-1,10-phenanthroline iron dichloride, 2-[(2,6-dibromo-4-chlorophenylimine)methyl]-1,10-phenanthroline iron dichloride, 2-[(2,6-dimethylphenylimine)phenyl]-1,10-phenanthroline iron dichloride, 2-[(2,6-diethyl-phenylimine)phenyl]-1,10-phenanthroline iron dichloride, and 2-[(2,6-diisopropylphenylimine)phenyl]-1,10-phenanthroline iron dichloride.

It should be noted that while not explicitly shown or stated, the metal salt, the heteroatomic ligand metal salt complex (comprising a heteroatomic ligand complexed to a first metal salt), and/or the second metal salt can further comprise a neutral ligand. While the neutral ligand is not provided in the names, structures, or formulas provided herein, it should be understood that the metal salt, the heteroatomic ligand metal salt complex (comprising a heteroatomic ligand complexed to a first metal salt), and/or the second metal salt names and depictions do not limit the metal salt, the heteroatomic ligand metal salt complex (comprising a heteroatomic ligand complexed to a first metal salt), and/or the second metal salt names and depictions to those not having a neutral ligand. In fact, the metal salt, the heteroatomic ligand metal salt complex (comprising a heteroatomic ligand complexed to a first metal salt), and/or the second metal salt which can be utilized in any aspect disclosed herein or any embodiment disclosed herein can include a neutral ligand and that these names and depictions provided herein do not limit the metal salt, the heteroatomic ligand metal salt complex (comprising a heteroatomic ligand complexed to a first metal salt), and/or the second metal salt to those which do not comprise a neutral ligand regardless of the language utilized to describe the metal salts or metal salt complexes. Neutral ligands are provided herein and can be utilized without limitation to further describe the metal salt, the heteroatomic ligand metal salt complex (comprising a heteroatomic ligand complexed to a first metal salt), and/or the second metal salt.

Generally, the neutral ligand, if present, can be any neutral ligand that forms an isolatable compound with the metal salt, the heteroatomic ligand metal salt complex (comprising a heteroatomic ligand complexed to a first metal salt), and/or the second metal salt. In an aspect, each neutral ligand independently can be a nitrile, an ether, or an amine; alternatively, a nitrile; alternatively, an ether; or alternatively, an amine. The number of neutral ligands of the metal salt, the heteroatomic ligand metal salt complex (comprising a heteroatomic ligand complexed to a first metal salt), and/or the second metal salt can be any number that forms an isolatable compound with the metal salt and/or the heteroatomic ligand metal salt complex. In an aspect, the number of neutral ligands of the metal salt, the heteroatomic ligand metal salt complex (comprising a heteroatomic ligand complexed to a first metal salt), and/or the second metal salt can be 1, 2, 3, 4, 5, or 6; alternatively, 1; alternatively, 2; alternatively, 3; alternatively, 4; alternatively, 5; or alternatively, 6.

Generally, each nitrile ligand which can be utilized as the neutral ligand independently can be a $C_2$ to $C_{20}$ nitrile; or alternatively, a $C_2$ to $C_{10}$ nitrile. In an embodiment, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand which can be utilized as the neutral ligand independently can be a $C_2$ to $C_{40}$ ether; alternatively, a $C_2$ to $C_{30}$ ether; or alternatively, a $C_2$ to $C_{20}$ ether. In an embodiment, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; alternatively, tetrahydrofuran, a dihydrofuran, 1,3-dioxolane, tetrahydropyran, a dihydropyran, a pyran, a dioxane, or any combination thereof; alternatively furan, benzofuran, isobenzofuran, isobenzofuran, dibenzofuran, or any combination thereof; alternatively diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, isobenzofuran; alternatively, dibenzofuran; alternatively, diphenyl ether; or alternatively, a ditolyl ether.

In an aspect, each amine ligand which can be utilized as the non-α-diimine neutral ligand independently can be a monohydrocarbylamine, a dihydrocarbylamine, a trihydrocarbylamine, or any combination thereof; alternatively, a monohydrocarbylamine; alternatively, a dihydrocarbylamine; or alternatively, a trihydrocarbylamine. Monohydrocarbylamines which can be utilized as the non-α-diimine neutral ligand can be a $C_1$ to $C_{30}$ monohydrocarbylamine, a $C_1$ to $C_{20}$ monohydrocarbylamine, a $C_1$ to $C_{10}$ monohydrocarbylamine, or a $C_1$ to $C_5$ monohydrocarbylamine. Dihydrocarbylamines which can be utilized as the non-α-diimine neutral ligand can be a $C_2$ to $C_{30}$ dihydrocarbylamine, a $C_2$ to $C_{20}$ dihydrocarbylamine, a $C_2$ to $C_{10}$ dihydrocarbylamine, or a $C_2$ to $C_5$ dihydrocarbylamine. Trihydrocarbylamines which can be utilized as the non-α-diimine neutral ligand can be a $C_3$ to $C_{30}$ trihydrocarbylamine, a $C_3$ to $C_{20}$ trihydrocarbylamine, or a $C_3$ to $C_{10}$ trihydrocarbylamine. Hydrocarbyl groups (general and specific) are disclosed herein (e.g., as substituent groups, among other places) and can be utilized without limitation to further describe the monohydrocarbylamines, dihydrocarbylamines, and/or trihydrocarbylamines which can be utilized as the neutral ligand. Generally, each hydrocarbyl group of the dihydrocarbylamine (or trihydrocarbylamine) is independent of each other and can be the same: or alternatively, can be different. In a non-limiting embodiment, the monohydrocarbylamine, which can be utilized as the non-α-diimine neutral ligand can be, can comprise, or can consist essentially of, methyl amine, ethyl amine, propyl amine, butyl amine, or any combination thereof; alternatively, methyl amine; alternatively, ethyl amine; alternatively, propyl amine; or alternatively, butyl amine. In some embodiments, the dihydrocarbylamine, which can be utilized as the non-α-diimine neutral ligand can be, can comprise, or can consist essentially of, dimethyl amine, diethyl amine, dipropyl amine, dibutylamine, or any combination thereof; alternatively, dimethyl amine; alternatively, diethyl amine; alternatively, dipropyl amine; or alternatively, dibutylamine. In some embodiments, the trihydrocarbylamine, which can be utilized as the non-α-diimine neutral ligand can be, can comprise, or can consist essentially of, trimethyl amine, triethyl amine, tripropyl amine, tributyl amine, or any combination thereof; alternatively, trimethyl amine; alternatively, triethyl amine; alternatively, tripropyl amine; or alternatively, tributyl amine.

In an aspect, the organoaluminum compound which can be utilized in the processes described herein can comprise an aluminoxane, an alkylaluminum compound, or a combination thereof; alternatively, an aluminoxane; or alternatively, an alkylaluminum compound. In an aspect, the alkylaluminum compound can be a trialkylaluminum, an alkylaluminum halide, an alkylaluminum alkoxide, or any combination thereof. In some aspects, the alkylaluminum compound can be a trialkylaluminum, an alkylaluminum halide, or any combination thereof; alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide; or alternatively, an alkylaluminum alkoxide. In an embodiment, the organoaluminum compound (regardless of whether it is an aluminoxane, an alkylaluminum compound, or subspecies or individuals contained therein) can be substantially devoid of (or alternatively, devoid of) β,δ-branched organyl groups (or alkyl group) and β,γ-branched organyl groups (or alkyl groups). Generally, substantially devoid of β,δ-branched organyl groups (or alkyl group) and β,γ-branched organyl groups (or alkyl group) can be taken to mean that less than 5, 4, 3, 2, 1, 0.75, 0.5, 0.25, or 0.1 mole percent of the organoaluminum organyl groups are β,δ-branched organyl groups (or alkyl groups) and β,γ-branched organyl groups (or alkyl groups).

In an aspect, each alkyl group of any organoaluminum compound or any alkylaluminum compound disclosed herein (e.g., trialkylaluminum, alkylaluminum halide, alkylaluminum alkoxide or aluminoxane) independently can be a $C_1$ to $C_{20}$ alkyl group, a $C_1$ to $C_{10}$ alkyl group, or a $C_1$ to $C_6$ alkyl group. In an aspect, each alkyl group of any organoaluminum compound or any alkylaluminum compound disclosed herein (e.g., trialkylaluminum, alkylaluminum halide, alkylaluminum alkoxide, or aluminoxane) independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some aspects, each alkyl group of any organoaluminum compound or any alkylaluminum compound disclosed herein (e.g., trialkylaluminum, alkylaluminum halide, alkylaluminum alkoxide or aluminoxane) independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group. In an embodiment, the organoaluminum compound (regardless of whether it is an aluminoxane, an alkylaluminum compound, or a subspecies or individuals contained therein) can be substantially devoid (or alternatively, devoid of) of β,δ-branched alkyl groups and β,γ-branched alkyl groups. Generally, substantially devoid of β,δ-branched alkyl groups and β,γ-branched alkyl groups can be taken to mean that less than 5, 4, 3, 2, 1, 0.75, 0.5, 0.25, or 0.1 mole percent of the alkyl groups are β,δ-branched alkyl groups and β,γ-branched alkyl groups.

In an aspect, each halide of any alkylaluminum halide disclosed herein independently can be chloride, bromide, or iodide. In some aspects, each halide of any alkylaluminum halide disclosed herein can be chloride or bromide; or alternatively, chloride.

In an aspect, each alkoxide group of any alkylaluminum alkoxide disclosed herein independently can be a $C_1$ to $C_{20}$ alkoxy group, a $C_1$ to $C_{10}$ alkoxy group, or a $C_1$ to $C_6$ alkoxy group. In an aspect, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some aspects, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting aspect, the trialkylaluminum compound can comprise, can consist essentially of, or can be, trimethylaluminum, triethylaluminum, tripropylaluminum, tributylaluminum, trihexylaluminum, trioctylaluminum, or mixtures thereof. In some non-limiting aspects, the trialkylaluminum compound can comprise, can consist essentially of, or can be, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting aspects, the trialkylaluminum compound can comprise, can consist essentially of, or can be, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting aspect, the alkylaluminum halide can comprise, can consist essentially of, or can be, diethylaluminum chloride, diethylaluminum bromide, ethylaluminum dichloride, ethylaluminum sesquichloride, and mixtures thereof. In some non-limiting aspects, the alkylaluminum halide can comprise, can consist essentially of, or can be diethylaluminum chloride, ethylaluminum dichloride, ethylaluminum sesquichloride, and mixtures thereof; or alternatively, diethylaluminum chloride; alternatively, diethylaluminum bromide; alternatively, ethylaluminum dichloride; or alternatively, ethylaluminum sesquichloride.

In a non-limiting aspect, the aluminoxane can have a repeating unit characterized by the Formula I:

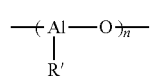

Formula I wherein R' is a linear or branched alkyl group. Alkyl groups for organoaluminum compounds are independently described herein and can be utilized without limitation to further describe the aluminoxanes having Formula I. Generally, n of Formula I is greater than 1; or alternatively, greater than 2. In an aspect, n can range from 2 to 15; or alternatively, from 3 to 10. In an embodiment, R' of the aluminoxane can be substantially devoid (or alternatively, devoid of) of β,δ-branched alkyl groups and β,γ-branched alkyl groups. Generally, substantially devoid of β,δ-branched alkyl groups and β,γ-branched alkyl groups can be taken to mean that less than 5, 4, 3, 2, 1, 0.75, 0.5, 0.25, or 0.1 mole percent of the aluminoxane alkyl groups are β,δ-branched alkyl groups and β,γ-branched alkyl groups.

In a non-limiting aspect, the aluminoxane can be a reaction product of water with an organoaluminum compound. In some embodiments, the organoaluminum compound can have the formula $AlR^{Al}_xH_{3-x}$ where x is an integer from 1 to 3 and each R can be any organyl group, hydrocarbyl group, or alkyl group (alternatively, any organyl group; alternatively, any hydrocarbyl groups; or alternatively, any alkyl group) of the organoaluminum compounds disclosed herein. In some non-limiting embodiments, the organoaluminum having the formula $AlR^{Al}_xH_{3-x}$, of the aluminoxane which can be a reaction product of water with an organoaluminum compound having the formula $AlR^{Al}_xH_{3-x}$, is substantially devoid of (or alternatively, devoid of) β,δ-branched and β,γ-branched $R^{Al}$ groups. Generally, substantially devoid of β,δ-branched and β,γ-branched $R^{Al}$ groups can be taken to mean that less than 5, 4, 3, 2, 1, 0.75, 0.5, 0.25, or 0.1 mole percent of the $R^{Al}$ groups are β,δ-branched and β,γ-branched $R^{Al}$ groups, organyl groups, hydrocarbyl groups, and/or alkyl group; alternatively, organyl groups; alternatively, hydrocarbyl groups; or alternatively, alkyl groups.

In a non-limiting aspect, the aluminoxane can comprise, can consist essentially of, or can be, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butylaluminoxane, 1-pentylaluminoxane, 2-pentylaluminoxane, 3-pentylaluminoxane, iso-pentylaluminoxane, neopentylaluminoxane, or mixtures thereof. In some non-limiting aspects, the aluminoxane can comprise, can consist essentially of, or can be, methylaluminoxane (MAO), a modified methylaluminoxane (MMAO), isobutylaluminoxane, t-butylaluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butylaluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane. In an embodiment, the aluminoxane can be substantially devoid (or alternatively, devoid of) of β,δ-branched alkyl groups and β,γ-branched alkyl groups. Generally, a aluminoxane substantially devoid of β,δ-branched alkyl groups and β,γ-branched alkyl groups can be taken to mean that less than 5, 4, 3, 2, 1, 0.75, 0.5, 0.25, or 0.1 mole percent of the aluminoxane alkyl groups are β,δ-branched alkyl groups and β,γ-branched alkyl groups.

In an aspect, the processes described herein can utilize an organic reaction medium. Generally, the organic reaction medium can act as a solvent and/or a diluent in the processes described herein. In an aspect, the organic reaction medium can comprise, can consist essentially of, or can be, a hydrocarbon, a halogenated hydrocarbon, or a combination thereof; alternatively, a hydrocarbon; or alternatively, a halogenated hydrocarbon(s). In an aspect, hydrocarbons which can be utilized as the organic reaction medium can be an aliphatic hydrocarbon, an aromatic hydrocarbon, or any combination thereof; alternatively, an aliphatic hydrocarbon; or alternatively, an aromatic hydrocarbon. In some aspects, the aliphatic hydrocarbon which can be utilized as the organic reaction medium can comprise, can consist essentially of, or can be, a saturated aliphatic hydrocarbon, an olefinic aliphatic hydrocarbon, or any combination thereof; alternatively, a saturated aliphatic hydrocarbon(s); or alternatively an olefinic aliphatic hydrocarbon(s). In an aspect, halogenated hydrocarbons which can be utilized as the organic reaction medium can be a halogenated aliphatic hydrocarbon, a halogenated aromatic hydrocarbon, or any combination thereof; alternatively, a halogenated aliphatic hydrocarbon; or alternatively, a halogenated aromatic hydrocarbon.

In an aspect, the hydrocarbon, aliphatic hydrocarbon, saturated aliphatic hydrocarbon, or olefinic aliphatic hydrocarbon which can be utilized as the organic reaction medium can comprise, consist essentially of, or can be, a $C_3$ to $C_{18}$, a $C_4$ to $C_{18}$, or a $C_5$ to $C_{10}$ hydrocarbon(s), aliphatic hydrocarbon(s), saturated aliphatic hydrocarbon(s), or olefinic aliphatic hydrocarbon(s). In other aspects, the aliphatic hydrocarbon(s) (saturated or olefinic) which can useful as an organic reaction medium can comprise, can consist essentially of, or can be, a $C_8$ to $C_{18}$, a $C_8$ to $C_{16}$, or alternatively, a $C_{10}$ to $C_{14}$ hydrocarbon(s), aliphatic hydrocarbon(s), saturated aliphatic hydrocarbon(s), or olefinic aliphatic hydrocarbon(s). The hydrocarbon(s), aliphatic hydrocarbon(s), saturated aliphatic hydrocarbon(s), or olefinic hydrocarbon(s) can be cyclic or acyclic and/or can be linear or branched, unless otherwise specified.

Non-limiting examples of suitable hydrocarbon organic reaction mediums that can be utilized singly or in any combination include propane, butane(s), pentane(s), hexane(s), heptane(s), octane(s), decane(s), undecane(s), dodecane(s), tridecane(s), tetradecane(s), pentadecane(s), hexadecane(s), heptadecane(s), octadecane(s), hexene(s), heptene(s), octene(s), nonene(s), decene(s), dodecene(s), tetradecene(s), hexadecene(s), octadecene(s), or any combination thereof; alternatively, propane, butane(s), pentane(s), hexane(s), heptane(s), octane(s), decane(s), undecane(s), dodecane(s), tridecane(s), tetradecane(s), pentadecane(s), hexadecane(s), heptadecane(s), octadecane(s), or any combination thereof; or alternatively, hexene(s), heptene(s), octene(s), nonene(s), decene(s), dodecene(s), tetradecene(s), hexadecene(s), octadecene(s), or any combination thereof. In an aspect, suitable acyclic aliphatic hydrocarbon organic reaction mediums that can be utilized can comprise, or can consist essentially of, propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or any combination thereof. In another aspect, a saturated aliphatic hydrocarbon can comprise, or consist essentially of 1-octane, 1-decane, 1-dodecane, 1-tetradecane, 1-hexadecane, 1-octadecane, or any combination thereof; alternatively, 1-decane, 1-dodecane, 1-tetradecane, or any combination thereof; alternatively, 1-decane; alternatively, 1-dodecane; or alternatively, 1-tetradecane. In an aspect, an olefinic aliphatic hydrocarbon which can be utilized as the organic reaction medium can comprise, can consist essentially of, or can be, an alpha olefin(s); or alternatively, a normal alpha olefin(s). In a non-limiting aspect, the olefinic aliphatic hydrocarbon which can be utilized as the organic reaction medium can be, can comprise, or can consist essentially of, 1-octene, 1-decene, 1-dodecene, 1-tetradecene, 1-hexadecene, 1-octadecene, or any combination thereof; alternatively, 1-decene, 1-dodecene, 1-tetradecene, or any combination thereof; alternatively, 1-decene; alternatively, 1-dodecene; or alternatively, 1-tetradecene. In a non-limiting aspect, the cyclic aliphatic hydrocarbon(s) which can be used as an organic reaction medium can comprise, or consist essentially of cyclohexane, methyl cyclohexane, or any combination thereof.

Non-limiting examples of suitable aromatic hydrocarbon (s) which can be used as an organic reaction medium can comprise, or can consist essentially of, a $C_6$ to $C_{10}$ aromatic hydrocarbon(s). In a non-limiting aspect, the aromatic hydrocarbon(s) which can be utilized as the organic reaction medium can comprise, or can consist essentially of benzene, toluene, xylene (including ortho-xylene, meta-xylene, para-xylene, or mixtures thereof), ethylbenzene, or combinations thereof.

Non-limiting examples of the halogenated aliphatic hydrocarbon(s) which can be used as the organic reaction medium can comprise, or can consist essentially of, a $C_1$ to $C_{15}$ halogenated aliphatic hydrocarbon(s), a $C_1$ to $C_{10}$ halogenated aliphatic hydrocarbon(s), or a $C_1$ to $C_5$ halogenated aliphatic hydrocarbon(s). The halogenated aliphatic hydrocarbon(s) which can be utilized as an organic reaction medium can be cyclic or acyclic and/or can be linear or branched, unless otherwise specified. In a non-limiting aspect, the halogenated aliphatic hydrocarbon(s) which can be utilized as an organic reaction medium can comprise, or can consist essentially of methylene chloride, chloroform, carbon tetrachloride, dichloroethane, trichloroethane, or combinations thereof.

Non-limiting examples of the halogenated aromatic hydrocarbon(s) which can be useful as the organic reaction medium can comprise, or can consist essentially of, a $C_6$ to $C_{20}$ halogenated aromatic hydrocarbon(s), or a $C_6$ to $C_{10}$ halogenated aromatic hydrocarbon(s). In a non-limiting aspect, the halogenated aromatic hydrocarbon(s) which can be used as the organic reaction medium can comprise, or can consist essentially of, chlorobenzene, dichlorobenzene, or any combination thereof.

The choice of organic reaction medium can be made on the basis of convenience in processing. For example, isobutane can be chosen to be compatible with solvents and diluents used in processes using the product(s) of the processes described herein (e.g., using the product for the formation of polymer in a subsequent processing step). In some aspects, the organic reaction medium can be chosen to be easily separable from the one or more oligomers in the oligomer product. In some aspects, an oligomer of the oligomer product can be utilized as the reaction system solvent.

In an aspect, the oligomer product can be formed in a reaction zone. In an embodiment, the reaction zone of any process described herein can comprise a continuous stirred tank reactor, a plug flow reactor, or any combination thereof; alternatively, a continuous stirred tank reactor; or alternatively, a plug flow reactor. In some embodiments, the reaction zone of any process described herein can comprise a continuous stirred tank reactor, a loop reactor, a solution reactor, a tubular reactor, a recycle reactor, a bubble reactor, or any combination thereof; alternatively, a continuous stirred tank reactor; alternatively, a loop reactor; alternatively, a solution reactor; alternatively, a tubular reactor; alternatively, a recycle reactor; or alternatively, a bubble reactor. In other embodiments, the reaction zone in which the oligomer product can be formed can comprise multiple reactors; or alternatively, only one reactor. When multiple reactors are present, each of the reactors can be the same or can be different types of reactors. Additionally, when the reaction zone can comprise more than one reactor, each reactor independently can be any reactor described herein, and the reactors can be arranged in series, parallel, or any combination thereof; alternatively, in series; or alternatively, in parallel.

It should be noted that when the reaction zone can comprise multiple reactors, each reactor can be operated independent of each other (regardless of whether they are operated in series or parallel). As such, the contact modes (if needed), the conditions under which the oligomer product can be formed, the oligomer product formation parameters under which the oligomer product can be formed, and/or the reaction zone conditions can be different for each reactor. In particular, when the reaction zone comprises multiple reactors in series, each reactor can be operated to achieve different goals. For example, a first reactor can be operated to i) contact ethylene, the metal salt and the heteroatomic ligand (or alternatively, ethylene, the first metal salt, and the heteroatomic ligand complexed to the first metal salt), the optional organic reaction medium and the optional hydrogen and ii) initiate production of the oligomer product under a first set of conditions capable of producing the oligomer product to some intermediate ethylene conversion and the effluent of the first reactor transferred to a second reactor operated to achieve the desired ethylene conversion under a second set of conditions capable of producing the oligomer product with or without additional ethylene, the metal salt, the heteroatomic ligand (or alternatively, ethylene, the first metal salt, and the heteroatomic ligand complexed to the first metal salt), the optional organic reaction medium and the optional hydrogen being added to the reactor/reaction zone.

In any aspect and/or embodiment, the oligomer product can be formed at, the reaction zone can have, or the reaction zone can operate at, conditions that can comprise, either singly or in any combination, a heteroatomic ligand molar equivalent concentration, a heteroatomic ligand first metal salt complex molar equivalent concentration, an equivalent molar ratio of second metal salt to heteroatomic ligand of the heteroatomic ligand metal salt complex, an equivalent molar ratio of second metal salt to heteroatomic ligand metal salt complex, an equivalent molar ratio of metal salt to heteroatomic ligand, an aluminum of the organoaluminum compound to heteroatomic ligand molar equivalent ratio, an aluminum of the organoaluminum compound to heteroatomic ligand first metal salt complex molar equivalent ratio, an aluminum of the organoaluminum compound concentration, an ethylene partial pressure, an ethylene to organic reaction medium mass ratio, a temperature (or an average temperature), an Schulz-Flory K value, a hydrogen partial pressure, and/or a hydrogen to ethylene mass ratio. In any aspect and/or embodiment, the oligomer product can be formed at, the reaction zone can have, or the reaction zone can operate at, conditions that can comprise, a heteroatomic ligand molar equivalent concentration; alternatively, a heteroatomic ligand first metal salt complex molar equivalent concentration; alternatively, an equivalent molar ratio of second metal salt to heteroatomic ligand of the heteroatomic ligand metal salt complex; alternatively, an equivalent molar ratio of second metal salt to heteroatomic ligand metal salt complex; alternatively, an equivalent molar ratio of metal salt to heteroatomic ligand; alternatively, an aluminum of the organoaluminum compound to heteroatomic ligand molar equivalent ratio; alternatively, an aluminum of the organoaluminum compound to heteroatomic ligand first metal salt complex molar equivalent ratio; alternatively, an aluminum of the organoaluminum compound concentration; alternatively, an ethylene partial pressure; alternatively, an ethylene to organic reaction medium mass ratio; alternatively, a temperature (or an average temperature); alternatively, an Schulz-Flory K value; alternatively, a hydrogen partial pressure; or alternatively, a hydrogen to ethylene mass ratio.

In any aspect and/or embodiment, the oligomer product can be formed at, the reaction zone can have, or the reaction zone can operate at, a particular heteroatomic ligand molar equivalent concentration (or alternatively, heteroatomic ligand metal salt complex molar equivalent concentration). In an embodiment, the oligomer product can be formed at, the reaction zone can have, or the reaction zone can operate at, a minimum heteroatomic ligand molar equivalent concentration (or alternatively, heteroatomic ligand metal salt complex molar equivalent concentration) of $1 \times 10^{-6}$, $1 \times 10^{-5}$, or $1 \times 10^{-4}$ heteroatomic ligand molar equivalents/kg (or alternatively, heteroatomic ligand metal salt complex molar equivalents/kg) based upon the kg mass of the reaction solution; alternatively or additionally, at a maximum heteroatomic ligand molar equivalent concentration (or alternatively, heteroatomic ligand metal salt complex molar equivalent concentration) of $1 \times 10^{-1}$, $1 \times 10^2$, or $1 \times 10^{-3}$ heteroatomic ligand molar equivalents/kg (or alternatively, heteroatomic ligand metal salt complex molar equivalents/kg) based upon the kg mass of the reaction solution. In an aspect, the oligomer product can be formed at, the reaction zone can have, or the reaction zone can operate at, a heteroatomic ligand molar equivalent concentration (or alternatively, heteroatomic ligand metal salt complex molar equivalent concentration) in the range of any minimum heteroatomic ligand molar equivalent concentration (or alternatively, heteroatomic ligand metal salt complex molar equivalent concentration) disclosed herein to any maximum heteroatomic ligand molar equivalent concentration (or alternatively, heteroatomic ligand metal salt complex molar equivalent concentration) disclosed herein. In a non-limiting embodiment, the oligomer product can be formed, the reaction zone can have, or the reaction zone can operate, at an heteroatomic ligand molar equivalent concentration (or alternatively, heteroatomic ligand metal salt complex molar equivalent concentration) in the range of $1 \times 10^{-6}$ to $1 \times 10^{-1}$, $1 \times 10^{-5}$ to $1 \times 10^2$, or $1 \times 10^{-4}$ to $1 \times 10^{-3}$ heteroatomic ligand molar equivalents/kg (or alternatively, heteroatomic ligand metal salt complex molar equivalents/kg) based upon the kg mass of the reaction solution. Other heteroatomic ligand molar equivalent concentration (or alternatively, heteroatomic ligand metal salt complex molar equivalent concentration) ranges that can be utilized are readily apparent to those skilled in the art with the aid of this disclosure.

In any aspect and/or embodiment utilizing a second metal salt and a heteroatomic ligand first metal salt complex, the oligomer product can be formed at, the reaction zone can have, or the reaction zone can operate at, a particular equivalent molar ratio of the second metal salt to the heteroatomic ligand of the heteroatomic ligand metal salt complex (or a particular equivalent molar ratio of the second metal salt to the heteroatomic ligand first metal salt complex). In an embodiment, the oligomer product can be formed at, the reaction zone can have, or the reaction zone can operate at, a minimum equivalent molar ratio of the second metal salt to the heteroatomic ligand of the heteroatomic ligand first metal salt complex (or a minimum equivalent molar ratio of the second metal salt to the heteroatomic ligand first metal salt complex) of 0.1:1, 0.25:1, 0.5:1, 1.2:1, 2:1, or 3:1; alternatively or additionally, a maximum equivalent molar ratio of the second metal salt to the heteroatomic ligand of the heteroatomic ligand first metal salt complex (or a maximum equivalent molar ratio of the second metal salt to the heteroatomic ligand first metal salt complex) of 100:1, 50:1, 25:1, 17:1 or 10:1. In an embodiment, the oligomer product can be formed at, the reaction zone can have, or the reaction zone can operate at, an equivalent molar ratio of the second metal salt to heteroatomic ligand of the heteroatomic ligand first metal salt complex (or an equivalent molar ratio of the second metal salt to the heteroatomic ligand first metal salt complex) in the range of any minimum equivalent molar ratio of the second metal salt to the heteroatomic ligand of the heteroatomic ligand first metal salt complex (or a minimum equivalent molar ratio of the second metal salt to the heteroatomic ligand first metal salt complex) disclosed herein to any maximum equivalent molar ratio of the second metal salt to the heteroatomic ligand of the heteroatomic ligand first metal salt complex (or maximum equivalent molar ratio of the second metal salt to the heteroatomic ligand first metal salt complex) disclosed herein. In a non-limiting embodiment, the equivalent molar ratio of the second metal salt to heteroatomic ligand of the heteroatomic ligand first salt complex (or equivalent molar ratio of the second metal salt to the heteroatomic ligand first metal salt complex) can be in the range of from 0.1:1 to 100:1, from 0.25:1 to 50:1, from 0.5:1 to 50:1, from 1.2:1 to 50:1, from 1.2:1 to 25:1; from 2:1 to 17:1, or from 3:1 to 10:1. Other ranges of the equivalent molar ratio of second metal salt to heteroatomic ligand of the heteroatomic ligand first metal salt complex iron salt (or equivalent molar ratio of the second metal salt to the heteroatomic ligand first metal salt complex) that can be utilized will be readily apparent to those skilled in the art with the aid of this disclosure.

In any aspect and/or embodiment utilizing a metal salt and a heteroatomic ligand, the oligomer product can be formed at, the reaction zone can have, or the reaction zone can operate at, a particular equivalent molar ratio of the metal salt to heteroatomic ligand. In an embodiment, the oligomer product can be formed at, the reaction zone can have, or the reaction zone can operate at, a minimum equivalent molar ratio of the metal salt to heteroatomic ligand of 1.25:1, 1.5:1, 2:1, 2.5:1 or 3:1; alternatively or additionally, a maximum equivalent molar ratio of iron salt to heteroatomic ligand of 100:1, 75:1 50:1, 40:1, 30:1, 25:1, 20:1, 15:1, or 10:1. In an embodiment, the oligomer product can be formed at, the reaction zone can have, or the reaction zone can operate at, an equivalent molar ratio of the metal salt to heteroatomic ligand in the range of any minimum equivalent molar ratio of the metal salt to heteroatomic ligand disclosed herein to any maximum equivalent molar ratio of the metal salt to heteroatomic ligand disclosed herein. In a non-limiting embodiment, the equivalent molar ratio of the metal salt to heteroatomic ligand can be in the range of from 1.25 to 100:1, from 1.5 to 75:1, from 1.5 to 50:1, from 1.5:1 to 40:1; from 2:1 to 40:1, from 2.5:1 to 40:1, from 3:1 to 30:1, from 3:1 to 25:1, from 3:1 to 20:1, from 3:1 to 15:1, or from 3:1 to 10:1. Other ranges of the equivalent molar ratio of the metal salt to heteroatomic ligand that can be utilized will be readily apparent to those skilled in the art with the aid of this disclosure.

In any aspect and/or embodiment, the oligomer product can be formed at, the reaction zone can have, or the reaction zone can operate at a particular aluminum of the organoaluminum compound to heteroatomic ligand molar equivalent ratio (or alternatively, aluminum of the organoaluminum compound to heteroatomic ligand first metal salt complex molar equivalent ratio). In an embodiment, the oligomer product can be formed at, the reaction zone can have, or the reaction zone can operate at, a minimum aluminum of the organoaluminum compound to heteroatomic ligand molar equivalent ratio (or alternatively, aluminum of the organoaluminum compound to heteroatomic ligand first metal salt complex molar equivalent ratio), of 100:1, 200:1, 300:1, or 400:1; alternatively or additionally, a maximum aluminum of the organoaluminum compound to heteroatomic ligand molar equivalent ratio (or alternatively, aluminum of the organoaluminum compound to heteroatomic ligand first metal salt complex molar equivalent ratio), of 5,000:1, 2,000:1, 1,500:1, or 1,000:1. In an embodiment, the oligomer product can be formed at, the reaction zone can have, or the reaction zone can operate at, an aluminum of the organoaluminum compound to heteroatomic ligand molar equivalent ratio (or alternatively, aluminum of the organoaluminum compound to heteroatomic ligand first metal salt complex molar equivalent ratio), in the range of any minimum aluminum of the organoaluminum compound to heteroatomic ligand molar equivalent ratio (or alternatively, aluminum of the organoaluminum compound to heteroatomic ligand first metal salt complex molar equivalent ratio), disclosed herein to any maximum aluminum of the organoaluminum compound to heteroatomic ligand molar equivalent ratio (or alternatively, aluminum of the organoaluminum compound to heteroatomic ligand first metal salt complex molar equivalent ratio), disclosed herein. In a non-limiting embodiment, the oligomer product can be formed at, the reaction zone can have, or the reaction zone can operate at, an aluminum of the organoaluminum compound to heteroatomic ligand molar equivalent ratio (or alternatively, aluminum of the organoaluminum compound to heteroatomic ligand first metal salt complex molar equivalent ratio), in the range of 100:1 to 5,000:1, 200:1 to 2,000:1, 300:1 to 1,500:1, or 400:1 to 1,000:1. Other aluminum of the organoaluminum compound to heteroatomic ligand molar equivalent ratio (or alternatively, aluminum of the organoaluminum compound to heteroatomic ligand first metal salt complex molar equivalent ratio), ranges that can be utilized are readily apparent to those skilled in the art with the aid of this disclosure.

In any aspect and/or embodiment, the oligomer product can be formed at, the reaction zone can have, or the reaction zone can operate at, a particular aluminum of the organoaluminum compound concentration, also referred to as aluminum concentration or Al concentration. In an embodiment, the oligomer product can be formed at, the reaction zone can have, or the reaction zone can operate at, a minimum Al concentration of 0.3 mmol Al/kg, 0.75 mmol Al/kg, 0.9 mmol Al/kg, or 1.1 mmol Al/kg based upon the kg mass of the reaction solution; alternatively or additionally, a maximum Al concentration of 15 mmol Al/kg, 12.5 mmol Al/kg, 10 mmol Al/kg, 7.5 mmol Al/kg, 5 mmol Al/kg, 2.6 mmol Al/kg, 2.2 mmol Al/kg, 1.8 mmol Al/kg, or 1.5 mmol Al/kg based upon the kg mass of the reaction solution. In an embodiment, the oligomer product can be formed at, the reaction zone can have, or the reaction zone can operate at, an Al concentration in the range of any minimum Al concentration disclosed herein to any maximum Al concentration disclosed herein. In a non-limiting embodiment, the oligomer product can be formed at, the reaction zone can have, or the reaction zone can operate at, an Al concentration in the range of 0.3 mmol Al/kg to 15 mmol Al/kg, 0.3 mmol Al/kg to 10 mmol Al/kg, 0.5 mmol Al/kg to 10 mmol Al/kg, 0.5 mmol Al/kg to 7.5 mmol Al/kg, 0.5 mmol Al/kg to 5 mmol Al/kg, 0.75 mmol Al/kg to 2.6 mmol Al/kg, 0.75 mmol Al/kg to 2.2 mmol Al/kg, 0.9 mmol Al/kg to 1.8 mmol Al/kg, 1.1 mmol Al/kg to 1.8 mmol Al/kg, or 1.1 mmol Al/kg to 1.5 mmol Al/kg based upon the kg mass of the reaction solution. Other Al concentration ranges that can be utilized are readily apparent to those skilled in the art with the aid of this disclosure.

In any aspect and/or embodiment, the oligomer product can be formed at, the reaction zone can have, or the reaction zone can operate at, a minimum ethylene partial pressure of 50 psi (344 KPa), 100 psi (689 KPa), 250 psi (1.72 MPa), 500 psi (3.45 MPa), or 800 psi (5.52 MPa); alternatively or additionally, a maximum ethylene partial pressure of 5,000 psi (34.5 MPa), 3,000 psi (20.9 MPa), 2,000 psi (13.8 MPa), 1,500 psi (10.3 MPa), or 1000 psi (6.89 MPa). In an embodiment, the oligomer product can be formed at, the reaction zone can have, or the reaction zone can operate at, an ethylene partial pressure in the range of any minimum ethylene partial pressure disclosed herein to any maximum ethylene partial pressure disclosed herein. In some non-limiting embodiments, the oligomer product can be formed at, the reaction zone can have, or the reaction zone can operate at, an ethylene partial pressure in the range of 50 psi (344 KPa) to 5,000 psi (34.5 MPa), 100 psi (689 KPa) to 3,000 psi (20.9 MPa), 250 psi (1.72 MPa) to 2,000 psi (13.8 MPa), 500 psi (3.45 MPa) to 2,000 psi (13.8 MPa), 500 psi (3.45 MPa) to 1,500 psi (10.3 MPa), or 800 psi (5.52 kPa) to 1000 psi (6.89 MPa). Other ethylene partial pressure ranges are readily apparent to those skilled in the art with the aid of this disclosure.

In any aspect and/or embodiment wherein an organic reaction medium is utilized, the oligomer product can be formed at, the reaction zone can have, or the reaction zone can operate at, a minimum ethylene:organic reaction medium mass ratio of 0.8:1, 1:1, 1.25:1, or 1.5:1; alternatively, or additionally, a maximum ethylene:organic reaction medium mass ratio of 4.5:1, 4:1, 3.5:1, 3:1, or 2.5:1. In an embodiment wherein an organic reaction medium is utilized, the oligomer product can be formed at, the reaction zone can have, or the reaction zone can operate at, an ethylene:organic reaction medium mass ratio in the range of any minimum ethylene:organic reaction medium mass ratio disclosed herein to any maximum ethylene:organic reaction medium mass ratio disclosed herein. In some non-limiting embodiments wherein an organic reaction medium is utilized, the oligomer product can be formed at, the reaction zone can have, or the reaction zone can operate at, an ethylene:organic reaction medium mass ratio in the range of 0.8:1 to 4.5:1, 1:1 to 4:1, 1:1 to 3.5:1, 1.25:1 to 3:1, or 1.5:1 to 2.5:1. Other ethylene:organic reaction medium mass ratio ranges that can be utilized are readily apparent to those skilled in the art with the aid of this disclosure.

In any aspect and/or embodiment, the oligomer product can be formed at, the reaction zone can have, or the reaction zone can operate at, a minimum reaction zone temperature of 0° C., 25° C., 40° C., 50° C., or 60° C.; alternatively or additionally, a maximum reaction zone reaction zone temperature of 200° C., 150° C., 125° C., 110° C., or 100° C. In an embodiment, the oligomer product can be formed at, the reaction zone can have, or the reaction zone can operate at, a reaction zone temperature in the range of any minimum temperature disclosed herein to any maximum temperature disclosed herein. In a non-limiting embodiment, the oligomer product can be formed at, the reaction zone can have, or the reaction zone can operate at, a reaction zone temperature in the range of 0° C. to 200° C., 25° C. to 150° C., 40° C. to 125° C., 50° C. to 125° C., 50° C. to 110° C., or 60° C. to 100° C. Other temperature ranges that can be utilized are readily apparent to those skilled in the art with the aid of this disclosure. In embodiments where the temperature can vary within the reaction zone, the temperatures provided herein accordingly can be average minimum reaction zone temperatures, average maximum reaction zone temperatures, or average reaction zone temperature.

In any aspect and/or aspect embodiment, the oligomer product can have a minimum Schulz-Flory K value of 0.4, 0.45, 0.5 or, 0.55; alternatively or additionally, a maximum Schulz-Flory K value of 0.9, 0.85, 0.8, 0.75, 0.7 or, 0.65. In an embodiment, the oligomer product can have a Schulz-Flory K value in the range of any minimum Schulz-Flory K value disclosed herein to any maximum Schulz-Flory K value disclosed herein. For example, in some non-limiting embodiments, the oligomer product can have a Schulz-Flory K value in the range from 0.4 to 0.9; alternatively, from 0.4 to 0.8; alternatively, from 0.5 to 0.8; alternatively, from 0.5 to 0.7; alternatively, from 0.55 to 0.7. Other oligomer product Schulz-Flory K value ranges are readily apparent to those of ordinary skill in the art from the present disclosure.

In any aspect and/or embodiment, the Schulz-Flory K value can be determined using any one or more of the $C_8$, $C_{10}$, $C_{12}$, $C_{14}$, or $C_{16}$ oligomer product. In an embodiment, the Schulz-Flory K value can be an average of any two or more Schulz-Flory K values using different adjacent pairs of produced oligomers described herein. In some embodiments, the Schulz-Flory K value can be an average of any two Schulz-Flory K values described herein; alternatively, any three Schulz-Flory K values described herein; or alternatively, any four Schulz-Flory K values described herein. For example, the Schulz-Flory K value can be determined using the $C_8$ and $C_{10}$ oligomer product; alternatively, the $C_{10}$ and $C_{12}$ oligomer product; alternatively, the $C_{12}$ and $C_{14}$ oligomer product; alternatively, the $C_{14}$ and $C_{16}$ oligomer product; alternatively, the $C_8$, $C_{10}$, and $C_{12}$ oligomer product, or alternatively, the $C_{10}$, $C_{12}$, and $C_{14}$ oligomer product, among other combinations of oligomer product.

In any aspect and/or embodiment wherein hydrogen is utilized, the oligomer product can be formed at, the reaction zone can have, or the reaction zone can operate at, a minimum hydrogen partial pressure of 1 psi (6.9 kPa), 2 psi (14 kPa); 5 psi (34 kPa), 10 psi (69 kPa), 15 psi (103 kPa), 20 psi (138 kPa), 30 psi (206 kPa); alternatively or additionally, a maximum hydrogen partial pressure of 150 psi (1.03 MPa), 100 psi (689 kPa), 75 psi (517 kPa), or 50 psi (345 kPa). In an embodiment, the oligomer product can be formed at, the reaction zone can have, or the reaction zone can operate at, a hydrogen partial pressure in the range of any minimum hydrogen partial pressure disclosed herein to any maximum hydrogen partial pressure disclosed herein. In some non-limiting embodiments wherein hydrogen is utilized, the oligomer product can be formed at, the reaction zone can have, or the reaction zone can operate at, a hydrogen partial pressure in the range of 1 psi (6.9 kPa) to 150 psi (1.4 MPa), from 5 psi (34 kPa) to 100 psi (689 kPa), from 10 psi (69 kPa) to 100 psi (689 kPa), or from 15 psi (100 kPa) to 75 psi (517 kPa). Other hydrogen partial pressure ranges that can be utilized are readily apparent to those of ordinary skill in the art with the aid of this disclosure.

In any aspect and/or embodiment wherein hydrogen is utilized, the oligomer product can be formed at, the reaction zone can have, or the reaction zone can operate at, a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed at, the reaction zone can have, or the reaction zone can operate at, a hydrogen to ethylene mass ratio in the range of any minimum hydrogen to ethylene mass ratio disclosed herein to any maximum hydrogen to ethylene mass ratio disclosed herein. In some non-limiting embodiments, the oligomer product can be formed at, the reaction zone can have, or the reaction zone can operate at, a hydrogen to ethylene mass ratio in the range of (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those of ordinary skill in the art with the aid of this disclosure.

Without being limited to theory, it is believed that the presence of the second metal salt in processes utilizing a heteroatomic ligand first metal salt complex can increase the stability of and/or can increase the lifetime of the active catalytic species produced by contacting the heteroatomic ligand first metal salt with the organoaluminum compound. In a particular aspect of the present disclosure, processes utilizing any second metal salt to the heteroatomic ligand of the heteroatomic ligand metal salt complex (or second metal salt to the heteroatomic ligand metal salt complex) can have a $C_4$-$C_{20}$ productivity at least 5%, 10% 13%, 15%, or 17% greater than the $C_4$-$C_{20}$ productivity of an otherwise similar process wherein an equivalent molar ratio of the second metal salt to the heteroatomic ligand of the heteroatomic ligand metal salt complex (or second metal salt to the heteroatomic ligand metal salt complex) is less than 0.1:1. In a non-limiting aspect, the $C_4$-$C_{20}$ productivity for processes utilizing a second metal salt and a heteroatomic ligand first metal salt complex (or second metal salt to the heteroatomic ligand metal salt complex) can be less than or equal to 100%, 75%, 50%, or 40% the $C_4$-$C_{20}$ productivity of an otherwise similar process wherein an equivalent molar ratio of the second metal salt to the heteroatomic ligand of the heteroatomic ligand metal salt complex (or second metal salt to the heteroatomic ligand metal salt complex) is less than 0.1:1. In some non-limiting embodiments, the $C_4$-$C_{20}$ productivity increase can range from any minimum $C_4$-$C_{20}$ productivity increase disclosed herein to any maximum $C_4$-$C_{20}$ productivity increase disclosed herein. In a non-limiting embodiment, the $C_4$-$C_{20}$ productivity can be in the range of 5% to 100%, 10% to 100%, 10% to 75%, 13% to 50%, 13% to 50%, 15% to 40%, or 17% to 40% greater than the $C_4$-$C_{20}$ productivity of an otherwise similar process wherein an equivalent molar ratio of the second metal salt to the heteroatomic ligand of the heteroatomic ligand metal salt complex (or second metal salt to the heteroatomic ligand metal salt complex) is less than 0.1:1. Other $C_4$-$C_{20}$ productivity increase ranges are readily apparent to those skilled in the art with the aid of this disclosure. Equivalent molar ratios of the second metal salt to the heteroatomic ligand of the heteroatomic ligand metal salt complex (or second metal salt to the heteroatomic ligand metal salt complex) for the processes described herein are independently described herein and these independently described equivalent molar ratio of the second metal salt to the heteroatomic ligand of the heteroatomic ligand metal salt complex (or second metal salt to the heteroatomic ligand metal salt complex) can be utilized without limitation to further describe the $C_4$-$C_{20}$ productivity increases when compared to an otherwise similar process wherein an equivalent molar ratio of the second metal salt to the heteroatomic ligand of the heteroatomic ligand metal salt complex (or second metal salt to the heteroatomic ligand metal salt complex) is less than 0.1:1.

Without being limited to theory, it is believed that in processes utilizing a metal salt and a heteroatomic ligand, an equivalent molar ratio of metal salt to heteroatomic greater than the 1:1 ratio to produce the heteroatomic ligand metal salt complex can increase the stability of and/or can increase the lifetime of the active catalytic species produced by contacting the metal salt, heteroatomic ligand, and organoaluminum compound. In a particular aspect of the present disclosure, processes utilizing a equivalent molar ratio of metal salt to heteroatomic ligand greater than the 1:1 equivalent molar ratio needed to produce the heteroatomic ligand metal salt complex (any equivalent molar ratio of metal salt to heteroatomic disclosed herein) can have a $C_4$-$C_{20}$ productivity at least 100%, 200% 300%, 400%, or 500% greater than the $C_4$-$C_{20}$ productivity of an otherwise similar process wherein an equivalent molar ratio of the metal salt to the heteroatomic ligand is less than 1.1:1. In a non-limiting aspect, the $C_4$-$C_{20}$ productivity for processes utilizing a metal salt and a heteroatomic ligand can be less than or equal to 10,000%, 5,000%, 3,000%, or 1,000% the $C_4$-$C_{20}$ productivity of an otherwise similar process wherein an equivalent molar ratio of the metal salt to the heteroatomic ligand is less than 1.1:1. In some non-limiting embodiments, the $C_4$-$C_{20}$ productivity increase can range from any minimum $C_4$-$C_{20}$ productivity increase disclosed herein to any maximum $C_4$-$C_{20}$ productivity increase disclosed herein. In a non-limiting embodiment, the $C_4$-$C_{20}$ productivity can be in the range of 100% to 10,000%, 200% to 5,000%, 300% to 3,000%, 400% to 3,000%, 500% to 3,000%, 300% to 1,000%, 400% to 1,000%, or 500% to 1,000% of the $C_4$-$C_{20}$ productivity of an otherwise similar process wherein an equivalent molar ratio of the metal salt to the heteroatomic ligand is less than 1.1:1. Other $C_4$-$C_{20}$ productivity increase ranges are readily apparent to those skilled in the art with the aid of this disclosure. Equivalent molar ratios of metal salt to heteroatomic ligand for the processes described herein are independently described herein and these independently described equivalent molar ratio of metal salt to heteroatomic ligand can be utilized without limitation to further describe the $C_4$-$C_{20}$ productivity increases when compared to an otherwise similar process wherein an equivalent molar ratio of the metal salt to the heteroatomic ligand is less than 1.1:1.

In any aspect and/or embodiment, the processes described herein can produce an oligomer product with high selectivity to linear alpha olefins; or alternatively, to normal alpha olefins. In some embodiments, the processes described herein can produce a reactor effluent wherein the $C_6$ olefin oligomer product has a 1-hexene content of at least 98.5 wt. %; alternatively, at least 98.75 wt. %; alternatively, at least 99.0 wt. %; or alternatively, at least 99.25 wt. %. In other embodiments, the processes described herein can produce a reactor effluent wherein the $C_8$ olefin oligomer product has a 1-octene content of at least 98 wt. %; alternatively, at least 98.25 wt. %; alternatively, at least 98.5 wt. %; alternatively, at least 98.75 wt. %; or alternatively, at least 99.0 wt. %. In yet other embodiments, the processes described herein can produce a reactor effluent wherein the $C_{10}$ olefin oligomer product has a 1-decene content of at least 97.5 wt. %; alternatively, at least 97.75 wt. %; alternatively, at least 98 wt. %; alternatively, at least 98.25 wt. %; or alternatively, at least 98.5 wt. %. In yet other embodiments, the processes described herein can produce a reactor effluent wherein the $C_{12}$ olefin oligomer product has a 1-dodecene content of at least 96.5 wt. %; alternatively, at least 97 wt. %; alternatively, at least 97.5 wt. %; alternatively, at least 97.75 wt. %; or alternatively, at least 98.0 wt. %. In yet other embodiments, the processes described herein can produce a reactor effluent wherein the oligomer product can comprise any combination of any $C_6$ olefin oligomer product 1-hexene content described herein, any $C_8$ olefin oligomer product 1-octene content described herein, any $C_{10}$ olefin oligomer product 1-decene content described herein, and/or any $C_{12}$ olefin oligomer product 1-dodecene content described herein. In some non-limiting examples, the processes described herein can produce a reactor effluent having a $C_6$ olefin oligomer product 1-hexene content of at least 99 wt. % and a $C_{12}$ olefin oligomer product 1-dodecene content of at least 97.5 wt. %; alternatively, a $C_8$ olefin oligomer product 1-octene content of at least 98.5 wt. % and a $C_{12}$ olefin oligomer product 1-dodecene octene content of at least 97.5 wt. %; or alternatively, a $C_6$ olefin oligomer product 1-hexene content of at least 99 wt. %, a $C_8$ olefin oligomer product 1-octene content of at least 98.5 wt. %, a $C_{10}$ olefin oligomer product 1-decene content of at least 98 wt. %, and a $C_{12}$ olefin oligomer product 1-dodecene content of at least 97.5 wt. %. Other combinations of reactor effluent olefin oligomer 1-alkene contents are readily apparent from the present disclosure.

Various aspects and/or embodiments described herein can refer to substituted groups or compounds. In an embodiment, each substituent of any aspect and/or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl group or substituent of any aspect and/or embodiment calling for a substituent can be a $C_1$ to $C_{10}$, or a $C_1$ to $C_5$ hydrocarbyl group. In an embodiment, each hydrocarboxy group or substituent of any aspect and/or embodiment calling for a substituent can be a $C_1$ to $C_{10}$, or a $C_1$ to $C_5$ hydrocarboxy group. In an embodiment, any halide substituent of any aspect and/or embodiment calling for a halide substituent can be a fluoride, chloride, bromide, or iodide; alternatively, a fluoride or chloride. In some embodiments, any halide substituent of any aspect and/or embodiment calling for a substituent can be a fluoride; alternatively, a chloride; alternatively, a bromide; or alternatively, an iodide.

In an embodiment, any hydrocarbyl group or substituent of any aspect and/or embodiment calling for a substituent can be an alkyl group, an aryl group, or an aralkyl group; alternatively, an alkyl group; alternatively, an aryl group; or alternatively, an aralkyl group. In an embodiment, any alkyl group of any aspect and/or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl group of any aspect and/or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl group of any aspect and/or aspect calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any hydrocarboxy group or substituent of any aspect and/or embodiment calling for a substituent can be an alkoxy group, an aryloxy group, or an aralkoxy group; alternatively, an alkoxy group; alternatively, an aryloxy group; or alternatively, an aralkoxy group. In an embodiment, any alkoxy group of any aspect and/or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy group of any aspect and/or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an aspect, any aralkoxy group of any aspect or aspect calling for a substituent can be a benzoxy group.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the applicants are not entitled to antedate such disclosure by virtue of prior disclosure.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present disclosure or the scope of the appended claims.

The data and descriptions provided in the examples are given to show particular aspects and/or embodiments of the compounds, catalyst systems, and olefin oligomerization and/or olefin polymerization methods disclosed, and to demonstrate a number of the practices and advantages thereof. The examples are given as a more detailed demonstration of some of the aspects and/or embodiments described herein and are not intended to limit the disclosure or claims in any manner.

Additional Disclosure

The following enumerated embodiments of the present disclosures are provided as non-limiting examples.

Embodiment 1

A process for forming an oligomer product comprising: a) introducing into a reaction zone i. ethylene; ii. a heteroatomic ligand metal salt complex comprising a heteroatomic ligand complexed to a first metal salt where the first metal salt is an iron salt, a cobalt salt, or a combination thereof; iii. a second metal salt wherein an equivalent molar ratio of the second metal salt to the heteroatomic ligand of the heteroatomic ligand metal salt complex (or second metal salt to the heteroatomic ligand metal salt complex) is at least 0.5:1 (or any other equivalent molar ratio of the second metal salt to the heteroatomic ligand of the heteroatomic ligand metal salt complex, or second metal salt to the heteroatomic ligand metal salt complex, disclosed herein) and where the second metal salt is an iron salt, a cobalt salt, or any combination thereof; iv. an organoaluminum compound; v. optionally hydrogen; and vi. optionally an organic reaction medium; and b) forming an oligomer product in the reaction zone.

Embodiment 2

The process of embodiment 1, wherein the equivalent molar ratio of the second metal salt to the heteroatomic ligand of the heteroatomic ligand metal salt complex (or second metal salt to the heteroatomic ligand metal salt complex) ranges from 1.2:1 to 50:1 (or any other equivalent molar ratio of the second metal salt to the heteroatomic ligand of the heteroatomic ligand metal salt complex, or second metal salt to the heteroatomic ligand metal salt complex, disclosed herein).

Embodiment 3

The process of embodiment 1 or 2, wherein a $C_4$-$C_{20}$ productivity is at least 10% greater than the $C_4$-$C_{20}$ productivity of an otherwise similar process wherein an equivalent molar ratio of the second metal salt to the heteroatomic ligand of the heteroatomic ligand metal salt complex (or second metal salt to the heteroatomic ligand metal salt complex) is less than 0.1:1.

Embodiment 4

The process of any one of embodiments 1 to 3, where the first metal salt comprises an iron halide, an iron β-diketonate, an iron carboxylate, or any combination thereof and the second metal salt comprises an iron halide, an iron β-diketonate, an iron carboxylate, or any combination thereof.

Embodiment 5

The process of any one of embodiments 1 to 4, where the first metal salt and the second metal salt are the same or different.

Embodiment 6

A process for forming an oligomer product comprising: a) introducing into a reaction zone i. ethylene; ii. a heteroatomic ligand; iii. a metal salt where 1) the metal salt is an iron salt, a cobalt salt, or any combination thereof, and 2) an equivalent molar ratio of the metal salt to the heteroatomic ligand is at least 1.5:1 (or any other equivalent molar ratio of the metal salt to the heteroatomic ligand disclosed herein); iv. an organoaluminum compound; v. optionally hydrogen; and vi. optionally an organic reaction medium; and b) forming an oligomer product in the reaction zone.

Embodiment 7

The process of embodiment 6, wherein the equivalent molar ratio of the metal salt to the heteroatomic ligand ranges from 1.5:1 to 50:1 (or any other equivalent molar ratio of the metal salt to the heteroatomic ligand disclosed herein).

Embodiment 8

The process of embodiment 6 or 7, wherein a $C_4$-$C_{20}$ productivity is at least 100% greater than the $C_4$-$C_{20}$ productivity of an otherwise same process wherein an equivalent molar ratio of the metal salt to the heteroatomic ligand is less than 1.1:1.

Embodiment 9

The process of any one of embodiments 6 to 8, where the metal salt comprises an iron halide, an iron β-diketonate, an iron carboxylate, or any combination thereof.

Embodiment 10

The process of any one of embodiments 1 to 9, wherein the heteroatomic ligand or the heteroatomic ligand of the heteroatomic ligand metal salt complex comprises 1) a bidentate metal salt complexing moiety, or 2) a tridentate metal salt complexing moiety, wherein the bidentate metal salt complexing moiety and the tridentate metal salt complexing moiety each independently comprise at least two metal salt complexing groups selected from the group consisting of an imine group and an aromatic nitrogen atom containing group.

Embodiment 11

The process of any one of embodiments 1 to 10, wherein the heteroatomic ligand or the heteroatomic ligand of the metal salt complex comprises an α-diimine, a pyridine bisimine, a phenanthroline imine, or any combination thereof.

Embodiment 12

The process of embodiment 11, wherein the heteroatomic ligand or the heteroatomic ligand of the metal salt complex is the α-diimine and the α-diimine comprises i) an α-diimine group, ii) a first imine group consisting of a hydrocarbyl group or substituted hydrocarbyl group attached to a first imine nitrogen atom of the α-diimine group, and iii) a second imine group comprising a first metal salt complexing group and a linking group linking the first metal salt complexing group to a second imine nitrogen atom of the α-diimine group.

Embodiment 13

The process of embodiment 11, wherein the α-diimine comprises i) an α-diimine group derived from an aromatic diacyl compound, ii) a first imine group consisting of an aryl group or substituted aryl group, and iii) a second imine group comprising a diarylphosphinyl first metal salt complexing group and a —$CH_2CH_2$— linking group linking the diarylphosphinyl first metal salt complexing group to the second imine nitrogen atom.

Embodiment 14

The process of embodiment 11, wherein the α-diimine comprises i) an α-diimine group derived from acenaphthenequinone, phenanthrenequinone, or pyrenequinone, ii) a first imine group consisting of an 2,6-dihydrocarbylphenyl group, and iii) a second imine group comprising a diphenylphosphinyl first metal salt complexing group or a di(substituted phenyl)phosphinyl first metal complexing group and a —$CH_2CH_2$— linking group linking the first metal salt complexing group to the second imine nitrogen atom.

Embodiment 15

The process of any one of embodiments 1 to 14 wherein the heteroatomic ligand metal salt complex has a structure selected from the group consisting of ADIFe I, ADIFe II, ADIFe III, ADIFe IV, ADIFe V, ADIFe VI, ADIFe VII, ADIFe VIII, ADIFe IX, ADIFe X, ADIFe XII, ADIFe XIII, and ADIFe XIV.

Embodiment 16

The process of embodiment 11, wherein the heteroatomic ligand or the heteroatomic ligand of the heteroatomic ligand metal salt complex is the pyridine bisimine and the pyridine bisimine comprises i) a 2,6-bis[(arylimine)hydrocarbyl]pyridine wherein the aryl groups can be the same or different, ii) a bis[(substituted arylimine)hydrocarbyl]pyridine wherein the substituted aryl groups can be the same or different, or iii) an [(arylimine)hydrocarbyl],[(substituted arylimine)hydrocarbyl]pyridine, or iii) an [(arylimine)hydrocarbyl],[(substituted arylimine)hydrocarbyl]-pyridine.

Embodiment 17

The process of embodiment 16, wherein the pyridine bisimine has 1) one, two, or three of the aryl groups and/or substituted aryl groups positions ortho to the carbon atom attached to the imine nitrogen independently are a halogen, a primary carbon atom group, or a secondary carbon atom group and the remainder of the aryl groups and/or substituted aryl groups positions ortho to the carbon atom attached to the imine nitrogen are hydrogen, 2) one of the aryl groups and/or substituted aryl groups positions ortho to the carbon atom attached to the imine nitrogen is a tertiary carbon atom group, none, one, or two of the aryl groups and/or substituted aryl groups positions ortho to the carbon atom attached to the imine nitrogen independently are a halogen, a primary carbon atom group or a secondary carbon atom group, and the remainder of the aryl groups and/or substituted aryl groups positions ortho to the carbon atom attached to the imine nitrogen are hydrogen, 3) two of the aryl groups and/or substituted aryl groups positions ortho to the carbon atom attached to the imine nitrogen independently are a tertiary carbon atom group, none, or one of the aryl groups and/or substituted aryl groups positions ortho to the carbon atom attached to the imine nitrogen independently are a halogen, a primary carbon atom group, or a secondary carbon atom group, and the remainder of the aryl groups and/or substituted aryl groups positions ortho to the carbon atom attached to the imine nitrogen are hydrogen, 4) one or two of the aryl groups and/or substituted aryl groups positions ortho to the carbon atom attached to the imine nitrogen independently are a tertiary carbon atom group(s) and the remainder of the aryl groups and/or substituted aryl groups positions ortho to the carbon atom attached to the imine nitrogen are hydrogen, 5) one or two of the aryl groups and/or substituted aryl groups positions ortho to the carbon atom attached to the imine nitrogen are a quaternary carbon atom group and the remainder of the aryl groups and/or substituted aryl groups positions ortho to the carbon atom attached to the imine nitrogen are hydrogen, or 6) all four of the substituted aryl groups positions ortho to the carbon atom attached to the imine nitrogen are fluorine.

Embodiment 18

The process of embodiment 16, wherein the pyridine bisimine is selected from the group consisting of 2,6-bis[(phenylimine) methyl]pyridine, 2,6-bis[(2-methylphenylimine)methyl]pyridine, 2,6-bis[(2-ethylphenylimine)methyl]pyridine, 2,6-bis[(2-isopropylphenylimine)methyl]pyridine, 2,6-bis[(2,4-dimethylphenylimine)methyl]pyridine, 2,6-bis[(2,6-diethylphenylimine)methyl]pyridine, 2-[(2,4,6-trimethylphenylimine)methyl]-6-[(4-methylphenylimine)-methyl]pyridine, 2-[(2,4,6-trimethylphenylimine)methyl]-6-[(3,5-dimethylphenylimine)methyl]pyridine, and 2-[(2,4,6-trimethylphenylimine)methyl]-6-[(4-t-butylphenylimine)methyl]pyridine.

Embodiment 19

The process of embodiment 11, wherein the heteroatomic ligand or the heteroatomic ligand of the heteroatomic ligand metal salt complex is the phenanthroline imine and the phenanthroline imine comprises a 2-(hydrocarbylimine)-1,10-phenanthroline, a 2-[(hydrocarbylimine)hydrocarbyl]-1,10-phenanthroline, a 2-(arylimine)-1,10-phenanthroline, a 2-[(arylimine)hydrocarbyl]-1,10-phenanthroline, a 2-(substituted arylimine)-1,10-phenanthroline, or a 2-[(substituted arylimine)hydrocarbyl]-1,10-phenanthroline.

Embodiment 20

The process of embodiment 19, wherein the phenanthroline imine comprises a 2-(2,6-dialkylphenylimine)-1,10-phenanthroline, a 2-[(2,6-dialkylphenylimine)alkyl]-1,10-phenanthroline, a 2-[(2,6-dialkylphenylimine)phenyl]-1,10-phenanthroline, a 2-(2,4,6-trialkylphenylimine)-1,10-phenanthroline, a 2-[(2,4,6-trialkylphenylimine)alkyl]-1,10-phenanthroline, a 2-[(2,4,6-trialkylphenylimine)phenyl]-1,10-phenanthroline, a 2-(2,6-dihalophenylimine)-1,10-phenanthroline, a 2-[(2,6-dihalophenylimine)alkyl]-1,10-phenanthroline, and a 2-[(2,6-dihalophenylimine)phenyl]-1,10-phenanthroline, or any combination thereof.

Embodiment 21

The process of embodiment 19, wherein phenanthroline imine is selected from the group consisting of 2-(2,6-difluorophenylimine)-1,10-phenanthroline, 2-(2,6-dichlorophenylimine)-1,10-phenanthroline, 2-(2,6-dibromophenylimine)-1,10-phenanthroline, 2-(2,6-dimethylphenylimine)-1,10-phenanthroline, 2-(2,6-diethylphenylimine)-1,10-phenanthroline, 2-(2,6-diisopropylphenylimine)-1,10-phenanthroline, 2-[(2,6-difluorophenylimine)methyl]-1,10-phenanthroline, 2-[(2,6-dichlorophenylimine)methyl]-1,10-phenanthroline, 2-[(2,6-dibromophenylimine)methyl]-1,10-phenanthroline, 2-[(2,6-dimethylphenylimine)methyl]-1,10-phenanthroline, 2-[(2,6-diethylphenyl-imine)methyl]-1,10-phenanthroline, 2-[(2,6-diisopropylphenylimine)methyl]-1,10-phenanthroline, 2-[(2,6-diethylphenylimine)ethyl]-1,10-phenanthroline, 2-[(2,6-diethylphenylimine)-n-propyl]-1,10-phenanthroline, 2-[(2,6-diethylphenylimine)iso-propyl]-1,10-phenanthroline, 2-[(2,4,6-tribromophenylimine)-methyl]-1,10-phenanthroline, 2-[(2,4,6-trimethylphenylimine)methyl]-1,10-phenanthroline, 2-[(2,6-dimethyl-4-bromophenylimine)methyl]-1,10-phenanthroline, 2-[(2,6-dibromo-4-methylphenylimine)-methyl]-1,10-phenanthroline, 2-[(2,6-dibromo-4-chlorophenylimine)methyl]-1,10-phenanthroline, 2-[(2,6-dimethylphenylimine)phenyl]-1,10-phenanthroline, 2-[(2,6-diethylphenylimine)phenyl]-1,10-phenanthroline, and 2-[(2,6-diisopropylphenylimine)phenyl]-1,10-phenanthroline.

Embodiment 22

The process of any one of embodiments 1 to 21, wherein the organoaluminum compound comprises an aluminoxane.

Embodiment 23

The process of embodiment 22, wherein the aluminoxane comprises methylaluminoxane, a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

Embodiment 24

The process of any one of embodiments 1 to 23, wherein the organo groups of the organoaluminum compound are substantially devoid of β,γ-branched organo groups and/or β,δ-branched organo groups.

Embodiment 25

The process of any one of embodiments 1 to 24, wherein the oligomer product is formed under conditions having (or the reaction zone has) an heteroatomic ligand molar equivalent concentration or heteroatomic ligand metal salt complex molar equivalent concentration of at least $1\times10^{-6}$ mmol/kg (or any other heteroatomic ligand molar equivalent concentration or heteroatomic ligand metal salt complex molar equivalent concentration disclosed herein).

Embodiment 26

The process of any one of embodiments 1 to 25, wherein the oligomer product is formed under conditions having (or the reaction zone has) an aluminum of the organo aluminum compound to heteroatomic ligand molar equivalent ratio or aluminum to heteroatomic ligand metal salt complex molar equivalent ratio of at least 100:1 (or any other aluminum to heteroatomic ligand molar equivalent ratio or aluminum to heteroatomic ligand metal salt complex molar equivalent ratio disclosed herein).

Embodiment 27

The process of any one of embodiments 1 to 26, wherein the oligomer product is formed under conditions having (or the reaction zone has) an aluminum of the organoaluminum compound concentration of at least 0.3 mmol Al/kg (or any other aluminum of the organoaluminum compound concentration disclosed herein).

Embodiment 28

The process of any one of embodiments 1 to 27, wherein the oligomer product is formed under conditions having (or the reaction zone has) an ethylene partial pressure of at least 100 psi (or any other ethylene partial pressure disclosed herein.

Embodiment 29

The process of any one of embodiments 1 to 28, wherein the oligomer product is formed under conditions having (or the reaction zone has) a temperature of at least 0° C. (or any other temperature disclosed herein).

Embodiment 30

The process of any one of embodiments 1 to 29, wherein the process utilizes a hydrogen and the oligomer product is formed under conditions having (or the reaction zone has) a hydrogen partial pressure of at least 5 psi (or any other hydrogen partial pressure disclosed herein).

Embodiment 31

The process of any one of embodiments 1 to 30, wherein the process utilizes a hydrogen and the oligomer product is formed under conditions having (or the reaction zone has) a hydrogen to ethylene mass ratio of at least (0.05 g hydrogen)/(kg ethylene) (or any other hydrogen to ethylene mass ratio disclosed herein).

Embodiment 32

The process of any one of embodiments 1 to 31, wherein the process utilizes an organic reaction medium and the organic reaction medium comprises, or consists essentially of, one or more aliphatic hydrocarbons.

Embodiment 33

The process of embodiments 32, wherein the organic reaction medium comprises, or consists essentially of, one or more $C_8$ to $C_{18}$ aliphatic hydrocarbons.

Embodiment 34

The process of embodiments 32, wherein the organic reaction medium comprises, or consists essentially of, one or more $C_8$ to $C_{16}$ saturated aliphatic hydrocarbons.

Embodiment 35

The process of embodiments 32, wherein the organic reaction medium comprises, or consists essentially of, one or more $C_8$ to $C_{16}$ olefinic aliphatic hydrocarbons.

Embodiment 36

The process of embodiments 32, wherein the organic reaction medium comprises, or consists essentially of, 1-decene, 1-dodecene, 1-tetradecene, or any combination thereof.

Embodiment 37

The process of any one of embodiments 32 to 36, wherein the organic reaction medium is substantially devoid of a halogenated compound.

Embodiment 38

The process of any one of embodiments 32 to 37, wherein the oligomer product is formed under conditions having (or the reaction zone has) an ethylene to organic reaction medium mass ratio of at least 0.8:1 (or any other ethylene to organic reaction medium mass ratio disclosed herein), Embodiment 39

The process of any one of embodiments 1 to 38, wherein the oligomer product has a Schultz-Flory K value in the range of 0.4 to 0.9 (or any other Schultz-Flory K value disclosed herein).

EXAMPLES

All operations were performed in an oxygen free and moisture free environment. Solvents were dried over 13× molecular sieves, and ethylene was purified using in-stream de-oxygenation and moisture removal beds. MMAO-3A was purchased from Akzo Nobel and utilized as received.

Heteroatomic metal salt complex ADIFe XIV was prepared using methods disclosed in US 2007/00221608 A1. Heteroatomic ligand PBI 1 was prepared using methods disclosed in US 2002/0016425 A1.

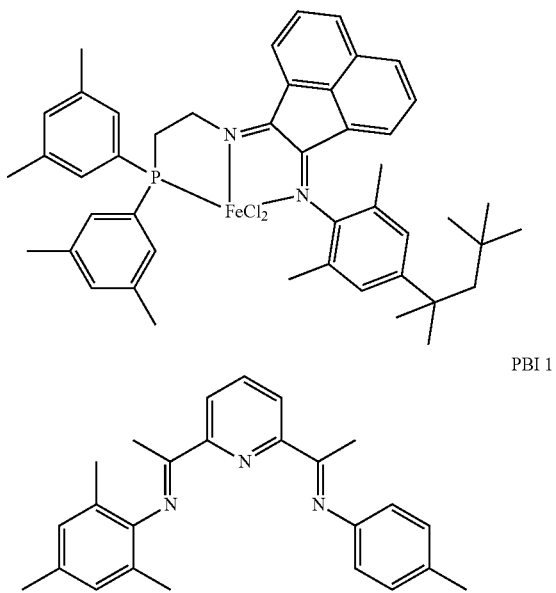

ADIFe XIV

PBI 1 of the autoclave reactor. After evacuating the reactor for several minutes, the entire contents of the glass charger were loaded into the autoclave reactor under vacuum. The autoclave reactor was then degassed with ethylene by carrying out several fill/vent cycles. The reactor was then pressurized with ethylene to 400 psig (2.8 MPa). Stirring was initiated resulting in breakage of the 5 mm NMR tube and activation of the catalyst. Ethylene was then fed to the autoclave reactor on demand to maintain a pressure of 400 psig (2.8 MPa) for the remainder of the reaction. The reaction temperature was maintained at a temperature of 50 to 60° C. by way of cooling water passed through internal cooling coils inside the autoclave reactor. After 15 min, the reactor was cooled to room temperature and vented to atmospheric pressure. The liquid products were analyzed by a gas chromatograph with a flame ionization detector (FID) detector against the n-nonane internal standard. Table 1 details the results of these ethylene oligomerization examples. Ethylene oligomerization examples 1 and 2 were run on the same day, while ethylene oligomerization examples 3 and 4 were run on a different day, and ethylene oligomerization examples 5 and 6 were run on yet a different day.

TABLE 1

| Example | mass of ADIFe, XIV, mg | Al:ADIFe XIV, Molar Ratio | Fe(acac)$_2$:ADIFe XIV Molar Ratio | Temp., °C | Productivity grams (C$_4$-C$_{20}$) | g (C$_4$-C$_{20}$)/ mmol ADIFe XIV | C$_{12}$/C$_{10}$ Schulz-Flory K value |
|---|---|---|---|---|---|---|---|
| 1 | 0.75 | 1000 | — | 50-60 | 15.45 | 17000 | 0.54 |
| 2 | 0.75 | 1000 | 10:1 | 50-60 | 19.09 | 21000 | 0.56 |
| 3 | 0.75 | 1000 | — | 50-60 | 15.66 | 17200 | 0.53 |
| 4 | 0.75 | 1000 | 10:1 | 50-60 | 16.74 | 18400 | 0.55 |
| 5 | 0.75 | 1000 | — | 50-60 | 18.02 | 19800 | 0.55 |
| 6 | 0.75 | 1000 | 10:1 | 50-60 | 23.76 | 26100 | 0.56 |

Examples 1-6

Ethylene oligomerization runs using no additional metal salt and additional metal salt, Fe(acac)$_2$, were run in pairs on the same day utilizing the same reactor to allow for comparison between the ethylene oligomerization runs performed on the same day. In a nitrogen-filled drybox, a stock toluene solution of 2.0 mg/mL (2.53×10$^{-3}$ meq/mL) of ADIFe XIV and a stock toluene solution of 4.0 mg/mL (1.57×10$^{-2}$ meq/mL) of Fe(acac)$_2$ were prepared. The appropriate amount of the ADIFe XIV and the Fe(acac)$_2$ stock solutions were added to a 5 mL NMR tube to provide the desired quantity of ADIFe XIV and of Fe(acac)$_2$ for the ethylene oligomerization. The NMR tube was then sealed. Also in the nitrogen-filled drybox, a glass charger was charged with 200 mL cyclohexane, approximately 1.0 g of n-nonane internal standard, and the appropriate amount of MMAO-7 (Akzo Nobel, 7.0 wt % Al) to achieve the desired α-diimine ligand to aluminum molar ratio for the ethylene oligomerization. The glass charger was then sealed. The NMR tube and charger were removed from the drybox. The NMR tube was secured to the stirrer shaft of a 1000 mL autoclave reactor with wire in a manner where the glass would shatter on starting the mixer. The autoclave reactor was then sealed and evacuated under high vacuum. The glass charger was then affixed to a charging port on the top The results of Examples 1-6 demonstrate that the addition of a metal salt to the ethylene oligomerization utilizing a heteroatomic ligand metal salt complex increases the productivity of ethylene oligomerization.

Examples 7-10

In a nitrogen-filled drybox, a stock cyclohexane solution of 0.14 mg/mL (3.68×10$^{-4}$ meq/mL) of PBI 1 and a stock cyclohexane solution of 1.0 mg/mL (3.94×10$^{-3}$ meq/mL) of Fe(acac)$_2$ were prepared. The appropriate amount of the PBI 1 and of the Fe(acac)$_2$ stock solutions were added to a 5 mL NMR tube to provide the desired quantity of PBI 1 and of Fe(acac)$_2$ for the ethylene oligomerization. The NMR tube was then sealed. Also in the nitrogen-filled drybox, a glass charger was charged with 200 mL cyclohexane, approximately 1.0 g of n-nonane internal standard, and the appropriate amount of MMAO-3A (Akzo Nobel, 7.0 wt % Al) to achieve the desired PBI 1 to aluminum molar ratio for the ethylene oligomerization. The glass charger was then sealed. The NMR tube and charger were removed from the drybox. The NMR tube was secured to the stirrer shaft of a 1000 mL autoclave reactor with wire in a manner where the glass would shatter on starting the mixer. The autoclave reactor was then sealed and evacuated under high vacuum. The glass charger was then affixed to a charging port on the top of the autoclave reactor. After evacuating the reactor for several minutes, the entire contents of the glass charger were loaded into the autoclave reactor under vacuum. The autoclave reactor was then degassed with ethylene by carrying out several fill/vent cycles. The reactor was then pressurized with ethylene to 400 psig (2.8 mPa). Stirring was initiated resulting in breakage of the 5 mm NMR tube and activation of the catalyst. Ethylene was then fed to the autoclave reactor on demand to maintain a pressure of 400 psig (2.8 mPa) for the remainder of the reaction. The reaction temperature was maintained at a temperature of 60 to 70° C. by way of cooling water passed through internal cooling coils inside the autoclave reactor. After 15 min, the reactor was cooled to room temperature and vented to atmospheric pressure. The liquid products were analyzed by a gas chromatograph with a flame ionization detector (FID) detector against the n-nonane internal standard. Table 2 details the results of these ethylene oligomerization examples.

initiated resulting in breakage of the 5 mm NMR tube and activation of the catalyst. Ethylene is then fed to the autoclave reactor on demand to maintain a pressure of 400 psig (2.8 MPa) for the remainder of the reaction. The reaction temperature is maintained at a temperature of 60 to 70° C. by way of cooling water passed through internal cooling coils inside the autoclave reactor. After 15 min, the reactor is cooled to room temperature and vented to atmospheric pressure. The liquid products are analyzed by a gas chromatograph with a flame ionization detector (FID) detector against the n-nonane internal standard. One ethylene oligomerization (Example 11) is performed in the absence of added $Fe(acac)_2$ and a second ethylene oligomerization (Example 12) is performed using a 10:1 molar ratio of $Fe(acac)_2$ to PhenIFe 1. The ethylene oligomerization performed with 10:1 molar ratio of $Fe(acac)_2$ to PhenIFe 1 produces an oligomer product which has productivity (in g

TABLE 2

| Example | mass of PBI 1, mg | Fe:PBI 1, Molar Ratio | Al:PBI 1, Molar Ratio | Temp., ° C. | Productivity grams ($C_4$-$C_{20}$) | g ($C_4$-$C_{20}$)/ mmol PBI 1 | $C_{12}/C_{10}$ Schulz-Flory K value |
|---|---|---|---|---|---|---|---|
| 7 | 0.05 | 1:1 | 10,000 | 60-70 | 5.30 | 39,100 | 0.74 |
| 8 | 0.05 | 5:1 | 10,000 | 60-70 | 35.52 | 262,100 | 0.69 |
| 9 | 0.05 | 10:1 | 10,000 | 60-70 | 45.22 | 333,700 | 0.73 |
| 10 | 0.05 | 20:1 | 10,000 | 60-70 | 31.65 | 233,600 | 0.71 |

The results of Examples 7-10 demonstrate that the use of a metal salt to heteroatomic ligand equivalent molar ratio greater than 1.2:1 in an ethylene oligomerization utilizing a heteroatomic ligand and a metal salt increases the productivity of ethylene oligomerization.

Examples 11-12

The heteroatomic ligand iron dichloride 2-[(2,6-diethylphenylimine)methyl-1,10-phenanthroline iron dichloride (PhenIFe 1) is prepared using the procedures disclosed in CN 104418690 A.

In a nitrogen-filled drybox, a stock toluene solution of 1.0 mg/mL ($4.15 \times 10^{-3}$ meq/mL) of PhenIFe 1 and a stock toluene solution 4.0 mg/mL ($1.57 \times 10^{-2}$ meq/mL) of $Fe(acac)_2$ are prepared. The appropriate amount of the PhenIFe 1 and of the $Fe(acac)_2$ stock solutions are added to a 5 mL NMR tube to provide the desired quantity of PhenIFe 1 and of $Fe(acac)_2$ for the ethylene oligomerization. The NMR tube is then sealed. Also in the nitrogen-filled drybox, a glass charger is charged with 100 mL cyclohexane, approximately 1.0 g of n-nonane internal standard, and the appropriate amount of MMAO-7 (Akzo Nobel, 7.0 wt % Al) to achieve the desired α-diimine ligand to aluminum molar ratio for the ethylene oligomerization. The glass charger is then sealed. The NMR tube and glass charger are then removed from the drybox. The NMR tube is secured to the stirrer shaft of a 500 mL autoclave reactor with wire in a manner where the glass will shatter on starting the mixer. The autoclave reactor is then sealed and evacuated under high vacuum. The glass charger is then affixed to a charging port on the top of the autoclave reactor. After evacuating the reactor for several minutes, the entire contents of the glass charger is loaded into the autoclave reactor under vacuum. The autoclave reactor is then degassed with ethylene by carrying out several fill/vent cycles. The reactor is then pressurized with ethylene to 400 psig (2.8 MPa). Stirring is ($C_4$-$C_{20}$)/mmol PhenIFe 1) 20% greater than the productivity of the ethylene oligomerization performed without added $Fe(acac)_2$.

Examples 13-15

The heteroatomic ligand iron dichloride 2-[(2,6-diethylphenylimine)methyl-1,10-phenanthroline (PhenI 1) is prepared using the procedures disclosed in CN 104418690 A.

In a nitrogen-filled drybox, a stock cyclohexane solution of 0.13 mg/mL ($3.65 \times 10^{-3}$ meq/mL) of PhenI 1 and a stock cyclohexane solution 1.0 mg/mL ($3.94 \times 10^{-3}$ meq/mL) of $Fe(acac)_2$ are prepared. The appropriate amount of the PhenI 1 and the $Fe(acac)_2$ stock solutions are added to a 5 mL NMR tube to provide the desired quantity of PhenI 1 and of $Fe(acac)_2$ for the ethylene oligomerization. The NMR tube is then sealed. Also in the nitrogen-filled drybox, a glass charger is charged with 200 mL cyclohexane, approximately 1.0 g of n-nonane internal standard, and the appropriate amount of MMAO-7 (Akzo Nobel, 7.0 wt % Al) to achieve the desired α-diimine ligand to aluminum molar ratio for the ethylene oligomerization. The glass charger is then sealed. The NMR tube and glass charger are then removed from the drybox. The NMR tube is secured to the stirrer shaft of a 1000 mL autoclave reactor with wire in a manner where the glass will shatter on starting the mixer. The autoclave reactor is then sealed and evacuated under high vacuum. The glass charger is then affixed to a charging port on the top of the autoclave reactor. After evacuating the reactor for several minutes, the entire contents of the glass charger are loaded into the autoclave reactor under vacuum. The autoclave reactor is then degassed with ethylene by carrying out several fill/vent cycles. The reactor is then pressurized with ethylene to 400 psig (2.8 MPa). Stirring is initiated resulting in breakage of the 5 mm NMR tube and activation of the catalyst. Ethylene is then fed to the autoclave reactor on demand to maintain a pressure of 400 psig (2.8 MPa) for the remainder of the reaction. The reaction temperature is maintained at a temperature of 60 to 70° C. by way of cooling water passed through internal cooling coils inside the autoclave reactor. After 15 min, the reactor is cooled to room temperature and vented to atmospheric pressure. The liquid products are analyzed by a gas chromatograph with a flame ionization detector (FID) detector against the n-nonane internal standard. The first ethylene oligomerization (Example 13) is performed with a 1:1 Fe(acac)$_2$ to PhenI 1 molar ratio. The second ethylene oligomerization (Example 14) is performed with a 5:1 Fe(acac)$_2$ to PhenI 1 molar ratio. The third ethylene oligomerization (Example 15) is performed with a 10:1 Fe(acac)$_2$ to PhenI 1 molar ratio. The ethylene oligomerization performed with 5:1 molar ratio of Fe(acac)$_2$ to PhenI 1 produces an oligomer product which has productivity (in g (C$_4$-C$_{20}$)/mmol PhenI 1) over 400% greater than the productivity of the ethylene oligomerization performed with a 1:1 molar ratio of Fe(acac)$_2$ to PhenI 1. The ethylene oligomerization performed with 10:1 molar ratio of Fe(acac)$_2$ to PhenI 1 produces an oligomer product which has productivity (in g (C$_4$-C$_{20}$)/mmol PhenI 1) over 600% greater than the productivity of the ethylene oligomerization performed with a 1:1 molar ratio of Fe(acac)$_2$ to PhenI 1.

We claim:

1. A process for forming an oligomer product comprising;
   a) introducing into a reaction zone
      i. ethylene;
      ii. a heteroatomic ligand, wherein the heteroatomic ligand is an α-diimine, a phenanthroline imine, or any combination thereof;
      iii. a metal salt where
         1) the metal salt is an iron salt, a cobalt salt, or any combination thereof, and
         2) an equivalent molar ratio of the metal salt to the heteroatomic ligand is at least 1.5:1;
      iv. an organoaluminum compound;
      v. optionally hydrogen; and
      vi. optionally an organic reaction medium; and
   b) forming an oligomer product in the reaction zone.

2. The process of claim 1, wherein the organo groups of the organoaluminum compound are substantially devoid of β,γ-branched organo groups and/or β,δ-branched organo groups.

3. The process of claim 1, wherein a C$_4$-C$_{20}$ productivity is at least 100% greater than the C$_4$-C$_{20}$ productivity of an otherwise similar process wherein an equivalent molar ratio of the metal salt to the heteroatomic ligand is less than 1.1:1.

4. The process of claim 1, wherein the heteroatomic ligand comprises 1) a bidentate metal salt complexing moiety or 2) a tridentate metal salt complexing moiety, wherein the bidentate metal salt complexing moiety and the tridentate metal salt complexing moiety each independently comprise at least two metal salt complexing groups selected from the group consisting of an imine group and an aromatic nitrogen atom containing group.

5. The process of claim 1, wherein the heteroatomic ligand is the α-diimine and the α-diimine comprises i) an α-diimine group, ii) a first imine group consisting of a hydrocarbyl group or substituted hydrocarbyl group attached to a first imine nitrogen atom of the α-diimine group, and iii) a second imine group comprising a metal salt complexing group and a linking group linking the metal salt complexing group to a second imine nitrogen atom of the α-diimine group.

6. The process of claim 5, wherein the the α-diimine comprises i) an α-diimine group derived from an aromatic diacyl compound, ii) a first imine group consisting of an aryl group or substituted aryl group, and iii) a second imine group comprising a diarylphosphinyl first metal salt complexing group and a —CH$_2$CH$_2$— linking group linking the diarylphosphinyl first metal salt complexing group to the second imine nitrogen atom.

7. The process of claim 5, wherein the α-diimine comprises i) an α-diimine group derived from acenaphthenequinone, phenanthrenequinone, or pyrenequinone, ii) a first imine group consisting of an 2,6-dihydrocarbylphenyl group, and iii) a second imine group comprising a diphenylphosphinyl metal salt complexing group or a di(substituted phenyl)phosphinyl metal complexing group and a —CH$_2$CH$_2$— linking group linking the metal salt complexing group to the second imine nitrogen atom.

8. The process of claim 1, wherein the heteroatomic ligand is the phenanthroline imine and the phenanthroline imine comprises a 2-(hydrocarbylimine)-1,10-phenanthroline, a 2-[(hydrocarbylimine)hydrocarbyl]-1,10-phenanthroline, a 2-(arylimine)-1,10-phenanthroline, a 2-[(arylimine)hydrocarbyl]-1,10-phenanthroline, a 2-(substituted arylimine)-1,10-phenanthroline, or a 2-[(substituted arylimine)hydrocarbyl]-1,10-phenanthroline.

9. The process of claim 8, wherein the phenanthroline imine comprises a 2-(2,6-dialkylphenylimine)-1,10-phenanthroline, a 2-[(2,6-dialkylphenylimine)alkyl]-1,10-phenanthroline, a 2-[(2,6-dialkylphenylimine)phenyl]-1,10-phenanthroline, a 2-(2,4,6-trialkylphenylimine)-1,10-phenanthroline, a 2-[(2,4,6-trialkylphenylimine)alkyl]-1,10-phenanthroline, a 2-[(2,4,6-trialkylphenylimine)phenyl]-1,10-phenanthroline, a 2-(2,6-dihalophenylimine)-1,10-phenanthroline, a 2-[(2,6-dihalophenylimine)alkyl]-1,10-phenanthroline, a 2-[(2,6-dihalophenylimine)phenyl-1,10-phenanthroline, or any combination thereof.

10. The process of claim 8, wherein phenanthroline imine is selected from the group consisting of 2-(2,6-difluorophenylimine)-1,10-phenanthroline, 2-(2,6-dichlorophenylimine)-1,10-phenanthroline, 2-(2,6-dibromophenylimine)-1,10-phenanthroline, 2-(2,6-dimethylphenylimine)-1,10-phenanthroline, 2-(2,6-diethylphenylimine)-1,10-phenanthroline, 2-(2,6-diisopropylphenylimine)-1,10-phenan-throline, 2-[(2,6-difluorophenylimine)methyl]-1,10-phenanthroline, 2-[(2,6-dichloropheny-limine)methyl]-1,10-phenanthroline, 2-[(2,6-dibromophenylimine)methyl]-1,10-phenanthroline, 2-[(2,6-dimethylphenylimine)methyl]-1,10-phenanthroline, 2-[(2,6-diethylphenylimine)methyl]-1,10-phenanthroline, 2-[(2,6-diisopropylphenylimine)methyl]-1,10-phenanthroline, 2-[(2,6-diethylphenylimine)ethyl]-1,10-phenanthroline, 2-[(2,6-diethylphenylimine)-n-propyl]-1,10-phenanthroline, 2-[(2,6-diethylphenylimine)iso-propyl]-1,10-phenanthroline, 2-[(2,4,6-tribromophenylimine)methyl]-1,10-phenanthroline, 2-[(2,4,6-trimethylphenylimine)methyl]-1,10-phenanthroline, 2-[(2,6-dimethyl-4-bromophenylimine)methyl]-1,10-phenanthroline, 2-[(2,6-dibromo-4-methylphenylimine)methyl]-1,10-phenanthroline, 2-[(2,6-dibromo-4-chlorophenylimine)methyl]-1,10-phenanthroline, 2-[(2,6-dimethylphenylimine)phenyl]-1,10-phenanthroline, 2-[(2,6-diethylphenylimine)phenyl]-1,10-phenanthroline, and 2-[(2,6-diisopropylphenyl-imine)phenyl]-1,10-phenanthroline.

11. The process of claim 1, wherein the organoaluminum compound comprises an aluminoxane.

12. The process of claim 11, wherein the aluminoxane comprises methylaluminoxane, a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

13. The process of claim 1, where the metal salt comprises an iron halide, an iron β-diketonate, an iron carboxylate, or any combination thereof.

14. The process of claim 1, wherein the oligomer product is formed under conditions of i) an heteroatomic ligand molar equivalent concentration of at least $1 \times 10^6$ mmol/kg based upon the total kg mass of all components in the reaction zone, ii) an aluminum of the organo aluminum compound to heteroatomic ligand molar equivalent ratio of at least 100:1, iii) an aluminum of the organoaluminum compound concentration of at least 0.3 mmol Al/kg based upon the total kg mass of all components in the reaction zone, and iv) an ethylene partial pressure of at least 100 psi, a temperature of at least 0° C.

15. The process of claim 14, wherein the equivalent molar ratio of the metal salt to the heteroatomic ligand ranges from 1.5:1 to 50:1 and the aluminoxane comprises methylaluminoxane, a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

16. The process of claim 1, wherein the heteroatomic ligand and the metal salt are introduced to the reaction zone as separate and distinct components.

\* \* \* \* \*